US010307374B2

(12) United States Patent
Brito et al.

(10) Patent No.: US 10,307,374 B2
(45) Date of Patent: Jun. 4, 2019

(54) OIL-IN-WATER EMULSIONS THAT CONTAIN NUCLEIC ACIDS

(71) Applicant: GLAXOSMITHKLINE BIOLOGICALS SA, Rixensart (BE)

(72) Inventors: Luis Brito, Concord, MA (US); Michelle C. Archer, Florence, MA (US); Andrew Geall, Littleton, MA (US); Derek O'Hagan, Winchester, MA (US); Manmohan Singh, Cary, NC (US)

(73) Assignee: GLAXOSMITHKLINE BIOLOGICALS S.A. (BE)

(*) Notice: Subject to any disclaimer, the term of this patent is extended or adjusted under 35 U.S.C. 154(b) by 0 days.

(21) Appl. No.: 15/495,066

(22) Filed: Apr. 24, 2017

(65) Prior Publication Data
US 2017/0224616 A1 Aug. 10, 2017

Related U.S. Application Data

(62) Division of application No. 14/130,880, filed as application No. PCT/US2012/045840 on Jul. 6, 2012, now Pat. No. 9,655,845.

(60) Provisional application No. 61/585,639, filed on Jan. 11, 2012, provisional application No. 61/505,091, filed on Jul. 6, 2011.

(51) Int. Cl.
*A61K 9/107* (2006.01)
*A61K 39/12* (2006.01)
*A61K 39/155* (2006.01)
*A61K 31/713* (2006.01)
*A61K 9/00* (2006.01)
*A61K 39/00* (2006.01)

(52) U.S. Cl.
CPC ............ *A61K 9/107* (2013.01); *A61K 31/713* (2013.01); *A61K 39/12* (2013.01); *A61K 39/155* (2013.01); *A61K 9/0019* (2013.01); *A61K 2039/53* (2013.01); *A61K 2039/55566* (2013.01); *C12N 2760/18534* (2013.01); *Y02A 50/412* (2018.01); *Y02A 50/489* (2018.01)

(58) Field of Classification Search
None
See application file for complete search history.

(56) References Cited

U.S. PATENT DOCUMENTS

| | | |
|---|---|---|
| 3,906,092 A | 9/1975 | Hilleman et al. |
| 5,264,618 A | 11/1993 | Felgner et al. |
| 5,384,133 A | 1/1995 | Boyes et al. |
| 5,670,152 A | 9/1997 | Weiner et al. |
| 5,712,257 A | 1/1998 | Carter |
| 5,739,118 A | 4/1998 | Carrano et al. |
| 5,795,587 A | 8/1998 | Gao et al. |
| 5,906,980 A | 5/1999 | Carter |
| 6,040,295 A | 3/2000 | Rolland et al. |
| 6,086,901 A | 7/2000 | O'Hagan et al. |
| 6,150,087 A | 11/2000 | Chien |
| 6,171,586 B1 | 1/2001 | Lam et al. |
| 6,218,371 B1 | 4/2001 | Krieg et al. |
| 6,239,116 B1 | 5/2001 | Krieg et al. |
| 6,299,884 B1 | 10/2001 | Van Nest et al. |
| 6,306,405 B1 | 10/2001 | O'Hagan et al. |
| 6,451,325 B1 | 9/2002 | Van Nest et al. |
| 6,458,370 B1 | 10/2002 | O'Hagan et al. |
| 6,610,321 B2 | 8/2003 | Huang et al. |
| 6,855,492 B2 | 2/2005 | O'Hagan et al. |
| 6,861,410 B1 | 3/2005 | Ott et al. |
| 6,884,435 B1 | 4/2005 | O'Hagan et al. |
| 6,890,554 B2 | 5/2005 | Jessee et al. |
| 7,303,881 B2 | 12/2007 | Huang et al. |
| 7,314,627 B2 | 1/2008 | Haynes et al. |
| 7,550,145 B2 | 6/2009 | O'Hagan et al. |
| 7,641,911 B2 | 1/2010 | Ott et al. |
| 7,749,520 B2 | 7/2010 | Davidsen et al. |
| 7,790,696 B2 | 9/2010 | Gregoriadis |
| 9,295,646 B2 | 3/2016 | Brito et al. |
| 9,655,845 B2 * | 5/2017 | Brito ............... A61K 39/155 |
| 9,801,897 B2 * | 10/2017 | Geall ............... A61K 39/00 |
| 2002/0077305 A1 | 6/2002 | Jessee et al. |
| 2003/0170273 A1 | 9/2003 | O'Hagan et al. |
| 2006/0084617 A1 | 4/2006 | Satishchandran |
| 2009/0017057 A1 | 1/2009 | Chen et al. |
| 2011/0110972 A1 | 5/2011 | Vasievich et al. |
| 2012/0156251 A1 | 6/2012 | Brito et al. |
| 2013/0195968 A1 | 8/2013 | Geall et al. |

(Continued)

FOREIGN PATENT DOCUMENTS

| | | |
|---|---|---|
| EP | 1723972 A1 | 11/2006 |
| JP | 2008517918 A | 5/2008 |
| JP | 2009531283 A | 9/2009 |

(Continued)

OTHER PUBLICATIONS

Liu, et al. (1996) "Effect of Non-Ionic Surfactants on the Formation of DNA/Emulsion Complexes and Emulsion-Mediated Gene Transfer", Pharmaceutical Research, 13(11): 1642-46.*
Parkin et al., An overview of the immune system. Lancet. Jun. 2, 2001;357(9270):1777-89.
Pascolo, Vaccination with messenger RNA (mRNA). Handb Exp Pharmacol. 2008;(183):221-35.
Pascolo, Vaccination with messenger RNA. Methods Mol Med. 2006;127:23-40.

(Continued)

*Primary Examiner* — Robert M Kelly

(57) ABSTRACT

This invention generally relates to cationic oil-in-water emulsions that can be used to deliver nucleic acid molecules, such as an RNA molecule. The emulsion particles comprise an oil core and a cationic lipid. The emulsion particles have an average diameter of about 80 nm to about 180 nm, and the emulsion have an N/P ratio of at least 1.1:1.

27 Claims, 5 Drawing Sheets
Specification includes a Sequence Listing.

(56) References Cited

U.S. PATENT DOCUMENTS

2014/0212498 A1 7/2014 Brito et al.

FOREIGN PATENT DOCUMENTS

| JP | 2009534342 A | 9/2009 |
|---|---|---|
| WO | 1990014837 A1 | 12/1990 |
| WO | 199622765 A1 | 8/1996 |
| WO | 1997011682 A2 | 4/1997 |
| WO | 199833487 A1 | 8/1998 |
| WO | 199902132 A2 | 1/1999 |
| WO | 199930737 A1 | 6/1999 |
| WO | 200006123 A1 | 2/2000 |
| WO | 200015768 A1 | 3/2000 |
| WO | 200050006 A2 | 8/2000 |
| WO | 200067787 A2 | 11/2000 |
| WO | 200136599 A1 | 5/2001 |
| WO | 200226209 A2 | 4/2002 |
| WO | 2003028656 A2 | 4/2003 |
| WO | 2004053056 A2 | 6/2004 |
| WO | 2007001423 A2 | 1/2007 |
| WO | 2007121947 A1 | 11/2007 |
| WO | 2008029276 A2 | 3/2008 |
| WO | 2008116078 A2 | 9/2008 |
| WO | 2009129227 A1 | 10/2009 |
| WO | 2010009277 A2 | 1/2010 |
| WO | 2011005799 A2 | 1/2011 |
| WO | 2012006380 A2 | 1/2012 |
| WO | 2013006834 A1 | 1/2013 |
| WO | 2013006837 A1 | 1/2013 |

OTHER PUBLICATIONS

Perrie et al., Liposome-mediated DNA vaccination: the effect of vesicle composition. Vaccine. Apr. 30, 2001;19(23-24):3301-10.
Pizza et al., Identification of vaccine candidates against serogroup B meningococcus by whole-genome sequencing. Science. Mar. 10, 2000;287(5459):1816-20.
Semple et al., Rational design of cationic lipids for siRNA delivery. Nat Biotechnol. Feb. 2010;28(2):172-6.
Shi et al., TLR4 links innate immunity and fatty acid-induced insulin resistance. J Clin Invest. Nov. 2006;116(11):3015-25.
Simberg et al., DOTAP (and other cationic lipids): chemistry, biophysics, and transfection. Crit Rev Ther Drug Carrier Syst. 2004;21(4):257-317.
Singh et al., Advances in vaccine adjuvants. Nat Biotechnol. Nov. 1999;17(11):1075-81.
Singh et al., Cationic microparticles: A potent delivery system for DNA vaccines. Proc Natl Acad Sci U S A. Jan. 18, 2000;97(2):811-6.
Suh et al., Anionic amino acid-derived cationic lipid for siRNA delivery. J Control Release. Dec. 16, 2009;140(3):268-76.
Tabatt et al., Effect of cationic lipid and matrix lipid composition on solid lipid nanoparticle-mediated gene transfer. Eur J Pharm Biopharm. Mar. 2004;57(2):155-62.
Tagliabue et al., Vaccine adjuvants: the dream becomes real. Hum Vaccin. Sep.-Oct. 2008;4(5):347-9.
Tamilvanan et al., Manufacturing techniques and excipients used during the formulation of oil-in-water type nanosized emulsions for medical applications. J Excipients and Food Chem. 2010;1(1):11-29.
Tamilvanan et al., Stability assessment of injectable castor oil-based nano-sized emulsion containing cationic droplets stabilized by poloxamer-chitosan emulsifier films. AAPS PharmSciTech. Jun. 2010;11(2):904-9.
Tazulakhova et al., Russian experience in screening, analysis, and clinical application of novel interferon inducers. J Interferon Cytokine Res. Feb. 2001;21(2):65-73.
Vajdy et al., Mucosal adjuvants and delivery systems for protein-, DNA- and RNA-based vaccines. Immunol Cell Biol. Dec. 2004;82(6):617-27.

Walker et al., Cationic lipids direct a viral glycoprotein into the class I major histocompatibility complex antigen-presentation pathway. Proc Natl Acad Sci U S A. Sep. 1, 1992;89(17):7915-8.
Weide et al., Plasmid DNA- and messenger RNA-based anti-cancer vaccination. Immunol Lett. Jan. 15, 2008;115(1):33-42.
Wikipedia. Phosphate-buffered saline. retrieved online at: https://en.wikipedia.org/wiki/phosphate_buffered_saline, 2 pages, page last modified on Mar. 23, 2017.
Yew et al., Toxicity of cationic lipid-DNA complexes. Adv Genet. 2005;53:189-214.
Yi et al., A cationic lipid emulsion/DNA complex as a physically stable and serum-resistant gene delivery system. Pharm Res. Mar. 2000;17(3):314-20.
Ying et al., Cancer therapy using a self-replicating RNA vaccine. Nat Med. Jul. 19991;5(7):823-7.
Yoo et al., In vivo gene therapy of type I diabetic mellitus using a cationic emulsion containing an Epstein Barr Virus (EBV) based plasmid vector. J Control Release. May 1, 2006;112(1):139-44.
Zur Mühlen et al., Solid lipid nanoparticles (SLN) for controlled drug delivery—drug release and release mechanism. Eur J Pharm Biopharm. Mar. 1998;45(2):149-55.
Benita et al., Submicron emulsions as colloidal drug carriers for intravenous administration: comprehensive physicochemical characterization. J Pharm Sci. Nov. 1993;82(11):1069-79.
Bramson et al., Activation of host antitumoral responses by cationic lipid/DNA complexes. Cancer Gene Ther. Mar. 2000;7(3):353-9.
Brgles et al., Liposome fusogenicity and entrapment efficiency of antigen determine the Th1/Th2 bias of antigen-specific immune response. Vaccine. Sep. 4, 2009;27(40):5435-42.
Brito et al., A cationic nanoemulsion for the delivery of next-generation RNA vaccines. Mol Ther. Dec. 2014;22(12):2118-29.
Cella et al., Maturation, activation, and protection of dendritic cells induced by double-stranded RNA. J Exp Med. Mar. 1, 1999;189(5):821-9.
Choi et al., Low toxicity of cationic lipid-based emulsion for gene transfer. Biomaterials. Dec. 2004;25(27):5893-903.
Chung et al., Oil components modulate physical characteristics and function of the natural oil emulsions as drug or gene delivery system. J Control Release. Apr. 28, 2001;71(3):339-50.
Dow et al., Lipid-DNA complexes induce potent activation of innate immune responses and antitumor activity when administered intravenously. J Immunol. Aug. 1, 1999;163(3):1552-61.
Dupuis et al., Dendritic cells internalize vaccine adjuvant after intramuscular injection. Cell Immunol. May 25, 1998;186(1):18-27.
El Ouahabi et al., Double long-chain amidine liposome-mediated self replicating RNA transfection. FEBS Lett. Feb. 12, 1996;380(1-2):108-12.
Elbashir et al., Duplexes of 21-nucleotide RNAs mediate RNA interference in cultured mammalian cells. Nature. May 24, 2001;411(6836):494-8.
Even-Chen et al., DOTAP cationic liposomes prefer relaxed over supercoiled plasmids. Biochim Biophys Acta. Dec. 20, 2000;1509(1-2):176-88.
Fire, RNA-triggered gene silencing. Trends Genet. Sep. 1999;15(9):358-63.
Fox, Squalene emulsions for parenteral vaccine and drug delivery. Molecules. Sep. 1, 2009;14(9):3286-312.
Geall et al., Nonviral delivery of self-amplifying RNA vaccines. Proc Natl Acad Sci U S A. Sep. 4, 2012;109(36):14604-9.
Gregoriadis et al., Liposome-mediated DNA vaccination. FEBS Lett. Feb. 3, 1997;402(2-3):107-10.
Guy, The perfect mix: recent progress in adjuvant research. Nat Rev Microbiol. Jul. 2007;5(7):505-17.
Hagigit et al., The influence of cationic lipid type on in-vitro release kinetic profiles of antisense oligonucleotide from cationic nanoemulsions. Eur J Pharm Biopharm. Sep. 2008;70(1):248-59.
Heyes et al., Cationic lipid saturation influences intracellular delivery of encapsulated nucleic acids. J Control Release. Oct. 3, 2005;107(2):276-87.
Hoerr et al., In vivo application of RMA leads to induction of specific cytotoxic T lymphocytes and antibodies. Eur J Immunol. Jan. 2000;30(1):1-7.

(56) References Cited

OTHER PUBLICATIONS

Hung et al., Physicochemical characterization and gene transfection efficiency of lipid emulsions with various co-emulsifiers. Int J Pharm. Jan. 31, 2005;289(1-2):197-208.

James-Smith et al., Determination of drug and fatty acid binding capacity to pluronic f127 in microemulsions. Langmuir. Feb. 13, 2007;23(4):1640-4.

Jeffs et al., A scalable, extrusion-free method for efficient liposomal encapsulation of plasmid DNA. Pharm Res. Mar. 2005;22(3):362-72.

Kang et al., Delivery of interleukin-18 gene to lung cancer cells using cationic emulsion. J Drug Target. Jan. 2009;17(1)19-28.

Kim et al., Airway gene transfer using cationic emulsion as a mucosal gene carrier. J Gene Med. Jun. 2005;7(6):749-58.

Kim et al., Influence of sucrose on droplet flocculation in hexadecane oil-in-water emulsions stabilized by beta-lactoglobulin. J Agric Food Chem. Jan. 29, 2003;51(3):766-72.

Kim et al., Optimization of lipid composition in cationic emulsion as in vitro and in vivo transfection agents. Pharm Res. Jan. 2001;18(1):54-60.

Kim et al., Polycations enhance emulsion-mediated in vitro and in vivo transfection. Int J Pharm. May 13, 2005;295(1-2)35-45.

Kwon et al., In vivo time-dependent gene expression of cationic lipid-based emulsion as a stable and biocompatible non-viral gene carrier. J Control Release. May 22, 2008;128(1):89-97.

Le Bon et al., Type i interferons potently enhance humoral immunity and can promote isotype switching by stimulating dendritic cells in vivo. Immunity. Apr. 2001;14(4):461-70.

Lee et al., Novel molecular approaches to cystic fibrosis gene therapy. Biochem J. Apr. 1, 2005;387(Pt 1):1-15.

Liu et al., Effect of non-ionic surfactants on the formation of DNA/emulsion complexes and emulsion-mediated gene tansfer. Pharm Res. Nov. 1996;13(11):1642-6.

Lomova et al., Antioxidant coating of micronsize droplets for prevention of lipid peroxidation in oil-in-water emulsion. ACS Appl Mater Interfaces. Dec. 2010;2(12):3669-76.

Majde et al., Viral double-stranded RNA, cytokines, and the flu. J Interferon Cytokine Res. Mar. 2000;20(3):259-72.

Malone et al., Cationic liposome-mediated RNA transfection. Proc Natl Acad Sci U S A. Aug. 1989;86(16):6077-81.

Martinon et al., Induction of virus-specific cytotoxic T lymphocytes in vivo by liposome-entrapped mRNA. Eur J Immunol. Jul. 1993;23(7):1719-22.

McCluskie et al., CpG DNA is an effective oral adjuvant to protein antigens in mice. Vaccine. Nov. 22, 2000;19(7-8):950-7.

Min et al., Improved gene expression pattern using Epstein-Barr virus (EBV)-based plasmid and cationic emulsion. Biomaterials. Mar. 2005;26(9):1063-70.

Montana et al., Cloning, expression, and localization of a new member of a Paracentrotus lividus cell surface multigene family. Mol Reprod Dev. May 1996;44(1):36-43.

Montana et al., Employment of cationic solid-lipid nanoparticles as RNA carriers. Bioconjug Chem. Mar.-Apr. 2007;18(2):302-8.

Moret et al., Stability of PEI-DNA and DOTAP-DNA complexes: effect of alkaline pH, heparin and serum. J Control Release. Sep. 11, 2001;76(1-2):169-81.

Moss et al., Human immunodeficiency virus (HIV)-specific immune responses are generated with the simultaneous vaccination of a gp120-depleted, whole-killed HIV-1 immunogen with cytosine-phosphorothioate-guanine dinucleotide immunostimulatory sequences of DNA. J Hum Virol. Jan.-Feb. 2001;4(1):39-43.

Moss et al., In vitro immune function after vaccination with an inactivated, gp120-depleted HIV-1 antigen with immunostimulatory oligodeoxynucleotides. Vaccine. Jan. 6, 2000;18(11-12):1081-7.

Nam et al., Lipid-based emulsion system as non-viral gene carriers. Arch Pharm Res. May 2009;32(5):639-46.

O'Hagan et al., Induction of potent immune responses by cationic microparticles with adsorbed human immunodeficiency virus DNA vaccines. J Virol. Oct. 2001;75(19):9037-43.

O'Hagan et al., Microparticles in MF59, a potent adjuvant combination for a recombinant protein vaccine against HIV-1. Vaccine. Mar. 6, 2000;18(17):1793-801.

O'Hagan et al., Synergistic adjuvant activity of immunostimulatory DNA and oil/water emulsions for immunization with HIV p55 gag antigen. Vaccine. Sep. 10, 2002;20(27-28):3389-98.

Opawale et al., Influence of interfacial rheological properties of mixed emulsifier films on the stability of water-in-oil-in-water emulsions. J Pharm Pharmacol. Sep. 1998;50(9):965-73.

Ott et al., A cationic sub-micron emulsion (MF59/DOTAP) is an effective delivery system for DNA vaccines. J Control Release. Feb. 19, 2002;79(1-3):1-5.

Ott et al., MF59—Design and Evaluation of a Safe and Potent Adjuvant for Human Vaccines. Vaccine Design: The Subunit and Adjuvant Approach, vol. 6, Chapter 10 of the series Pharmaceutical Biotechnology, pp. 277-296. Powell, M.F. and NEwman, M.J., eds., Plenum Press, New York (1995).

\* cited by examiner

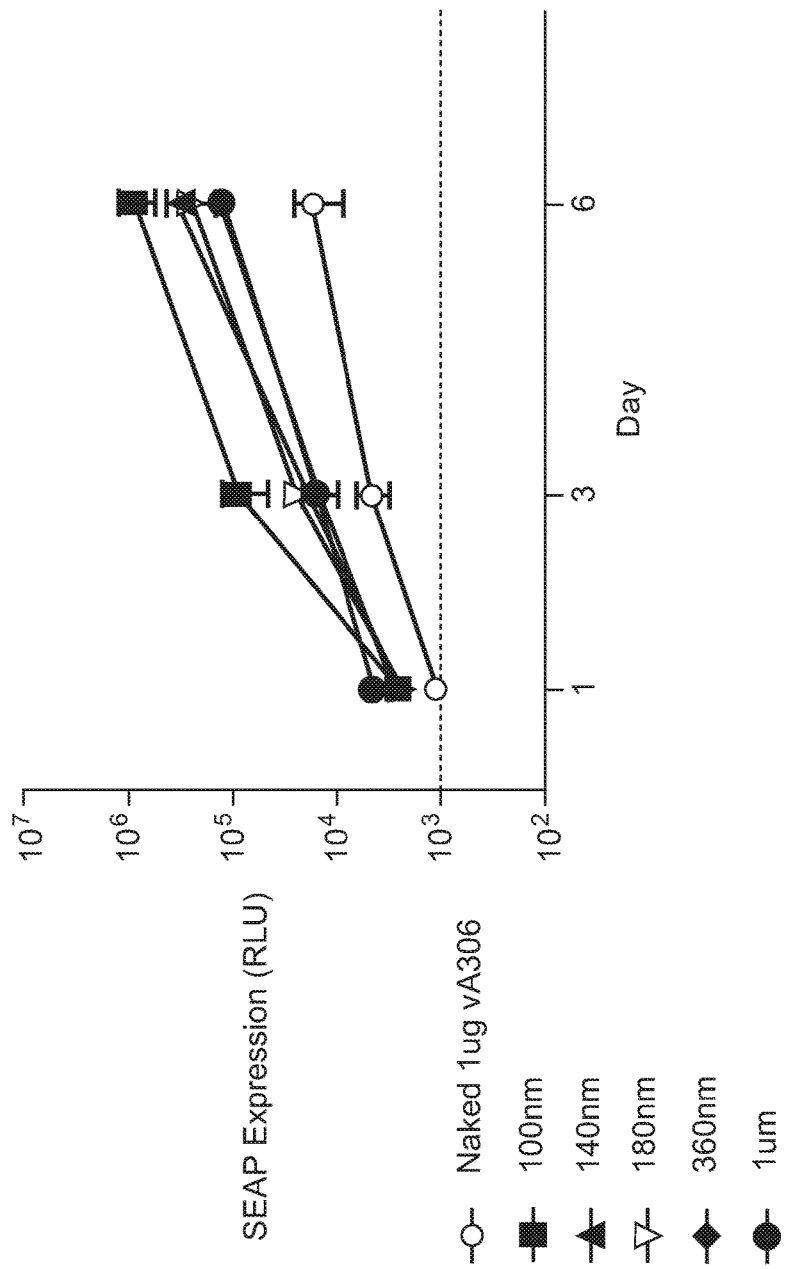

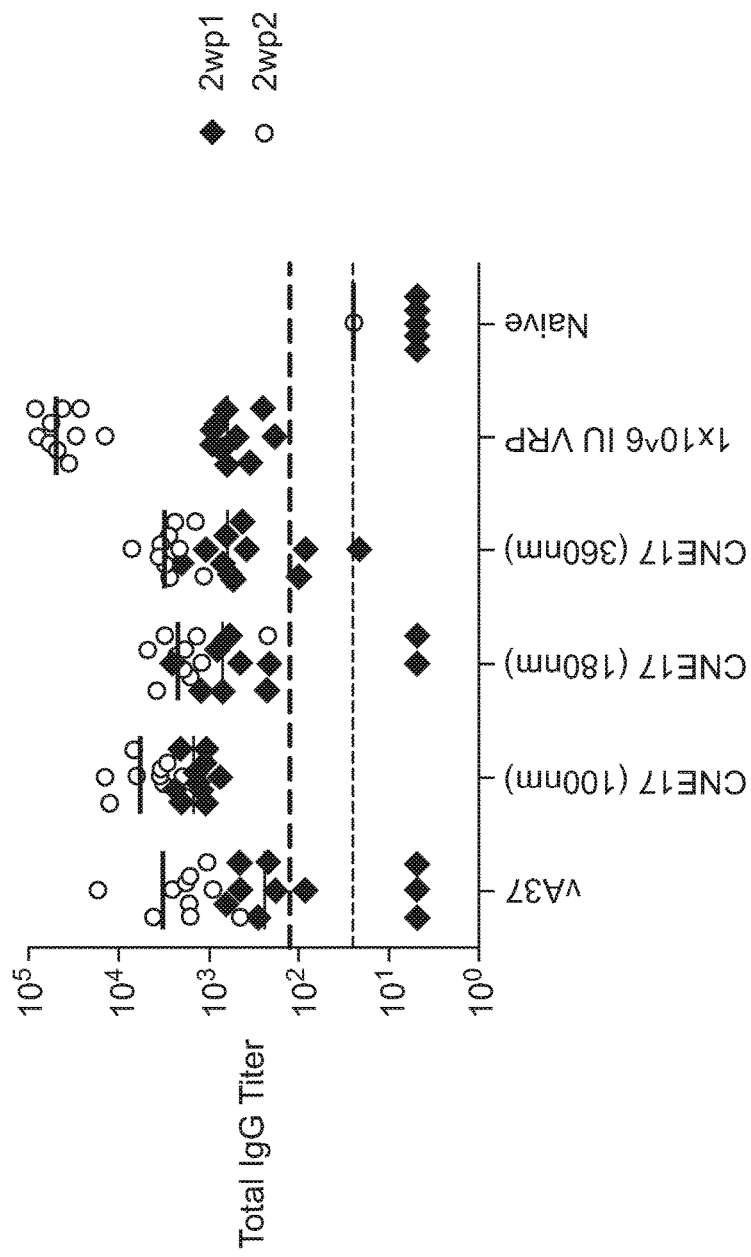

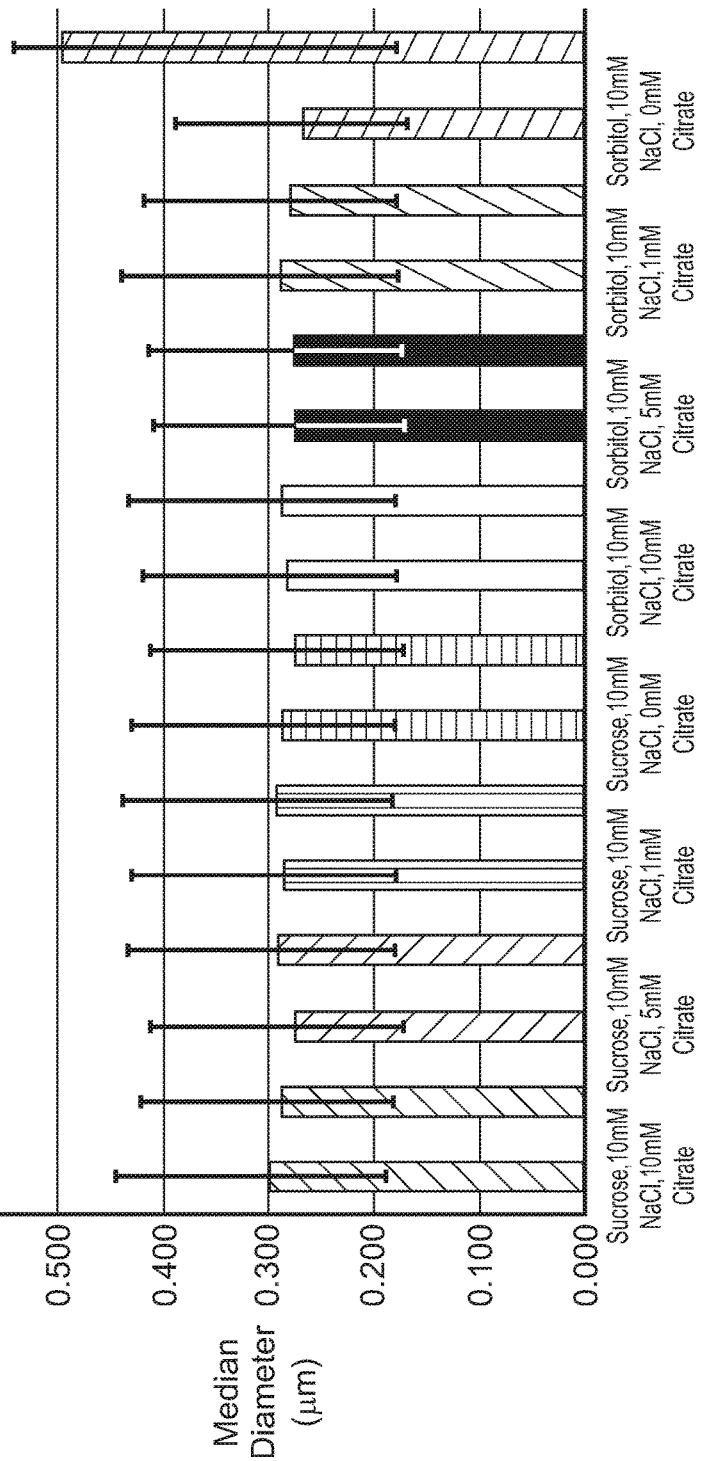

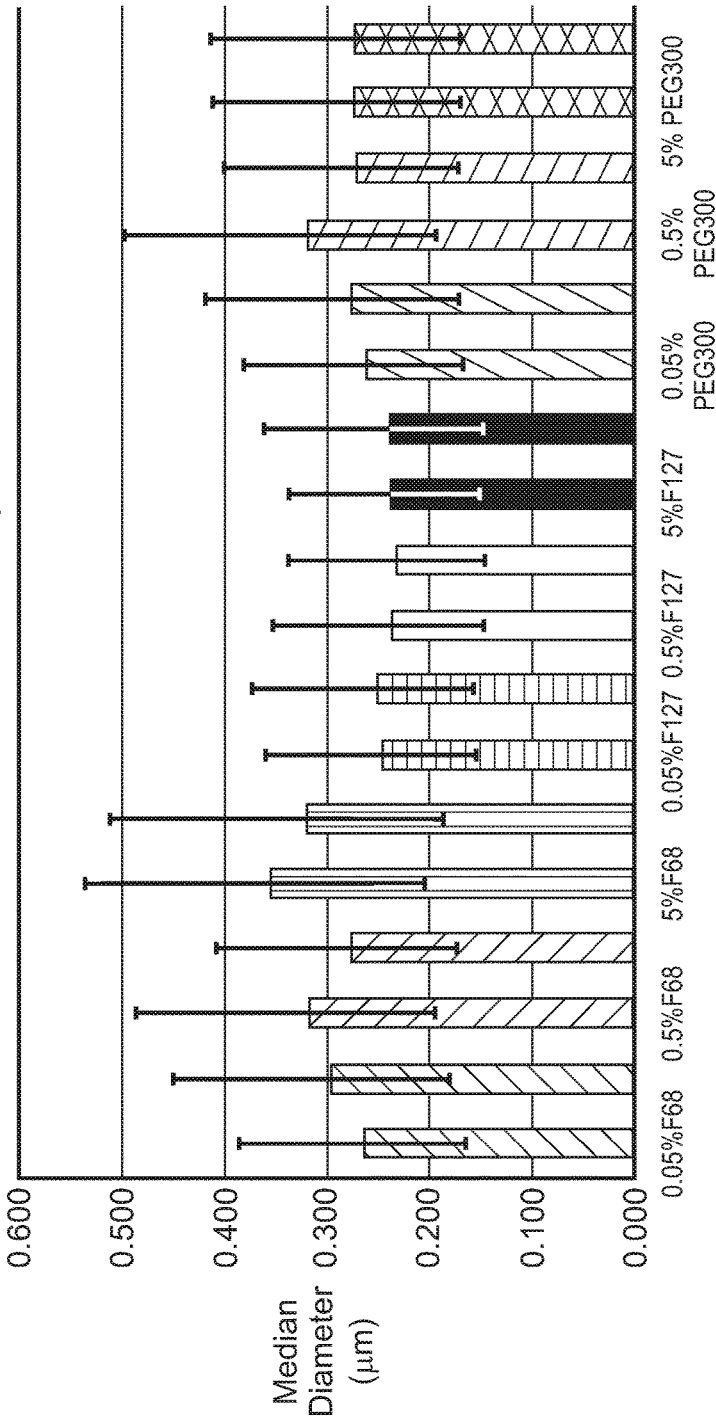

OIL-IN-WATER EMULSIONS THAT CONTAIN NUCLEIC ACIDS

SEQUENCE LISTING

The instant application contains a Sequence Listing which has been submitted in ASCII format via EFS-Web and is hereby incorporated by reference in its entirety. Said ASCII copy, created on Jan. 3, 2014, is named PAT054719.txt and is 32,549 bytes in size.

BACKGROUND OF THE INVENTION

Nucleic acid therapeutics have promise for treating diseases ranging from inherited disorders to acquired conditions such as cancer, infectious disorders (AIDS), heart disease, arthritis, and neurodegenerative disorders (e.g., Parkinson's and Alzheimer's). Not only can functional genes be delivered to repair a genetic deficiency or induce expression of exogenous gene products, but nucleic acid can also be delivered to inhibit endogenous gene expression to provide a therapeutic effect. Inhibition of gene expression can be mediated by, e.g., antisense oligonucleotides, double-stranded RNAs (e.g., siRNAs, miRNAs), or ribozymes.

A key step for such therapy is to deliver nucleic acid molecules into cells in vivo. However, in vivo delivery of nucleic acid molecules, in particular RNA molecules, faces a number of technical hurdles. First, due to cellular and serum nucleases, the half life of RNA injected in vivo is only about 70 seconds (see, e.g., Kurreck, Eur. J. Bioch. 270: 1628-44 (2003)). Efforts have been made to increase stability of injected RNA by the use of chemical modifications; however, there are several instances where chemical alterations led to increased cytotoxic effects or loss of or decreased function. In one specific example, cells were intolerant to doses of an RNAi duplex in which every second phosphate was replaced by phosphorothioate (Harborth, et al, Antisense Nucleic Acid Drug Rev. 13(2): 83-105 (2003)). As such, there is a need to develop delivery systems that can deliver sufficient amounts of nucleic acid molecules (in particular RNA molecules) in vivo to elicit a therapeutic response, but that are not toxic to the host.

Nucleic acid based vaccines are an attractive approach to vaccination. For example, intramuscular (IM) immunization of plasmid DNA encoding for antigen can induce cellular and humoral immune responses and protect against challenge. DNA vaccines offer certain advantages over traditional vaccines using protein antigens, or attenuated pathogens. For example, as compared to protein vaccines, DNA vaccines can be more effective in producing a properly folded antigen in its native conformation, and in generating a cellular immune response. DNA vaccines also do not have some of the safety problems associated with killed or attenuated pathogens. For example, a killed viral preparation may contain residual live viruses, and an attenuated virus may mutate and revert to a pathogenic phenotype.

Another limitation of nucleic acid based vaccines is that large doses of nucleic acid are generally required to obtain potent immune responses in non-human primates and humans. Therefore, delivery systems and adjuvants are required to enhance the potency of nucleic acid based vaccines. Various methods have been developed for introducing nucleic acid molecules into cells, such as calcium phosphate transfection, polyprene transfection, protoplast fusion, electroporation, microinjection and lipofection.

Cationic lipids have been widely formulated as liposomes to deliver genes into cells. However, even a small amount of serum (~10%) can dramatically reduce the transfection activity of liposome/DNA complexes because serum contains anionic materials. Recently, cationic lipid emulsion was developed to deliver DNA molecules into cells. See, e.g., Kim, et al., International Journal of Pharmaceutics, 295, 35-45 (2005).

U.S. Pat. Nos. 6,753,015 and 6,855,492 describe a method of delivering nucleic acid molecules to a vertebrate subject using cationic microparticles. The microparticles comprise a polymer, such as a poly($\alpha$-hydroxy acid), a polyhydroxy butyric acid, a polycaprolactone, a polyorthoester, a polyanhydride, and the like, and are formed using cationic surfactants. Nucleic acid molecules are adsorbed on the surfaces of the microparticles.

Kim et al. (Pharmaceutical Research, vol. 18, pages 54-60, 2001) and Chung et al. (Journal of Controlled Release, volume 71, pages 339-350, 2001) describe various oil-in-water emulsion formulations that are used to enhance in vitro and in vivo transfection efficiency of DNA molecules.

Ott et al. (Journal of Controlled Release, volume 79, pages 1-5, 2002) describes an approach involving a cationic sub-micron emulsion as a delivery system/adjuvant for DNA. The sub-micron emulsion approach is based on MF59, a potent squalene in water adjuvant which has been manufactured at large scale and has been used in a commercially approved product (Fluad®). 1,2-dioleoyl-3-trimethylammonium-propane (DOTAP) was used to facilitate intracellular delivery of plasmid DNA.

Although DNA-based vaccines hold great promise for prevention and treatment of diseases, general concerns have been raised regarding their safety. The introduced DNA molecules could potentially integrate into the host genome or, due to their distribution to various tissues, could lead to undesirable sustained expression of antigens. In addition, certain DNA viruses have also been used as a vehicle to deliver DNA molecules. Because of their infectious properties, such viruses achieve a very high transfection rate. The viruses used are genetically modified in such a manner that no functional infectious particles are formed in the transfected cell. Despite these precautions, however, it is not possible to rule out the risk of uncontrolled propagation of the introduced gene and viral genes, for example due to potential recombination events. This also entails the risk of the DNA being inserted into an intact gene of the host cell's genome by e.g. recombination, with the consequence that this gene may be mutated and thus completely or partially inactivated or may give rise to misinformation. In other words, synthesis of a gene product which is vital to the cell may be completely suppressed or, alternatively, a modified or incorrect gene product is expressed. In addition, it is generally difficult to scale up the manufacture and purification of clinical-grade viral vectors.

One particular risk occurs if the DNA is integrated into a gene which is involved in the regulation of cell growth. In this case, the host cell may become degenerate and lead to cancer or tumor formation. Furthermore, if the DNA introduced into the cell is to be expressed, it is necessary for the corresponding DNA vehicle to contain a strong promoter, such as the viral CMV promoter. The integration of such promoters into the genome of the treated cell may result in unwanted alterations of the regulation of gene expression in the cell. Another risk of using DNA as an agent to induce an immune response (e.g. as a vaccine) is the induction of pathogenic anti-DNA antibodies in the patient into whom the foreign DNA has been introduced, so bringing about an undesirable immune response.

RNA molecules encoding an antigen or a derivative thereof may also be used as vaccines. RNA vaccines offer certain advantages as compared to DNA vaccines. First, RNA cannot integrate into the host genome thus abolishing the risk of malignancies. Second, due to the rapid degradation of RNA, expression of the foreign transgene is often short-lived, avoiding uncontrolled long term expression of the antigen. Third, RNA molecules only need to be delivered to the cytoplasm to express the encoded antigen, whereas DNA molecules must permeate through the nuclear membrane.

Nonetheless, compared with DNA-based vaccines, relatively minor attention has been given to RNA-based vaccines. RNAs and oligonucleotides are hydrophilic, negatively charged molecules that are highly susceptible to degradation by nucleases when administered as a therapeutic or vaccine. Additionally, RNAs and oligonucleotides are not actively transported into cells. See, e.g., Vajdy, M., et al., *Mucosal adjuvants and delivery systems for protein-, DNA- and RNA-based vaccines*, Immunol Cell Biol, 2004. 82(6): p. 617-27.

Ying et al. (Nature Medicine, vol. 5, pages 823-827, 1999) describes a self-replicating RNA vaccine in which naked RNA encoding β-galactosidase was delivered and the induction of CD8+ cells was reported.

Montana et al. (Bioconjugate Chem. 2007, 18, pages 302-308) describes using cationic solid-lipid nanoparticles as RNA carriers for gene transfer. It was shown that solid-lipid nanoparticles protected the RNA molecule from degradation, and the expression of reporter protein (fluorescein) was detected after microinjecting the RNA-particle complex into sea urchin eggs.

WO 2010/009277 discloses Nano Lipid Peptide Particles (NLPPs) comprising (a) an amphipathic peptide, (b) a lipid, and (c) at least one immunogenic species. In certain embodiments, the NLPPs also incorporate a positively charged "capturing agent," such as a cationic lipid. The capturing agent is used to anchor a negatively charged immunogenic species (e.g., a DNA molecule or an RNA molecule). Preparation of NLPP requires amphipathic peptides, which are used to solubilize the lipid component and to form nano-particles.

Therefore, there is a need to provide delivery systems for nucleic acid molecules. The delivery systems are useful for nucleic acid-based vaccines, in particular RNA-based vaccines.

SUMMARY OF THE INVENTION

This invention generally relates to cationic oil-in-water emulsions in which a nucleic acid molecule is complexed to the emulsion particles. The emulsions can be used to deliver nucleic acide molecules, such as an RNA molecule to cells. The emulsion particles comprise an oil core and a cationic lipid. The cationic lipid can interact with the negatively charged molecule thereby anchoring the molecule to the emulsion particles. The emulsion particles have an average diameter of about 80 nm to about 180 nm, and the emulsion have an N/P ratio of at least 4:1.

In some embodiments, the emulsion particles have an average diameter of about 80 nm to about 180 nm, and the emulsion have an N/P ratio of at least 1.1:1, at least 1.5:1, at least 2:1, at least 2.5:1, at least 3:1, or at least 3.5:1.

The invention provides an immunogenic cationic oil-in-water emulsion comprising emulsion particles that contain an oil core and a cationic lipid, and a nucleic acid molecule that is complexed to the emulsion particles, and wherein the average diameter of the emulsion particles is from about 80 nm to about 180 nm and the N/P of the emulsion is at least 4:1; with the proviso that the nucleic acid molecule does not encode secreted alkaline phosphatase, and the further proviso that the nucleic acid molecule is not an RNA encoded by the plasmid A317, the sequence of which is shown in FIG. 7A of U.S. Patent Application No. 61/361,892. In some embodiments, the invention includes the further proviso that the nucleic acid molecule does not encode an RSV F protein antigen, and/or the further proviso that the nucleic acid molecule does not encode an RSV protein. Preferably, the nucleic acid molecule encodes an antigen, and is an RNA molecule, such as a self-replicating RNA.

The immunogenic cationic oil-in-water emulsion can be buffered, (e.g., with a citrate buffer, a succinate buffer, an acetate buffer) and has a pH from about 6.0 to about 8.0, preferably about 6.2 to about 6.8. Optionally, the immunogenic cationic oil-in-water emulsion further comprises an inorganic salt, preferably at a concentration no greater than 30 mM. Alternatively or in addition, the immunogenic cationic oil-in-water emulsion further comprises a nonionic tonicifying agent, such as a sugar, a sugar alcohol or combinations thereof, and or a polymer, such as a poloxamer, in the aqueous phase. If present, the polymer can be present in about 0.05% to about 20% (w/v). In some embodiments, immunogenic cationic oil-in-water emulsion is isotonic. In other embodiments, immunogenic cationic oil-in-water emulsions are hypotonic or hypertonic.

In some embodiments, the oil core of the emulsion parties comprises an oil that is selected from the group consisting of: Castor oil, Coconut oil, Corn oil, Cottonseed oil, Evening primrose oil, Fish oil, Jojoba oil, Lard oil, Linseed oil, Olive oil, Peanut oil, Safflower oil, Sesame oil, Soybean oil, Squalene, Squalane, Sunflower oil, Wheatgerm oil, and combinations thereof. In particular embodiments, the oil core is squalene. The cationic lipid can be selected from the group consisting of: 1,2-dioleoyloxy-3-(trimethylammonio) propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), Lipids E0001-E0118, and combinations thereof. In a preferred embodiment, the cationic lipid is DOTAP.

The emulsion particles can further comprise a surfactant, such as a nonionic surfactant. Preferably, the surfactant is not a Polyethylene Glycol (PEG)-lipid. The surfactant can be present in an amount from about 0.01% to about 2.5% (w/v). In some embodiments, the surfactant is SPAN85 (Sorbtian Trioleate), Tween 80 (polysorbate 80), or a combination thereof. In some embodiments, the oil-in-water emulsion contains equal amounts of SPAN85 (Sorbtian Trioleate) and Tween 80 (polysorbate 80), for example 0.5% (w/v) of each particle further comprises a surfactant.

The invention also relates to a method for making immunogenic cationic oil-in-water emulsion comprising emulsion particles that contain an oil core and a cationic lipid, and a nucleic acid molecule that is complexed to the emulsion particles, and wherein the average diameter of the emulsion particles is from about 80 nm to about 180 nm and the N/P of the emulsion is at least 4:1; with the proviso that the nucleic acid molecule does not encode secreted alkaline phosphatase, and the further proviso that the nucleic acid molecule is not an RNA encoded by the plasmid A317, the sequence of which is shown in FIG. 7A of U.S. Patent Application No. 61/361,892. The method comprises providing (i) a cationic oil-in-water emulsions containing emulsion particles that contain an oil core and a cationic lipid as described herein, and (ii) an aqueous solution that contains a nucleic acid, and combining (i) and (ii) thereby making said immunogenic cationic oil-in-water emulsion.

The invention also relates to a method for generating an immune response in a subject, comprising administering to the subject an effective amount of an immunogenic cationic oil-in-water emulsion described herein.

BRIEF DESCRIPTION OF THE DRAWINGS

FIG. 1A shows the results of an in vivo SEAP assay, using 1 µg of RNA replicon vA306 complexed with CNE17 at 10:1 N:P ratio. FIG. 1B shows the total IgG titers in BALB/c mice at 2wp1 and 2wp2 time points following immunization with RNA replicon A317, which encodes RSV F protein, complexed with CNE17. These data show that as particle size increased, SEAP expression decreased, and the immune response to RSV F protein decreased.

FIGS. 2A-2C show the effects of RNA complexation and different buffer compositions on particle size. FIG. 2A shows that RNA complexation increased the particle size in CNE 17 emulsion, and that sugar and/or low salt (NaCl, 10 mM) decreased particle size. The addition of Pluronic F127 reduced particle size to precomplexation size. FIG. 2B shows the effect of citrate buffer on particle size. FIG. 2C shows the effect of polymers on particle size.

DETAILED DESCRIPTION OF THE INVENTION

1. Overview

Figure 2A:
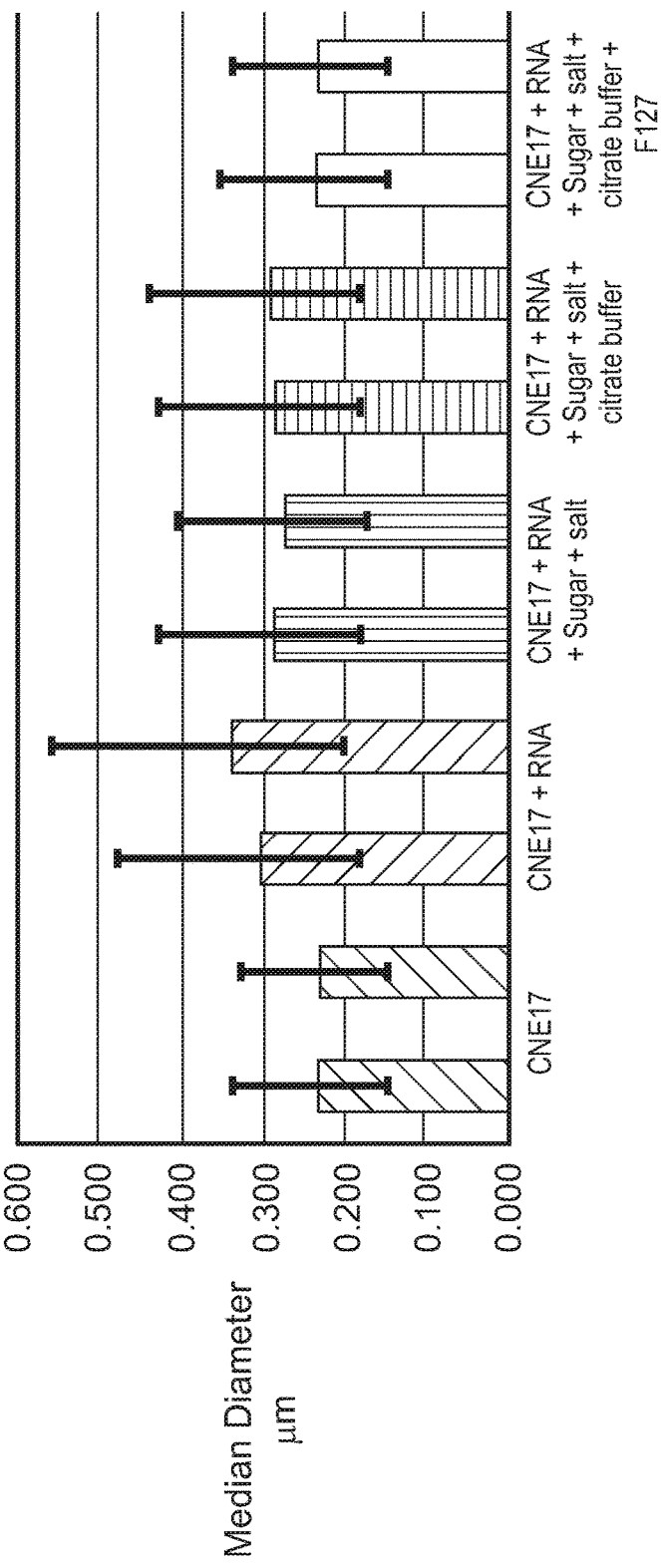

This invention generally relates to cationic oil-in-water emulsions in which a nucleic acid molecule is complexed to the emulsion particles, the emulsion particles have an average diameter of about 80 nm to about 180 nm, and the emulsion have an N/P ratio of at least 4:1. The emulsion particles comprise an oil core and a cationic lipid. The cationic lipid can interact with the negatively charged molecule thereby anchoring the molecule to the emulsion particles. The emulsions can be used to deliver nucleic acide molecules, such as an RNA molecule to cells.

The present invention is based on the discovery that an immune response that is raised against an antigen enconded by RNA, when a cationic oil-in-water emulsion that contains an RNA molecule encoding the antigen is administered to an individual, is affected by properties of the emulsion, including the average diameter of the emulsion particles and the amount of RNA that is complexed to the emulsion particles (i.e., N/P ratio). The inventors determined that the average diameter of emulsion particles increases when RNA molecules are complexed to the emulsion, and that large diameter particles result in lower neutralizing titers. Emulsions in which the average particle diameter is between about 80 nm and about 180 nm provide good neutralizing titers. Even within this range, emulsions with average particle sizes at the high end of the range are less preferred, and an average particle size of about 100 nm is particularly preferred. Also preferred is an average particle diameter between about 100 nm and about 130 nm. The inventors surprisingly discovered that the immune response does not have a direct linear relationship to the amount of RNA that is complexed to the emulsion. An N/P ratio of 4:1 produces a good immune response to the encoded antigen, but higher N/P ratios do not necessarily result in higher neutralizing titers.

The average diameter of cationic oil-in-water emulsion particles increases when RNA molecules are complexed to the emulsion. This effect can be reduced by the inclusion of inorganic salts in the emulsion. However, inorganic salts can inhibit the binding of nucleic acid molecules to the emulsion particles, therefore, the inorganic salt(s) should be present in only low concentrations (e.g., no more than about 30 mM). If desired, hydrophilic polymers can be used to reduce the particle size increase caused by nucleic acid complexation. Again, hydrophilic polymers can inhibit binding of nucleic acid molecules to the emulsion particles, therefore, hydrophilic polymer(s) should be present in only low concentrations (e.g., about 0.05% to about 20% (w/v)).

Cationic oil-in-water emulsions that contain an RNA molecule encoding the antigen can be administered to an individual to induce an immune response to the encoded antigen. When the cationic oil-in-water emulsions are used for this purpose, it is preferred that they are isotonic. However, because inorganic salts can inhibit the binding of nucleic acid molecules to the emulsion particles, tonicity is preferably adjusted with a nonionic tonicifying agent. In preferred embodiments, the cationic oil-in-water emulsions that contain an RNA molecule are adjusted to 250 mOsm/kg water to about 320 mOsm/kg using a sugar, sugar alcohol or combination thereof.

2. Definitions

As used herein, the singular forms "a," "an" and "the" include plural references unless the content clearly dictates otherwise.

The term "about" as used here, refers to +/−10% of a value.

The term "surfactant" is a term of art and generally refers to any molecule having both a hydrophilic group (e.g., a polar group), which energetically prefers solvation by water, and a hydrophobic group which is not well solvated by water. The term "nonionic surfactant" is a known term in the art and generally refers to a surfactant molecule whose hydrophilic group (e.g., polar group) is not electrostatically charged.

The term "polymer" refers to a molecule consisting of individual chemical moieties, which may be the same or different, that are joined together. As used herein, the term "polymer" refers to individual chemical moieties that are joined end-to-end to form a linear molecule, as well as individual chemical moieties joined together in the form of a branched (e.g., a "multi-arm" or "star-shaped") structure. Exemplary polymers include, e.g., poloxamers. Poloxamers are nonionic triblock copolymers having a central hydrophobic chain of polyoxypropylene (poly(propylene oxide)) flanked by two hydrophilic chains of polyoxyethylene (poly (ethylene oxide)).

A "buffer" refers to an aqueous solution that resists changes in the pH of the solution.

As used herein, "nucleotide analog" or "modified nucleotide" refers to a nucleotide that contains one or more chemical modifications (e.g., substitutions) in or on the nitrogenous base of the nucleoside (e.g., cytosine (C), thymine (T) or uracil (U)), adenine (A) or guanine (G)). A nucleotide analog can contain further chemical modifications in or on the sugar moiety of the nucleoside (e.g., ribose, deoxyribose, modified ribose, modified deoxyribose, six-membered sugar analog, or open-chain sugar analog), or the phosphate.

As use herein, "saccharide" encompasses monosaccharides, oligosaccharides, or polysaccharides in straight chain or ring forms, or a combination thereof to form a saccharide chain. Oligosaccharides are saccharides having two or more monosaccharide residues. Examples of saccharides include glucose, maltose, maltotriose, maltotetraose, sucrose and trehalose.

The terms "self-replicating RNA," "RNA replicon" or "RNA vector" is a term of art and generally refer to an RNA molecule which is capable of directing its own amplification or self-replication in vivo, typically within a target cell. The RNA replicon is used directly, without the requirement for introduction of DNA into a cell and transport to the nucleus where transcription would occur. By using the RNA vector for direct delivery into the cytoplasm of the host cell, autonomous replication and translation of the heterologous nucleic acid sequence occurs efficiently. An alphavirus-derived self-replicating RNA may contain the following elements in sequential order: 5' viral sequences required in cis for replication (also referred to as 5' CSE, in background), sequences which, when expressed, code for biologically active alphavirus nonstructural proteins (e.g., nsP1, nsP2, nsP3, nsP4), 3' viral sequences required in cis for replication (also referred to as 3' CSE, in background), and a polyadenylate tract. The alphavirus-derived self-replicating RNA may also contain a viral subgenomic "junction region" promoter, sequences from one or more structural protein genes or portions thereof, extraneous nucleic acid molecule(s) which are of a size sufficient to allow production of recombinant alphavirus particles, as well as heterologous sequence(s) to be expressed.

The term "adjuvant" refers to any substance that assists or modifies the action of a pharmaceutical, including but not limited to immunological adjuvants, which increase and/or diversify the immune response to an antigen. Hence, immunological adjuvants include compounds that are capable of potentiating an immune response to antigens. Immunological adjuvants can potentiate humoral and/or cellular immunity. Substances that stimulate an innate immune response are included within the definition of immunological adjuvants herein. Immunological adjuvants may also be referred to as "immunopotentiators."

As used herein, an "antigen" refers to a molecule containing one or more epitopes (e.g., linear, conformational or both). As used herein, an "epitope" is that portion of given species (e.g., an antigenic molecule or antigenic complex) that determines its immunological specificity. An epitope is within the scope of the present definition of antigen. The term "antigen" as used herein includes subunit antigens, i.e., antigens which are separate and discrete from a whole organism with which the antigen is associated in nature.

An "immunological response" or "immune response" is the development in a subject of a humoral and/or a cellular immune response to an antigen or an immunological adjuvant.

Immune responses include innate and adaptive immune responses. Innate immune responses are fast-acting responses that provide a first line of defense for the immune system. In contrast, adaptive immunity uses selection and clonal expansion of immune cells having somatically rearranged receptor genes (e.g., T- and B-cell receptors) that recognize antigens from a given pathogen or disorder (e.g., a tumor), thereby providing specificity and immunological memory. Innate immune responses, among their many effects, lead to a rapid burst of inflammatory cytokines and activation of antigen-presenting cells (APCs) such as macrophages and dendritic cells. To distinguish pathogens from self-components, the innate immune system uses a variety of relatively invariable receptors that detect signatures from pathogens, known as pathogen-associated molecular patterns, or PAMPs. The addition of microbial components to experimental vaccines is known to lead to the development of robust and durable adaptive immune responses. The mechanism behind this potentiation of the immune responses has been reported to involve pattern-recognition receptors (PRRs), which are differentially expressed on a variety of immune cells, including neutrophils, macrophages, dendritic cells, natural killer cells, B cells and some nonimmune cells such as epithelial and endothelial cells. Engagement of PRRs leads to the activation of some of these cells and their secretion of cytokines and chemokines, as well as maturation and migration of other cells. In tandem, this creates an inflammatory environment that leads to the establishment of the adaptive immune response. PRRs include nonphagocytic receptors, such as Toll-like receptors (TLRs) and nucleotide-binding oligomerization domain (NOD) proteins, and receptors that induce phagocytosis, such as scavenger receptors, mannose receptors and β-glucan receptors. Reported TLRs (along with examples of some reported ligands, which may be used as immunogenic molecule in various embodiments of the invention) include the following: TLR1 (bacterial lipoproteins from Mycobacteria, Neisseria), TLR2 (zymosan yeast particles, peptidoglycan, lipoproteins, lipopeptides, glycolipids, lipopolysaccharide), TLR3 (viral double-stranded RNA, poly:IC), TLR4 (bacterial lipopolysaccharides, plant product taxol), TLR5 (bacterial flagellins), TLR6 (yeast zymosan particles, lipotechoic acid, lipopeptides from mycoplasma), TLR7 (single-stranded RNA, imiquimod, resimiquimod, and other synthetic compounds such as loxoribine and bropirimine), TLR8 (single-stranded RNA, resimiquimod) and TLR9 (CpG oligonucleotides), among others. Dendritic cells are recognized as some of the most important cell types for initiating the priming of naive CD4$^+$ helper T ($T_H$) cells and for inducing CD8$^+$ T cell differentiation into killer cells. TLR signaling has been reported to play an important role in determining the quality of these helper T cell responses, for instance, with the nature of the TLR signal determining the specific type of $T_H$ response that is observed (e.g., $T_H1$ versus $T_H2$ response). A combination of antibody (humoral) and cellular immunity are produced as part of a $T_H1$-type response, whereas a $T_H2$-type response is predominantly an antibody response. Various TLR ligands such as CpG DNA (TLR9) and imidazoquinolines (TLR7, TLR8) have been documented to stimulate cytokine production from immune cells in vitro. The imidazoquinolines are the first small, drug-like compounds shown to be TLR agonists. For further information, see, e.g., A. Pashine, N. M. Valiante and J. B. Ulmer, Nature Medicine 11, S63-S68 (2005), K. S. Rosenthal and D. H. Zimmerman, Clinical and Vaccine Immunology, 13(8), 821-829 (2006), and the references cited therein.

For purposes of the present invention, a humoral immune response refers to an immune response mediated by antibody molecules, while a cellular immune response is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from $CD4^+$ and $CD8^+$ T-cells.

A composition such as an immunogenic composition or a vaccine that elicits a cellular immune response may thus serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host. The ability of a particular antigen or composition to stimulate a cell-mediated immunological response may be determined by a number of assays known in the art, such as by lymphoproliferation (lymphocyte activation) assays, CTL cytotoxic cell assays, by assaying for T-lymphocytes specific for the antigen in a sensitized subject, or by measurement of cytokine production by T cells in response to restimulation with antigen. Such assays are well known in the art. See, e.g., Erickson et al. (1993) J. Immunol 151:4189-4199; Doe et al. (1994) Eur. J. Immunol 24:2369-2376. Thus, an immunological response as used herein may be one which stimulates the production of CTLs and/or the production or activation of helper T-cells. The antigen of interest may also elicit an antibody-mediated immune response. Hence, an immunological response may include, for example, one or more of the following effects among others: the production of antibodies by, for example, B-cells; and/or the activation of suppressor T-cells and/or γδ T-cells directed specifically to an antigen or antigens present in the composition or vaccine of interest. These responses may serve, for example, to neutralize infectivity, and/or mediate antibody-complement, or antibody dependent cell cytotoxicity (ADCC) to provide protection to an immunized host. Such responses can be determined using standard immunoassays and neutralization assays, well known in the art.

Compositions in accordance with the present invention display "enhanced immunogenicity" for a given antigen when they possess a greater capacity to elicit an immune response than the immune response elicited by an equivalent amount of the antigen in a differing composition (e.g., wherein the antigen is administered as a soluble protein). Thus, a composition may display enhanced immunogenicity, for example, because the composition generates a stronger immune response, or because a lower dose or fewer doses of antigen is necessary to achieve an immune response in the subject to which it is administered. Such enhanced immunogenicity can be determined, for example, by administering a composition of the invention and an antigen control to animals and comparing assay results of the two.

3. Cationic Oil-in-Water Emulsions

The cationic oil-in-water emulsions disclosed herein are generally described in the manner that is conventional in the art, by concentrations of components that are used to prepare the emulsions. It is understood in the art that during the process of producing emulsions, including sterilization and other downstream processes, small amounts of oil (e.g., squalene), cationic lipid (e.g., DOTAP), or other components may be lost, and the actual concentrations of these components in the final product (e.g., a packaged, sterilized emulsion that is ready for administration) might be slightly lower than starting amounts, sometimes by up to about 10% or by up to about 20%.

The cationic oil-in-water emulsion particles comprise an oil core and a cationic lipid. The cationic lipid can interact with the nucleic acid molecule, for example through electrostatic forces and hydrophobic/hydrophilic interactions, thereby anchoring the nucleic acid molecule to the emulsion particles. The cationic emulsions described herein are particularly suitable for delivering a nucleic acid molecule, such as an RNA molecule encoding an antigen or small interfering RNA to cells in vivo. For example, the cationic emulsions described herein provide advantages for delivering RNA that encode antigens, including self-replicating RNAs, as vaccines.

The particles of the oil-in-water emulsions likely resemble a micelle with a central core of oil. The oil core is coated with the cationic lipid, which disperses the oil droplet in the aqueous (continuous) phase as micelle-like droplets. One or more optional components may be present in the emulsion, such as surfactants and/or phospholipids as described below. For example, one or more surfactants may be used to promote particle formation and/or to stabilize the emulsion particles. In that case, the oil core is coated with the cationic lipid as well as the surfactant(s) to form micelle-like droplets. Similarly, one or more lipids (e.g., neutral lipids, glycol-lipids or phospholipids) may also be present on the surface of the emulsion particles, if such lipids are used as emulsifiers to disperse the oil droplets.

The particles of the oil-in-water emulsions have an average diameter (i.e., average number diameter) of about 80 nm to about 180 nm, from about 80 nm to 150 nm, from about 80 nm to 130 nm, or from about 80 nm to 120 nm. Particularly preferred average particle diameter is about 100 nm.

The size of the emulsion particles can be varied by changing the ratio of surfactant to oil (increasing the ratio decreases droplet size), operating pressure of homogenization (increasing operating pressure of homogenization typically reduces droplet size), temperature (increasing temperature decreases droplet size), changing the type of oil, increasing the number of passes through the microfluidizer, and other process parameters, as described herein. Inclusion of certain types of buffers in the aqueous phase may also affect the particle size.

The emulsion particles described herein can be complexed with a nucleic acid molecule, as described in further detail herein. In general, a cationic oil-in-water emulsion is combined with an aqueous solution that contains one or more species of nucleic acid molecules to form the emulsion that contains a nucleic acid molecule that is complexed to the emulsion particles. The aqueous solution that contains the nucleic acid molecule(s) contains a concentration of nucleic acids that will result in a complexed emulsion that has an N/P ratio of at least 4:1, for example from 4:1 to 20:1 or from 4:1 to 15:1. This can easily be accomplished because the the amount of nitrogen (N) in the emulsion can be quantified using any suitable method, such as the HPLC method used to quantify DOTAP described herein. Then, an aqueous solution of nucleic acid molecules can be prepared that contains an amount of nucleic acid sufficient to provide the amount of phosphates (P) needed to achieve the desired N/P ratio.

An exemplary cationic emulsion of the invention is CNE17. The oil core of CNE17 is squalene (at 4.3% w/v) and the cationic lipid is DOTAP (at 1.4 mg/mL). CNE17 also includes the surfactants SPAN85 ((sorbtian trioleate) at 0.5% v/v) and Tween 80 ((polysorbate 80; polyoxyethylenesorbitan monooleate) at 0.5% v/v). Thus, the particles of CNE17 comprise a squalene core coated with SPAN85, Tween80, and DOTAP. RNA molecules were shown to complex with CNE17 particles efficiently at 4:1 N/P ratio and 10:1 N/P ratio. Another exemplary cationic emulsion of the invention is referred herein as "CMF32." The oil of CMF32 is squalene (at 4.3% w/v) and the cationic lipid is DOTAP (at 3.2 mg/mL). CMF32 also includes the surfactants SPAN85 (sorbitan trioleate at 0.5% v/v) and Tween 80 (polysorbate 80; polyoxyethylenesorbitan monooleate; at 0.5% v/v). Thus, emulsion particles of CMF32 comprise squalene, SPAN85, Tween80, and DOTAP. RNA molecules were shown to complex with CMF32 particles efficiently at 4:1, 6:1, 8:1, 10:1, 12:1, and 14:1 N/P ratios. Other exemplary cationic emulsions include, e.g., the emulsions referred to herein as "CMF34" (4.3% w/v squalene, 0.5% Tween 80, 0.5% SPAN85, and 4.4 mg/mL DOTAP), "CMF35" (4.3% w/v squalene, 0.5% Tween 80, 0.5% SPAN85, 5.0 mg/mL DOTAP), and other emulsions described herein.

A particular cationic oil-in-water emulsion of the invention comprises DOTAP and squalene at concentrations of 2.1 mg/ml to 2.84 mg/ml (preferably 2.23 mg/ml to 2.71 mg/ml), and 30.92 mg/ml to 41.92 mg/ml (preferably 32.82 mg/ml to about 40.02 mg/ml), respectively, and further comprise equal amounts of SPAN85 and Tween80 (e.g., about 0.5% each). Another particular cationic oil-in-water emulsion of the invention comprises DOTAP and squalene at concentrations of 2.78 mg/ml to 3.76 mg/ml (preferably 2.94 mg/ml to 3.6 mg/ml), and 18.6 mg/ml to 25.16 mg/ml (preferably 19.69 mg/ml to about 24.07 mg/ml), respectively, and further comprise equal amounts of SPAN85 and Tween80 (e.g., about 0.5% each). Preferably, the particles of these emulsions have an average diameter from about 80 nm to about 180 nm.

The individual components of the oil-in-water emulsions of the present invention are known in the art, although such compositions have not been combined in the manner described herein. Accordingly, the individual components, although described below both generally and in some-detail for preferred embodiments, are well known in the art, and the terms used herein, such as oil core, surfactant, phospholipids, etc., are sufficiently well known to one skilled in the art without further description. In addition, while preferred ranges of the amount of the individual components of the emulsions are provided, the actual ratios of the components of a particular emulsion may need to be adjusted such that emulsion particles of desired size and physical property can be properly formed. For example, if a particular amount of oil is used (e.g. 5% v/v oil), then, the amount of surfactant should be at level that is sufficient to disperse the oil droplet into aqueous phase to form a stable emulsion. The actual amount of surfactant required to disperse the oil droplet into aqueous phase depends on the type of surfactant and the type of oil core used for the emulsion; and the amount of oil may also vary according to droplet size (as this changes the surface area between the two phases). The actual amounts and the relative proportions of the components of a desired emulsion can be readily determined by a skilled artisan.

A. Oil Core

The particles of the cationic oil-in-water emulsions comprise an oil core.

The oil preferably is in the liquid phase at 1° C. or above, and is immiscible to water.

Preferably, the oil is a metabolizable, non-toxic oil; more preferably one of about 6 to about 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil that can be metabolized by the body of the subject to which the emulsion will be administered, and is not toxic to the subject. The subject may be an animal, typically a mammal, and preferably a human.

In certain embodiments, the oil core is in liquid phase at 25° C. The oil core is in liquid phase at 25° C., when it displays the properties of a fluid (as distinguished from solid and gas; and having a definite volume but no definite shape) when stored at 25° C. The emulsion, however, may be stored and used at any suitable temperature. Preferably, the oil core is in liquid phase at 4° C.

The oil may be any long chain alkane, alkene or alkyne, or an acid or alcohol derivative thereof either as the free acid, its salt or an ester such as a mono-, or di- or triester, such as the triglycerides and esters of 1,2-propanediol or similar poly-hydroxy alcohols. Alcohols may be acylated employing a mono- or poly-functional acid, for example acetic acid, propanoic acid, citric acid or the like. Ethers derived from long chain alcohols which are oils and meet the other criteria set forth herein may also be used.

The individual alkane, alkene or alkyne moiety and its acid or alcohol derivatives will generally have from about 6 to about 30 carbon atoms. The moiety may have a straight or branched chain structure. It may be fully saturated or have one or more double or triple bonds. Where mono or poly ester- or ether-based oils are employed, the limitation of about 6 to about 30 carbons applies to the individual fatty acid or fatty alcohol moieties, not the total carbon count.

It is particularly desirable that the oil can be metabolized by the host to which the emulsion is administered.

Any suitable oils from an animal, fish or vegetable source may be used. Sources for vegetable oils include nuts, seeds and grains, and suitable oils, such as, peanut oil, soybean oil, coconut oil, and olive oil and the like. Other suitable seed oils include safflower oil, cottonseed oil, sunflower seed oil, sesame seed oil and the like. In the grain group, corn oil, and the oil of other cereal grains such as wheat, oats, rye, rice, teff, triticale and the like may also be used. The technology for obtaining vegetable oils is well developed and well known. The compositions of these and other similar oils may be found in, for example, the Merck Index, and source materials on foods, nutrition and food technology.

About six to about ten carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEES from PVO International, Inc., Chemical Specialties Division, 416 Division Street, Boongon, N.J. and others.

Animal oils and fats are often in solid phase at physiological temperatures due to the fact that they exist as triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Squalene (2,6,10,15,19,23-hexamethyl-2,6,10,14,18,22-tetracosahexaene), a branched, unsaturated terpenoid, is particularly preferred herein. A major source of squalene is shark liver oil, although plant oils (primarily vegetable oils), including amaranth seed, rice bran, wheat germ, and olive oils, are also suitable sources. Squalene can also be obtained from yeast or other suitable microbes. In some embodiments, Squalene is preferably obtained from non-animal sources, such as from olives, olive oil or yeast. Squalane, the saturated analog to squalene, is also preferred. Fish oils, including squalene and squalane, are readily available from commercial sources or may be obtained by methods known in the art.

In certain embodiments, the oil core comprises an oil that is selected from the group consisting of: Castor oil, Coconut oil, Corn oil, Cottonseed oil, Evening primrose oil, Fish oil, Jojoba oil, Lard oil, Linseed oil, Olive oil, Peanut oil, Safflower oil, Sesame oil, Soybean oil, Squalene, Squalane, Sunflower oil, Wheatgerm oil, and Mineral oil. In exemplary embodiments, the oil core comprises Soybean oil, Sunflower oil, Olive oil, Squalene, Squalane or a combination thereof. Squalane can also be used as the oil. In exemplary embodiments, the oil core comprises Squalene, Squalane, or a combination thereof.

The oil component of the emulsion may be present in an amount from about 0.2% to about 20% (v/v). For example, the cationic oil-in-water emulsion may comprise from about 0.2% to about 20% (v/v) oil, from about 0.2% to about 15% (v/v) oil, from about 0.2% to about 10% (v/v) oil, from about 0.2% to about 9% (v/v) oil, from about 0.2% to about 8% (v/v) oil, from about 0.2% to about 7% (v/v) oil, from about 0.2% to about 6% (v/v) oil, from about 0.2% to about 5% (v/v) oil, from about 0.2% to about 4.3% (v/v) oil, from about 0.3% to about 20% (v/v) oil, from about 0.4% to about 20% (v/v) oil, from about 0.5% to about 20% (v/v) oil, from about 1% to about 20% (v/v) oil, from about 2% to about 20% (v/v) oil, from about 3% to about 20% (v/v) oil, from about 4% to about 20% (v/v) oil, from about 4.3% to about 20% (v/v) oil, from about 5% to about 20% (v/v) oil, about 0.5% (v/v) oil, about 1% (v/v) oil, about 1.5% (v/v) oil, about 2% (v/v) oil, about 2.5% (v/v) oil, about 3% (v/v) oil, about 3.5% (v/v) oil, about 4% (v/v) oil, about 4.3% (v/v) oil, about 5% (v/v) oil, or about 10% (v/v) oil.

Alternatively, the cationic oil-in-water emulsion may comprise from about 0.2% to about 10% (w/v) oil, from about 0.2% to about 9% (w/v) oil, from about 0.2% to about 8% (w/v) oil, from about 0.2% to about 7% (w/v) oil, from about 0.2% to about 6% (w/v) oil, from about 0.2% to about 5% (w/v) oil, from about 0.2% to about 4.3% (w/v) oil, or about 4.3% (w/v) oil.

In an exemplary embodiment, the cationic oil-in-water emulsion comprises about 0.5% (v/v) oil. In another exemplary embodiment, the cationic oil-in-water emulsion comprises about 4.3% (v/v) oil. In another exemplary embodiment, the cationic oil-in-water emulsion comprises about 5% (v/v) oil. In another exemplary embodiment, the cationic oil-in-water emulsion comprises about 4.3% (w/v) squalene.

As noted above, the percentage of oil described above is determined based on the initial amount of the oil that is used to prepare the emulsions. It is understood in the art that the actual concentration of the oil in the final product (e.g., a packaged, sterilized emulsion that is ready for administration) might be slightly lower, sometimes up to about 10% or about 20%.

B. Cationic Lipids

The emulsion particles described herein comprise a cationic lipid, which can interact with the negatively charged molecule thereby anchoring the molecule to the emulsion particles.

The cationic lipid can have a positive charge at about 12 pH, about 11 pH, about 10 pH, about 9 pH, about 8 pH, about 7 pH, or about 6 pH.

Any suitable cationic lipid may be used. Generally, the cationic lipid contains a nitrogen atom that is positively charged under physiological conditions. Suitable cationic lipids include, benzalkonium chloride (BAK), benzethonium chloride, cetrimide (which contains tetradecyltrimethylammonium bromide and possibly small amounts of dodecyltrimethylammonium bromide and hexadecyltrimethyl ammonium bromide), cetylpyridinium chloride (CPC), cetyl trimethylammonium chloride (CTAC), primary amines, secondary amines, tertiary amines, including but not limited to N,N',N'-polyoxyethylene (10)-N-tallow-1,3-diaminopropane, other quaternary amine salts, including but not limited to dodecyltrimethylammonium bromide, hexadecyltrimethyl-ammonium bromide, mixed alkyl-trimethyl-ammonium bromide, benzyldimethyldodecylammonium chloride, benzyldimethylhexadecyl-ammonium chloride, benzyltrimethylammonium methoxide, cetyldimethylethylammonium bromide, dimethyldioctadecyl ammonium bromide (DDAB), methylbenzethonium chloride, decamethonium chloride, methyl mixed trialkyl ammonium chloride, methyl trioctylammonium chloride), N,N-dimethyl-N-[2 (2-methyl-4-(1,1,3,3tetramethylbutyl)-phenoxy]-ethoxy)ethyl]-benzenemetha-naminium chloride (DEBDA), dialkyldimetylammonium salts, [1-(2,3-dioleyloxy)-propyl]-N,N,N, trimethylammonium chloride, 1,2-diacyl-3-(trimethylammonio) propane (acyl group=dimyristoyl, dipalmitoyl, distearoyl, dioleoyl), 1,2-diacyl-3 (dimethylammonio)propane (acyl group=dimyristoyl, dipalmitoyl, distearoyl, dioleoyl), 1,2-dioleoyl-3-(4'-trimethyl-ammonio) butanoyl-sn-glycerol, 1,2-dioleoyl 3-succinyl-sn-glycerol choline ester, cholesteryl (4'-trimethylammonio) butanoate), N-alkyl pyridinium salts (e.g. cetylpyridinium bromide and cetylpyridinium chloride), N-alkylpiperidinium salts, dicationic bolaform electrolytes ($C_{12}Me_6$; $C_{12}Bu_6$), dialkylglycetylphosphorylcholine, lysolecithin, L-α dioleoylphosphatidylethanolamine, cholesterol hemisuccinate choline ester, lipopolyamines, including but not limited to dioctadecylamidoglycylspermine (DOGS), dipalmitoyl phosphatidylethanol-amidospermine (DPPES), lipopoly-L (or D)-lysine (LPLL, LPDL), poly (L or D)-lysine conjugated to N-glutarylphosphatidylethanolamine, didodecyl glutamate ester with pendant amino group ($C_{12}GluPhC_nN^+$), ditetradecyl glutamate ester with pendant amino group ($C_{14}GluC_nN^+$), cationic derivatives of cholesterol, including but not limited to cholesteryl-3 β-oxysuccinamidoethylenetrimethylammonium salt, cholesteryl-3 β-oxysuccinamidoethylenedimethylamine, cholesteryl-3 β-carboxyamidoethylenetrimethylammonium salt, cholesteryl-3 β-carboxyamidoethylenedimethylamine, and 3γ-[N—(N',N-dimethylaminoetanecarbomoyl]cholesterol) (DC-Cholesterol), 1,2-dioleoyloxy-3-(trimethylammonio)propane (DOTAP), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), and combination thereof.

Other cationic lipids suitable for use in the invention include, e.g., the cationic lipids described in U.S. Patent Publications 2008/0085870 (published Apr. 10, 2008) and 2008/0057080 (published Mar. 6, 2008).

Other cationic lipids suitable for use in the invention include, e.g., Lipids E0001-E0118 or E0119-E0180 as disclosed in Table 6 (pages 112-139) of WO 2011/076807 (which also discloses methods of making, and method of using these cationic lipids). Additional suitable cationic lipids include N-[1-(2, 3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA).

The emulsion may comprise any combination of two or more of the cationic lipids described herein.

In some embodiments, the cationic lipid contains a quaternary amine.

In preferred embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), Lipids E0001-E0118 or E0119-E0180 as disclosed in Table 6 (pages 112-139) of WO 2011/076807, and combinations thereof.

In other preferred embodiments, the cationic lipid is selected from the group consisting of 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), Lipids E0001-E0118 or E0119-E0180 as disclosed in Table 6 (pages 112-139) of WO 2011/076807 (incorporated herein by reference), and combinations thereof.

In certain embodiments, the cationic lipid is DOTAP. The cationic oil-in-water emulsion may comprise from about 0.5 mg/ml to about 25 mg/ml DOTAP. For example, the cationic oil-in-water emulsion may comprise DOTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 12 mg/ml, about 18 mg/ml, about 20 mg/ml, about 21.8 mg/ml, about 24 mg/ml, etc.

In an exemplary embodiment, the cationic oil-in-water emulsion comprises from about 0.8 mg/ml to about 1.6 mg/ml DOTAP, such as 0.8 mg/ml, 1.2 mg/ml, 1.4 mg/ml or 1.6 mg/ml.

In certain embodiments, the cationic lipid is DC Cholesterol. The cationic oil-in-water emulsion may comprise DC Cholesterol at from about 0.1 mg/ml to about 5 mg/ml DC Cholesterol. For example, the cationic oil-in-water emulsion may comprise DC Cholesterol from about 0.1 mg/ml to about 5 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.62 mg/ml to about 5 mg/ml, from about 1 mg/ml to about 5 mg/ml, from about 1.5 mg/ml to about 5 mg/ml, from about 2 mg/ml to about 5 mg/ml, from about 2.46 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, from about 0.1 mg/ml to about 4.92 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.46 mg/ml, from about 0.1 mg/ml to about 2 mg/ml, from about 0.1 mg/ml to about 1.5 mg/ml, from about 0.1 mg/ml to about 1 mg/ml, from about 0.1 mg/ml to about 0.62 mg/ml, about 0.15 mg/ml, about 0.3 mg/ml, about 0.6 mg/ml, about 0.62 mg/ml, about 0.9 mg/ml, about 1.2 mg/ml, about 2.46 mg/ml, about 4.92 mg/ml, etc.

In an exemplary embodiment, the cationic oil-in-water emulsion comprises from about 0.62 mg/ml to about 4.92 mg/ml DC Cholesterol, such as 2.46 mg/ml.

In certain embodiments, the cationic lipid is DDA. The cationic oil-in-water emulsion may comprise from about 0.1 mg/ml to about 5 mg/ml DDA. For example, the cationic oil-in-water emulsion may comprise DDA at from about 0.1 mg/ml to about 5 mg/ml, from about 0.1 mg/ml to about 4.5 mg/ml, from about 0.1 mg/ml to about 4 mg/ml, from about 0.1 mg/ml to about 3.5 mg/ml, from about 0.1 mg/ml to about 3 mg/ml, from about 0.1 mg/ml to about 2.5 mg/ml, from about 0.1 mg/ml to about 2 mg/ml, from about 0.1 mg/ml to about 1.5 mg/ml, from about 0.1 mg/ml to about 1.45 mg/ml, from about 0.2 mg/ml to about 5 mg/ml, from about 0.3 mg/ml to about 5 mg/ml, from about 0.4 mg/ml to about 5 mg/ml, from about 0.5 mg/ml to about 5 mg/ml, from about 0.6 mg/ml to about 5 mg/ml, from about 0.73 mg/ml to about 5 mg/ml, from about 0.8 mg/ml to about 5 mg/ml, from about 0.9 mg/ml to about 5 mg/ml, from about 1.0 mg/ml to about 5 mg/ml, from about 1.2 mg/ml to about 5 mg/ml, from about 1.45 mg/ml to about 5 mg/ml, from about 2 mg/ml to about 5 mg/ml, from about 2.5 mg/ml to about 5 mg/ml, from about 3 mg/ml to about 5 mg/ml, from about 3.5 mg/ml to about 5 mg/ml, from about 4 mg/ml to about 5 mg/ml, from about 4.5 mg/ml to about 5 mg/ml, about 1.2 mg/ml, about 1.45 mg/ml, etc. Alternatively, the cationic oil-in-water emulsion may comprise DDA at about 20 mg/ml, about 21 mg/ml, about 21.5 mg/ml, about 21.6 mg/ml, about 25 mg/ml.

In an exemplary embodiment, the cationic oil-in-water emulsion comprises from about 0.73 mg/ml to about 1.45 mg/ml DDA, such as 1.45 mg/ml.

In certain embodiments, the cationic lipid is DOTMA. The cationic oil-in-water emulsion may comprise from about 0.5 mg/ml to about 25 mg/ml DOTMA. For example, the cationic oil-in-water emulsion may comprise DOTMA at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.6 mg/ml, from about 0.7 mg/ml to about 1.6 mg/ml, from about 0.8 mg/ml to about 1.6 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.35 mg/ml, about 1.4 mg/ml, about 1.5 mg/ml, about 1.6 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DOTMA, such as 0.8 mg/ml, 1.2 mg/ml, 1.4 mg/ml or 1.6 mg/ml.

In certain embodiments, the cationic lipid is DOEPC. The cationic oil-in-water emulsion may comprise from about 0.5 mg/ml to about 25 mg/ml DOEPC. For example, the cationic oil-in-water emulsion may comprise DOEPC at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.8 mg/ml DOEPC, such as 0.8 mg/ml, 1.2 mg/ml, 1.4 mg/ml, 1.6 mg/ml, 1.7 mg/ml, or 1.8 mg/ml.

In certain embodiments, the cationic lipid is DSTAP. The cationic oil-in-water emulsion may comprise from about 0.5 mg/ml to about 50 mg/ml DSTAP. For example, the cationic oil-in-water emulsion may comprise DSTAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DSTAP, such as 0.8 mg/ml, 1.2 mg/ml, 1.4 mg/ml or 1.6 mg/ml.

In certain embodiments, the cationic lipid is DODAC. The cationic oil-in-water emulsion may comprise from about 0.5 mg/ml to about 50 mg/ml DODAC. For example, the cationic oil-in-water emulsion may comprise DODAC at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.15 mg/ml, about 1.16 mg/ml, about 1.17 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from 0.73 mg/ml to about 1.45 mg/ml DODAC, such as 1.45 mg/ml.

In certain embodiments, the cationic lipid is DODAP. The cationic oil-in-water emulsion may comprise from about 0.5 mg/ml to about 50 mg/ml DODAP. For example, the cationic oil-in-water emulsion may comprise DODAP at from about 0.5 mg/ml to about 25 mg/ml, from about 0.6 mg/ml to about 25 mg/ml, from about 0.7 mg/ml to about 25 mg/ml, from about 0.8 mg/ml to about 25 mg/ml, from about 0.9 mg/ml to about 25 mg/ml, from about 1.0 mg/ml to about 25 mg/ml, from about 1.1 mg/ml to about 25 mg/ml, from about 1.2 mg/ml to about 25 mg/ml, from about 1.3 mg/ml to about 25 mg/ml, from about 1.4 mg/ml to about 25 mg/ml, from about 1.5 mg/ml to about 25 mg/ml, from about 1.6 mg/ml to about 25 mg/ml, from about 1.7 mg/ml to about 25 mg/ml, from about 0.5 mg/ml to about 24 mg/ml, from about 0.5 mg/ml to about 22 mg/ml, from about 0.5 mg/ml to about 20 mg/ml, from about 0.5 mg/ml to about 18 mg/ml, from about 0.5 mg/ml to about 15 mg/ml, from about 0.5 mg/ml to about 12 mg/ml, from about 0.5 mg/ml to about 10 mg/ml, from about 0.5 mg/ml to about 5 mg/ml, from about 0.5 mg/ml to about 4 mg/ml, from about 0.5 mg/ml to about 3 mg/ml, from about 0.5 mg/ml to about 2 mg/ml, from about 0.5 mg/ml to about 1.9 mg/ml, from about 0.5 mg/ml to about 1.8 mg/ml, from about 0.5 mg/ml to about 1.7 mg/ml, from about 0.5 mg/ml to about 1.6 mg/ml, from about 0.6 mg/ml to about 1.7 mg/ml, from about 0.7 mg/ml to about 1.7 mg/ml, from about 0.8 mg/ml to about 1.7 mg/ml, from about 0.8 mg/ml to about 3.0 mg/ml, about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 12 mg/ml, about 18 mg/ml, about 20 mg/ml, about 22.5 mg/ml, about 25 mg/ml etc.

In an exemplary embodiment, the cationic oil-in-water emulsion comprises from about 0.8 mg/ml to about 1.6 mg/ml DODAP, such as 0.8 mg/ml, 1.2 mg/ml, 1.4 mg/ml or 1.6 mg/ml.

In some cases, it may be desirable to use a cationic lipid that is soluble in the oil core. For example, DOTAP, DOEPC, DODAC, and DOTMA are soluble in squalene or squalane. In other cases, it may be desirable to use a cationic lipid that is not soluble in the oil core. For example, DDA and DSTAP are not soluble in squalene. It is within the knowledge in the art to determine whether a particular lipid is soluble or insoluble in the oil and choose an appropriate oil and lipid combination accordingly. For example, solubility can be predicted based on the structures of the lipid and oil (e.g., the solubility of a lipid may be determined by the structure of its tail). For example, lipids having one or two unsaturated fatty acid chains (e.g., oleoyl tails), such as DOTAP, DOEPC, DODAC, DOTMA, are soluble in squalene or squalane; whereas lipids having saturated fatty acid chains (e.g., stearoyl tails) are not soluble in squalene. Alternatively, solubility can be determined according to the quantity of the lipid that dissolves in a given quantity of the oil to form a saturated solution.

As noted above, the concentration of a lipid described above is determined based on the initial amount of the lipid that is used to prepare the emulsions. It is understood in the art that the actual concentration of the oil in the final product (e.g., a packaged, sterilized emulsion that is ready for administration) might be slightly lower, sometimes by up to about 20%.

C. Additional Components

The cationic oil-in-water emulsions described herein may further comprise additional components. For example, the emulsions may comprise components that can promote particle formation, improve the complexation between the nucleic acid molecules and the cationic particles, or increase the stability of the nucleic acid molecule (e.g., to prevent degradation of an RNA molecule). If desired, the cationic oil-in-water emulsion can contain an antioxidant, such as citrate, ascorbate or salts thereof.

Surfactants

In certain embodiments, the particles of the cationic oil-in-water emulsion further comprise a surfactant.

A substantial number of surfactants have been used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long chain fatty-acid-derived compounds form a third substantial group of emulsifying and suspending agents which could be used in this invention.

Specific examples of suitable surfactants include the following:

1. Water-soluble soaps, such as the sodium, potassium, ammonium and alkanol-ammonium salts of higher fatty acids ($C_{10}$-$C_{22}$), in particular sodium and potassium tallow and coconut soaps.

2. Anionic synthetic non-soap surfactants, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole of a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of fatty acid amide of a methyl tauride; and sodium and potassium salts of $SO_3$-sulfonated $C_{10}$-$C_{24}$ α-olefins.

3. Nonionic synthetic surfactants made by the condensation of alkylene oxide groups with an organic hydrophobic compound. Typical hydrophobic groups include condensation products of propylene oxide with propylene glycol, alkyl phenols, condensation product of propylene oxide and ethylene diamine, aliphatic alcohols having 8 to 22 carbon atoms, and amides of fatty acids.

4. Nonionic surfactants, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263, issued Feb. 14, 1967, and include dimethyldodecylphosphine oxide and dimethyl-(2hydroxydodecyl) phosphine oxide.

5. Long chain sulfoxides, including those corresponding to the formula $R^1$—SO—$R^2$ wherein $R^1$ and $R^2$ are substituted or unsubstituted alkyl radicals, the former containing from about 10 to about 28 carbon atoms, whereas $R^2$ contains from 1 to 3 carbon atoms. Specific examples of these sulfoxides include dodecyl methyl sulfoxide and 3-hydroxy tridecyl methyl sulfoxide.

6. Ampholytic synthetic surfactants, such as sodium 3-dodecylaminopropionate and sodium 3-dodecylaminopropane sulfonate.

7. Zwitterionic synthetic surfactants, such as 3-(N,N-dimethyl-N-hexadecylammonio)propane-1-sulfonate and 3-(N,N-dimethyl-N-hexadecylammonio)-2-hydroxy propane-1-sulfonate.

Additionally, all of the following types of surfactants can be used in a composition of the present invention: (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; and (h) fatty acyl diethanol amides. Since surfactants can be classified in more than one manner, a number of classes of surfactants set forth in this paragraph overlap with previously described surfactant classes.

There are a number of surfactants specifically designed for and commonly used in biological situations. Such surfactants are divided into four basic types: anionic, cationic, zwitterionic (amphoteric), and nonionic. Exemplary anionic surfactants include, e.g., perfluorooctanoate (PFOA or PFO), perfluorooctanesulfonate (PFOS), alkyl sulfate salts such as sodium dodecyl sulfate (SDS) or ammonium lauryl sulfate, sodium laureth sulfate (also known as sodium lauryl ether sulfate, SLES), alkyl benzene sulfonate, and fatty acid salts. Exemplary cationic surfactants include, e.g., alkyltrimethylammonium salts such as cetyl trimethylammonium bromide (CTAB, or hexadecyl trimethyl ammonium bromide), cetylpyridinium chloride (CPC), polyethoxylated tallow amine (POEA), benzalkonium chloride (BAC), benzethonium chloride (BZT). Exemplary zwitterionic (amphoteric) surfactants include, e.g., dodecyl betaine, cocamidopropyl betaine, and coco ampho glycinate. Exemplary nonionic surfactants include, e.g., alkyl poly(ethylene oxide), alkylphenol poly(ethylene oxide), copolymers of poly(ethylene oxide) and poly(propylene oxide) (commercially called poloxamers or poloxamines), Aayl polyglucosides (e.g., octyl glucoside or decyl maltoside), fatty alcohols (e.g., cetyl alcohol or oleyl alcohol), cocamide MEA, cocamide DEA, Pluronic® F-68 (polyoxyethylene-polyoxypropylene block copolymer), and polysorbates, such as Tween 20 (polysorbate 20), Tween 80 (polysorbate 80; polyoxyethylenesorbitan monooleate), dodecyl dimethylamine oxide, and vitamin E tocopherol propylene glycol succinate (Vitamin E TPGS).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants.

The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monoestearate, sorbitan monooleate, sorbitan sesquioleate, and sorbitan trioleate. These surfactants are commercially available under the name SPAN® or ARLACEL®, usually with a letter or number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have a hydrophilic-lipophilic balance (HLB) number between 1.8 to 8.6. Such surfactants can be readily made by means known in the art or are commercially available.

A related group of surfactants comprises olyoxyethylene sorbitan monoesters and olyoxyethylene sorbitan triesters. These materials are prepared by addition of ethylene oxide to a 1,4-sorbitan monester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monester or triester surfactants to promote emulsion stability. TWEEN® surfactants generally have a HLB value falling between 9.6 to 16.7. TWEEN® surfactants are commercially available.

A third group of non-ionic surfactants which could be used alone or in conjunction with SPAN®, ARLACEL® and TWEEN® surfactants are the polyoxyethylene fatty acids made by the reaction of ethylene oxide with a long-chain fatty acid. The most commonly available surfactant of this type is solid under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially.

A fourth group of polyoxyethylene based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from commercial sources.

Other non-ionic surfactants which could potentially be used are, for example, polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty glycerides, glycerol fatty acid esters or other polyoxyethylene acid alcohol or ether derivatives of long-chain fatty acids of 12-22 carbon atoms.

As the emulsions and formulations of the invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono, di- or triester based surfactant; a sorbitan ester polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

In certain embodiments, the emulsion comprises a single non-ionic surfactant, most particularly a TWEEN® surfactant, as the emulsion stabilizing non-ionic surfactant. In an exemplary embodiment, the emulsion comprises TWEEN® 80, otherwise known as polysorbate 80 or polyoxyethylene 20 sorbitan monooleate. In other embodiments, the emulsion comprises two or more non-ionic surfactants, in particular a TWEEN® surfactant and a SPAN® surfactant. In an exemplary embodiment, the emulsion comprises TWEEN® 80 and SPAN®85.

The oil-in-water emulsions can contain from about 0.01% to about 2.5% surfactant (v/v or w/v), about 0.01% to about 2% surfactant, 0.01% to about 1.5% surfactant, 0.01% to about 1% surfactant, 0.01% to about 0.5% surfactant, 0.05% to about 0.5% surfactant, 0.08% to about 0.5% surfactant, about 0.08% surfactant, about 0.1% surfactant, about 0.2% surfactant, about 0.3% surfactant, about 0.4% surfactant, about 0.5% surfactant, about 0.6% surfactant, about 0.7% surfactant, about 0.8% surfactant, about 0.9% surfactant, or about 1% surfactant.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% Tween 80 (polysorbate 80; polyoxyethylenesorbitan monooleate).

In an exemplary embodiment, the oil-in-water emulsion contains 0.08% Tween 80.

Alternatively or in addition, the oil-in-water emulsions can contain 0.05% to about 1%, 0.05% to about 0.9%, 0.05% to about 0.8%, 0.05% to about 0.7%, 0.05% to about 0.6%, 0.05% to about 0.5%, about 0.08%, about 0.1%, about 0.2%, about 0.3%, about 0.4%, about 0.5%, about 0.6%, about 0.7%, about 0.8%, about 0.9%, or about 1% SPAN85 (sorbtian trioleate).

Alternatively or in addition, the oil-in-water emulsions can contain a combination of surfactants described herein. For example, a combination of Tween 80 (polysorbate 80; polyoxyethylenesorbitan monooleate) and SPAN85 (sorbtian trioleate) may be used. The emulsions may contain various amounts Tween® 80 and SPAN85 (e.g., those exemplified above), including equal amounts of these surfactants. For example, the oil-in-water emulsions can contain about 0.05% Tween® 80 and about 0.05% SPAN®85, about 0.1% Tween® 80 and about 0.1% SPAN®85, about 0.2% Tween® 80 and about 0.2% SPAN®85, about 0.3% Tween® 80 and about 0.3% SPAN®85, about 0.4% Tween® 80 and about 0.4% SPAN®85, about 0.5% Tween® 80 and about 0.5% SPAN®85, about 0.6% Tween® 80 and about 0.6% SPAN®85, about 0.7% Tween® 80 and about 0.7% SPAN®85, about 0.8% Tween® 80 and about 0.8% SPAN®85, about 0.9% Tween® 80 and about 0.9% SPAN®85, or about 1% Tween® 80 and about 1.0% SPAN®85.

Polyethylene Glycol (PEG)-lipids, such as PEG coupled to dialkyloxypropyls (PEG-DAA), PEG coupled to diacylglycerol (PEG-DAG), PEG coupled to phosphatidylethanolamine (PE) (PEG-PE) or some other phospholipids (PEG-phospholipids), PEG conjugated to ceramides (PEG-Cer), or a combination thereof, may also be used as surfactants (see, e.g., U.S. Pat. No. 5,885,613; U.S. patent application publication Nos. 2003/0077829, 2005/0175682 and 2006/0025366). Other suitable PEG-lipids include, e.g., PEG-dialkyloxypropyl (DAA) lipids or PEG-diacylglycerol (DAG) lipids. Exemplary PEG-DAG lipids include, e.g., PEG-dilauroylglycerol ($C_{12}$) lipids, PEG-dimyristoylglycerol ($C_{14}$) lipids, PEG-dipalmitoylglycerol ($C_{16}$) lipids, or PEG-distearoylglycerol ($C_{18}$) lipids. Exemplary PEG-DAA lipids include, e.g., PEG-dilauryloxypropyl ($C_{12}$) lipids, PEG-dimyristyloxypropyl ($C_{14}$) lipids, PEG-dipalmityloxypropyl ($C_{16}$) lipids, or PEG-distearyloxypropyl ($C_{18}$) lipids.

PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. as well as other companies and include, for example, the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), and monomethoxypolyethylene glycol-imidazolyl-carbonyl (MePEG-IM). In addition, monomethoxypolyethyleneglycol-acetic acid (MePEG-CH$_2$COOH), is particularly useful for preparing the PEG-lipid conjugates including, e.g., PEG-DAA conjugates.

Preferably, the PEG has an average molecular weight of from about 1000 to about 5000 daltons (e.g., PEG$_{1000}$, PEG$_{2000}$, PEG$_{3000}$, PEG$_{4000}$, PEG$_{5000}$). The PEG can be optionally substituted by an alkyl, alkoxy, acyl or aryl group. PEG can be conjugated directly to the lipid or may be linked to the lipid via a linker moiety. Any linker moiety suitable for coupling the PEG to a lipid can be used including, e.g., non-ester containing linker moieties and ester-containing linker moieties In exemplary embodiments, PEG$_{2000}$PE, PEG$_{5000}$PE, PEG$_{1000}$DMG, PEG$_{2000}$DMG, PEG$_{3000}$DMG, or a combination thereof, is used as a surfactant. In certain exemplary embodiments, the oil-in-water emulsion contains from about 1 mg/ml to about 80 mg/ml PEG$_{2000}$PE, PEG$_{5000}$PE, PEG$_{1000}$DMG, PEG$_{2000}$DMG, or PEG$_{3000}$DMG.

Phospholipids

In certain embodiments, the particles of the cationic oil-in-water emulsion further comprise a phospholipid.

Phospholipids are esters of fatty acids in which the alcohol component of the molecule contains a phosphate group. Phospholipids include glycerophosphatides (containing glycerol) and the sphingomyelins (containing sphingosine). Exemplary phospholipids include phosphatidylcholine, phosphatidylethanolamine, phosphatidylserine and sphingomyelin; and synthetic phospholipids comprising dimyristoyl phosphatidylcholine, dipalmitoyl phosphatidylcholine, distearoyl phosphatidylcholine, distearoyl phosphatidylglycerol, dipalmitoyl phosphatidylglycerol, dimyristoyl phosphatidylserine, distearoyl phosphatidylserine, and dipalmitoyl serine.

The following exemplary phopholipids may be used.

| | |
|---|---|
| DDPC | 1,2-Didecanoyl-sn-Glycero-3-phosphatidylcholine |
| DEPA-NA | 1,2-Dierucoyl-sn-Glycero-3-Phosphate(Sodium Salt) |
| DEPC | 1,2-Erucoyl-sn-Glycero-3-phosphatidylcholine |
| DEPE | 1,2-Dierucoyl-sn-Glycero-3-phosphatidylethanolamine |
| DEPG-NA | 1,2-Dierucoyl-sn-Glycero-3[Phosphatidyl-rac-(1-glycerol. . .) |
| DLOPC | 1,2-Linoleoyl-sn-Glycero-3-phosphatidylcholine |
| DLPA-NA | 1,2-Dilauroyl-sn-Glycero-3-Phosphate(Sodium Salt) |
| DLPC | 1,2-Dilauroyl-sn-Glycero-3-phosphatidylcholine |
| DLPE | 1,2-Dilauroyl-sn-Glycero-3-phosphatidylethanolamine |
| DLPG-NA | 1,2-Dilauroyl-sn-Glycero-3[Phosphatidyl-rac-(1-glycerol. . .) (Sodium Salt) |
| DLPG-NH4 | 1,2-Dilauroyl-sn-Glycero-3[Phosphatidyl-rac-(1-glycerol. . .) |
| DLPS-NA | 1,2-Dilauroyl-sn-Glycero-3-phosphatidylserine(Sodium Salt) |
| DMPA-NA | 1,2-Diimyristoyl-sn-Glycero-3-Phosphate(Sodium Salt) |
| DMPC | 1,2-Dimyristoyl-sn-Glycero-3-phosphatidylcholine |
| DMPE | 1,2-Dimyristoyl-sn-Glycero-3-phosphatidylethanolamine |
| DMPG-NA | 1,2-Myristoyl-sn-Glycero-3[Phosphatidyl-rac-(1-glycerol. . .) |
| DMPG-NH4 | 1,2-Myristoyl-sn-Glycero-3[Phosphatidyl-rac-(1-glycerol. . .) |
| DMPG-NH4/NA | 1,2-Myristoyl-sn-Glycero-3[Phosphatidyl-rac-(1-glycerol. . .) |
| DMPS-NA | 1,2-Dimyristoyl-sn-Glycero-3-phosphatidylserine(Sodium Salt) |
| DOPA-NA | 1,2-Dioleoyl-sn-Glycero-3-Phosphate(Sodium Salt) |
| DOPC | 1,2-Dioleoyl-sn-Glycero-3-phosphatidylcholine |
| DOPE | 1,2-Dioleoyl-sn-Glycero-3-phosphatidylethanolamine |
| DOPG-NA | 1,2-Dioleoyl-sn-Glycero-3[Phosphatidyl-rac-(1-glycerol. . .) |
| DOPS-NA | 1,2-Dioleoyl-sn-Glycero-3-phosphatidylserine(Sodium Salt) |
| DPPA-NA | 1,2-Dipalmitoyl-sn-Glycero-3-Phosphate(Sodium Salt) |
| DPPC | 1,2-Dipalmitoyl-sn-Glycero-3-phosphatidylcholine |
| DPPE | 1,2-Dipalmitoyl-sn-Glycero-3-phosphatidylethanolamine |
| DPPG-NA | 1,2-Dipalmitoyl-sn-Glycero-3[Phosphatidyl-rac-(1-glycerol. . .) |
| DPPG-NH4 | 1,2-Dipalmitoyl-sn-Glycero-3[Phosphatidyl-rac-(1-glycerol. . .) |
| DPPS-NA | 1,2-Dipalmitoyl-sn-Glycero-3-phosphatidylserine(Sodium Salt) |
| DPyPE | 1,2-diphytanoyl-sn-glycero-3-phosphoethanolamine |
| DSPA-NA | 1,2-Distearoyl-sn-Glycero-3-Phosphate(Sodium Salt) |
| DSPC | 1,2-Distearoyl-sn-Glycero-3-phosphatidylcholine |
| DSPE | 1,2-Diostearpyl-sn-Glycero-3-phosphatidylethanolamine |
| DSPG-NA | 1,2-Distearoyl-sn-Glycero-3[Phosphatidyl-rac-(1-glycerol. . .) |
| DSPG-NH4 | 1,2-Distearoyl-sn-Glycero-3[Phosphatidyl-rac-(1-glycerol. . .) |
| DSPS-NA | 1,2-Distearoyl-sn-Glycero-3-phosphatidylserine(Sodium Salt) |
| EPC | Egg-PC |
| HEPC | Hydrogenated Egg PC |
| HSPC | High purity Hydrogenated Soy PC |
| HSPC | Hydrogenated Soy PC |
| LYSOPC MYRISTIC | 1-Myristoyl-sn-Glycero-3-phosphatidylcholine |
| LYSOPC PALMITIC | 1-Palmitoyl-sn-Glycero-3-phosphatidylcholine |
| LYSOPC STEARIC | 1-Stearoyl-sn-Glycero-3-phosphatidylcholine |
| Milk Sphingomyelin MPPC | 1-Myristoyl,2-palmitoyl-sn-Glycero 3-phosphatidylcholine |
| MSPC | 1-Myristoyl,2-stearoyl-sn-Glycero-3-phosphatidylcholine |
| PMPC | 1-Palmitoyl,2-myristoyl-sn-Glycero-3-phosphatidylcholine |
| POPC | 1-Palmitoyl,2-oleoyl-sn-Glycero-3-phosphatidylcholine |
| POPE | 1-Palmitoyl,2-oleoyl-sn-Glycero-3-phosphatidylethanolamine |
| POPG-NA | 1,2-Dioleoyl-sn-Glycero-3[Phosphatidyl-rac-(1-glycerol). . .](Sodium Salt) |
| PSPC | 1-Palmitoyl,2-stearoyl-sn-Glycero-3-phosphatidylcholine |
| SMPC | 1-Stearoyl,2-myristoyl-sn-Glycero-3-phosphatidylcholine |
| SOPC | 1-Stearoyl,2-oleoyl-sn-Glycero-3-phosphatidylcholine |
| SPPC | 1-Stearoyl,2-palmitoyl-sn-Glycero-3-phosphatidylcholine |

In certain embodiments, it may be advantageous to use a neutral lipid. It may also be advantageous to use a phospholipid, including a zwitterionic phospholipid, for example, a phospholipid containing one or more alkyl or alkenyl radicals of about 12 to about 22 carbons in length (e.g., about 12 to about 14, to about 16, to about 18, to about 20, to about 22 carbons), which radicals may contain, for example, from 0 to 1 to 2 to 3 double bonds. It may be advantageous to use a zwitterionic phospholipid.

Preferred phospholipids include, e.g., 1,2-dioleoyl-sn-glycero-3-phosphatidylethanolamine (DOPE), Egg phosphatidylcholine (egg PC), palmitoyl oleoyl phosphatidylcholine (POPC), dimyristoyl phosphatidylcholine (DMPC), dioleoyl phosphatidylcholine (DOPC), DPPC, dipalmitoyl phosphatidylcholine (DPPC), palmitoyl linoleyl phosphatidylcholine (PLPC), DPyPE, or a combination thereof.

In certain embodiments, the phospholipid is DOPE. The cationic oil-in-water emulsion may comprise from about 0.1 mg/ml to about 20 mg/ml DOPE. For example, the cationic oil-in-water emulsion may comprise DOPE at from about 0.5 mg/ml to about 10 mg/ml, from about 0.1 mg/ml to about 10 mg/ml, or from about 1.5 mg/ml to about 7.5 mg/ml DOPE.

In an exemplary embodiment, the cationic oil-in-water emulsion comprises about 1.5 mg/ml DOPE.

In certain embodiments, the phospholipid is egg PC. The cationic oil-in-water emulsion may comprise from about 0.1 mg/ml to about 20 mg/ml egg PC. For example, the cationic oil-in-water emulsion may comprise egg PC at from about 0.1 mg/ml to about 10 mg/ml, from about 1.0 mg/ml to about 10 mg/ml, or from about 1.5 mg/ml to about 3.5 mg/ml egg PC.

In an exemplary embodiment, the cationic oil-in-water emulsion comprises about 1.55 mg/ml egg PC.

In certain embodiments, the phospholipid is DPyPE. The cationic oil-in-water emulsion may comprise from about 0.1 mg/ml to about 20 mg/ml DPyPE. For example, the cationic oil-in-water emulsion may comprise DPyPE at from about 0.1 mg/ml to about 10 mg/ml, from about 1.5 mg/ml to about 10 mg/ml, or from about 1.5 mg/ml to about 5 mg/ml DPyPE.

In an exemplary embodiment, the cationic oil-in-water emulsion comprises about 1.6 mg/ml DPyPE.

In certain embodiments, the emulsion particles may comprise a combination of a surfactant and a phospholipid described herein.

D. Aqueous Phase (Continuous Phase)

The aqueous phase (continuous phase) of the oil-in-water emulsions is a buffered salt solution (e.g., saline) or water. The buffered salt solution is an aqueous solution that comprises a salt (e.g., NaCl), a buffer (e.g., a citrate buffer), and can further comprise an osmolality adjusting agent (e.g., a saccharide), a polymer, a surfactant, or a combination thereof. The aqueous phase can contain an antioxidant, such as citrate, ascorbate or salts thereof. If the emulsions are formulated for parenteral administration, it is preferable to make up final buffered solutions so that the tonicity, i.e., osmolality, is essentially the same as normal physiological fluids in order to prevent undesired post-administration consequences, such as post-administration swelling or rapid absorption of the composition. It is also preferable to buffer the aqueous phase in order to maintain a pH compatible with normal physiological conditions. Also, in certain instances, it may be desirable to maintain the pH at a particular level in order to insure the stability of certain components of the emulsion.

For example, it may be desirable to prepare an emulsion that is isotonic (i.e., the same permeable solute (e.g., salt) concentration as the normal cells of the body and the blood) and isosmotic. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate, magnesium chloride, calcium chloride, etc. Non-ionic tonicifying agents can also be used to control tonicity. A number of non-ionic tonicity modifying agents ordinarily known to those in the art. These are typically carbohydrates of various classifications (see, for example, Voet and Voet (1990) Biochemistry (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols, also referred to as sugar alcohols) such as glycerol, mannitol, xylitol, and sorbitol are non-ionic tonicifying agents useful in the present invention. Non-ionic tonicity modifying agents can be present at a concentration of from about 0.1% to about 10% or about 1% to about 10%, depending upon the agent that is used.

The aqueous phase may be buffered. Any physiologically acceptable buffer may be used herein, such as water, citrate buffers, phosphate buffers, acetate buffers, tris buffers, bicarbonate buffers, carbonate buffers, succinate buffer, or the like. The pH of the aqueous component will preferably be between 6.0-8.0, preferably about 6.2 to about 6.8. In an exemplary embodiment, the buffer is 10 mM citrate buffer with a pH at 6.5. In another exemplary embodiment, the aqueous phase is, or the buffer prepared using, RNase-free water or DEPC treated water. In some cases, high salt in the buffer might interfere with complexation of nucleic acid molecule to the emulsion particle therefore is avoided. In other cases, certain amount of salt in the buffer may be included.

In an exemplary embodiment, the buffer is 10 mM citrate buffer with a pH at 6.5. In another exemplary embodiment, the aqueous phase is, or the buffer is prepared using, RNase-free water or DEPC treated water.

The aqueous phase may also comprise additional components such as molecules that change the osmolarity of the aqueous phase or molecules that stabilizes the nucleic acid molecule after complexation. Preferably, the osmolarity of the aqueous phase is adjusting using a non-ionic tonicifying agent, such as a sugar (e.g., trehalose, sucrose, dextrose, fructose, reduced palatinose, etc.), a sugar alcohol (such as mannitol, sorbitol, xylitol, erythritol, lactitol, maltitol, glycerol, etc.), or combinations thereof. If desired, a nonionic polymer (e.g., a poly(alkyl glycol) such as polyethylene glycol, polypropylene glycol, or polybutlyene glycol) or nonionic surfactant can be used.

In some case, unadulterated water may be preferred as the aqueous phase of the emulsion when the emulsion is initially prepared. For example, increasing the salt concentration or sugar concentration may make it more difficult to achieve the desirable particle size (e.g., less than about 200 nm).

In certain embodiments, the aqueous phase of the cationic oil-in-water emulsion may further comprise a polymer or a surfactant, or a combination thereof. In an exemplary embodiment, the oil-in-water emulsion contains a poloxamer. Poloxamers are nonionic triblock copolymers having a central hydrophobic chain of polyoxypropylene (poly (propylene oxide)) flanked by two hydrophilic chains of polyoxyethylene (poly(ethylene oxide)). Poloxamers are also known by the trade name Pluronic® polymers. Poloxamer polymers may lead to greater stability and increased RNase resistance of the RNA molecule after RNA complexation.

Alternatively or in addition, the cationic oil-in-water emulsion may comprise from about 0.1% to about 20% (w/v) polymer, or from about 0.05% to about 10% (w/v) polymer. For example, the cationic oil-in-water emulsion may comprise a polymer (e.g., a poloxamer such as Pluronic® F127) at from about 0.1% to about 20% (w/v), from about 0.1% to about 10% (w/v), from about 0.05% to about 10% (w/v), or from about 0.05% to about 5% (w/v).

In an exemplary embodiment, the oil-in-water emulsion comprises about 4% (w/v), or about 8% (w/v) Pluronic® F127.

The quantity of the aqueous component employed in these compositions will be that amount necessary to bring the value of the composition to unity. That is, a quantity of aqueous component sufficient to make 100% will be mixed, with the other components listed above in order to bring the compositions to volume.

4. Nucleic Acid Molecules

Although not wishing to be bound by any particular theory, it is believed that the nucleic acid molecules interact with the cationic lipid through non-covalent, ionic charge interactions (electrostatic forces), and the strength of the complex as well as the amount of nucleic acid molecule that can be complexed to a particle are related to the amount of cationic lipid in the particle. Additionally, hydrophobic/hydrophilic interactions between the nucleic acid molecule and the surface of the particles may also play a role.

Nucleic acid molecules that can be complexed to the emulsion particles include single or double stranded RNA or DNA. In preferred aspects, the nucleic acid molecule is an RNA molecule, such as an RNA that encodes a peptide, polypeptide or protein, including self-replicating RNA molecules, or a small interfering RNA.

The complex can be formed by using techniques known in the art, examples of which are described herein. For example, a nucleic acid-particle complex can be formed by mixing a cationic emulsion with the nucleic acid molecule, for example by vortexing. The amount of the nucleic acid molecule and cationic lipid in the emulsions may be adjusted or optimized to provide desired strength of binding and binding capacity.

For example, as described and exemplified herein, exemplary RNA-particle complexes were produced by varying the RNA:cationic lipid ratios (as measured by the "N/P ratio"). The term N/P ratio refers to the amount (moles) of protonatable nitrogen atoms in the cationic lipid divided by the amount (moles) of phosphates on the RNA. The N/P ratio is at least, for example from 4:1 to 20:1 or from 4:1 to 15:1.

In some embodiments, the N/P ratio is from 1.1:1 to 20:1, 1.1:1 to 15:1, 1.5:1 to 20:1, 1.5:1 to 15:1, 2:1 to 20:1, 2:1 to 15:1, 2.5:1 to 20:1, 2.5:1 to 15:1, 3:1 to 20:1, 3:1 to 15:1, 3.5:1 to 20:1, or 3.5:1 to 15:1.

The cationic oil-in-water emulsions described herein are particularly suitable for formulating nucleic acid-based vaccines (e.g., DNA vaccines, RNA vaccines). The formation of a nucleic acid-emulsion particle complex facilitates the uptake of the nucleic acid into host cells, and protects the nucleic acid molecule from nuclease degradation. Transfected cells can then express the antigen encoded by the nucleic acid molecule, which can produce an immune response to the antigen. Like live or attenuated viruses, nucleic acid-based vaccines can effectively engage both MHC-I and MHC-II pathways allowing for the induction of $CD8^+$ and $CD4^+$ T cell responses, whereas antigen present in soluble form, such as recombinant protein, generally induces only antibody responses.

The sequence of the nucleic acid molecule (e.g., RNA molecule) may be codon optimized or deoptimized for expression in a desired host, such as a human cell.

In certain embodiments, the nucleic acid molecule is an RNA molecule. In certain embodiments, the RNA molecule encodes an antigen (peptide, polypeptide or protein) and the cationic oil in water emulsion is suitable for use as an RNA-based vaccine. The composition can contain more than one RNA molecule encoding an antigen, e.g., two, three, five, or ten RNA molecules that are complexed to the emulsion particles. That is, the composition can contain one or more different species of RNA molecules, each encoding a different antigen. Alternatively or in addition, one RNA molecule may also encode more than one antigen, e.g., a bicistronic, or tricistronic RNA molecule that encodes different or identical antigens. Accordingly, the cationic oil in water emulsion is suitable for use as an RNA-based vaccine, that is monovalent or multivalent.

The sequence of the RNA molecule may be modified if desired, for example to increase the efficacy of expression or replication of the RNA, or to provide additional stability or resistance to degradation. For example, the RNA sequence can be modified with respect to its codon usage, for example, to increase translation efficacy and half-life of the RNA. A poly A tail (e.g., of about 30 adenosine residues or more (SEQ ID NO: 3)) may be attached to the 3' end of the RNA to increase its half-life. The 5' end of the RNA may be capped with a modified ribonucleotide with the structure m7G (5') ppp (5') N (cap 0 structure) or a derivative thereof, which can be incorporated during RNA synthesis or can be enzymatically engineered after RNA transcription (e.g., by using Vaccinia Virus Capping Enzyme (VCE) consisting of mRNA triphosphatase, guanylyl-transferase and guanine-7-methyltransferase, which catalyzes the construction of N7-monomethylated cap 0 structures). Cap 0 structure plays an important role in maintaining the stability and translational efficacy of the RNA molecule. The 5' cap of the RNA molecule may be further modified by a 2'-O-Methyltransferase which results in the generation of a cap 1 structure (m7Gppp [m2'-O]N), which may further increases translation efficacy.

If desired, the RNA molecule can comprise one or more modified nucleotides, in addition to any 5' cap structure. There are more than 96 naturally occurring nucleoside modifications found on mammalian RNA. See, e.g., Limbach et al., *Nucleic Acids Research*, 22(12):2183-2196 (1994). The preparation of nucleotides and modified nucleotides and nucleosides are well-known in the art, e.g. from U.S. Pat. Nos. 4,373,071, 4,458,066, 4,500,707, 4,668,777, 4,973,679, 5,047,524, 5,132,418, 5,153,319, 5,262,530, 5,700,642 all of which are incorporated by reference in their entirety herein, and many modified nucleosides and modified nucleotides are commercially available.

Modified nucleobases which can be incorporated into modified nucleosides and nucleotides and be present in the RNA molecules include: m5C (5-methylcytidine), m5U (5-methyluridine), m6A (N6-methyladenosine), s2U (2-thiouridine), Um (2'-O-methyluridine), m1A (1-methyladenosine); m2A (2-methyladenosine); Am (2-1-O-methyladenosine); ms2m6A (2-methylthio-N6-methyladenosine); i6A (N6-isopentenyladenosine); ms2i6A (2-methylthio-N6isopentenyladenosine); io6A (N6-(cis-hydroxyisopentenyl)adenosine); ms2io6A (2-methylthio-N6-(cis-hydroxyisopentenyl) adenosine); g6A (N6-glycinylcarbamoyladenosine); t6A (N6-threonyl carbamoyladenosine); ms2t6A (2-methylthio-N6-threonyl carbamoyladenosine); m6t6A (N6-methyl-N6-threonylcarbamoyladenosine); hn6A (N6-hydroxynorvalylcarbamoyl adenosine); ms2hn6A (2-methylthio-N6-hydroxynorvalyl carbamoyladenosine); Ar(p) (2'-O-ribosyladenosine (phosphate)); I (inosine); m1I (1-methylinosine); m'Im (1,2'-O-dimethylinosine); m3C (3-methylcytidine); Cm (2T-O-methylcytidine); s2C (2-thiocytidine); ac4C (N4-acetylcytidine); f5C (5-fonnylcytidine); m5Cm (5,2-O-dimethylcytidine); ac4Cm (N4acetyl2TOmethylcytidine); k2C (lysidine); m1G (1-methylguanosine); m2G (N2-methylguanosine); m7G (7-methylguanosine); Gm (2'-O-methylguanosine); m22G (N2,N2-dimethylguanosine); m2Gm (N2,2'-O-dimethylguanosine); m22Gm (N2,N2,2'-O-trimethylguanosine); Gr(p) (2'-O-ribosylguanosine (phosphate)); yW (wybutosine); o2yW (peroxywybutosine); OHyW (hydroxywybutosine); OHyW* (undermodified hydroxywybutosine); imG (wyosine); mimG (methylguanosine); Q (queuosine); oQ (epoxyqueuosine); galQ (galtactosyl-queuosine); manQ (mannosyl-queuosine); preQo (7-cyano-7-deazaguanosine); preQi (7-aminomethyl-7-deazaguanosine); G* (archaeosine); D (dihydrouridine);

m5Um (5,2'-O-dimethyluridine); s4U (4-thiouridine); m5s2U (5-methyl-2-thiouridine); s2Um (2-thio-2'-O-methyluridine); acp3U (3-(3-amino-3-carboxypropyl)uridine); ho5U (5-hydroxyuridine); mo5U (5-methoxyuridine); cmo5U (uridine 5-oxyacetic acid); mcmo5U (uridine 5-oxyacetic acid methyl ester); chm5U (5-(carboxyhydroxymethyl)uridine)); mchm5U (5-(carboxyhydroxymethyl)uridine methyl ester); mcm5U (5-methoxycarbonyl methyluridine); mcm5Um (S-methoxycarbonylmethyl-2-O-methyluridine); mcm5s2U (5-methoxycarbonylmethyl-2-thiouridine); nm5s2U (5-aminomethyl-2-thiouridine); mnm5U (5-methylaminomethyluridine); mnm5s2U (5-methylaminomethyl-2-thiouridine); mnm5se2U (5-methylaminomethyl-2-selenouridine); ncm5U (5-carbamoylmethyl uridine); ncm5Um (5-carbamoylmethyl-2'-O-methyluridine); cmnm5U (5-carboxymethylaminomethyluridine); cnmm5Um (5-carboxymethylaminomethyl-2-L-Omethyluridine); cmnm5s2U (5-carboxymethylaminomethyl-2-thiouridine); m62A (N6,N6-dimethyladenosine); Tm (2'-O-methylinosine); m4C (N4-methylcytidine); m4Cm (N4,2-O-dimethylcytidine); hm5C (5-hydroxymethylcytidine); m3U (3-methyluridine); cm5U (5-carboxymethyluridine); m6Am (N6,T-O-dimethyladenosine); rn62Am (N6,N6,O-2-trimethyladenosine); m2'7G (N2,7-dimethylguanosine); m2'2'7G (N2,N2,7-trimethylguano sine); m3Um (3,2T-O-dimethyluridine); m5D (5-methyldihydrouridine); f5Cm (5-formyl-2'-O-methylcytidine); m1Gm (1,2'-O-dimethylguanosine); m'Am (1,2-O-dimethyl adenosine) irinomethyluridine); tm5s2U (S-taurinomethyl-2-thiouridine)); imG-14 (4-demethyl guanosine); imG2 (isoguanosine); ac6A (N6-acetyladenosine), hypoxanthine, inosine, 8-oxo-adenine, 7-substituted derivatives thereof, dihydrouracil, pseudouracil, 2-thiouracil, 4-thiouracil, 5-aminouracil, 5-($C_1$-$C_6$)-alkyluracil, 5-methyluracil, 5-($C_2$-$C_6$)-alkenyluracil, 5-($C_2$-$C_6$)-alkynyluracil, 5-(hydroxymethyl)uracil, 5-chlorouracil, 5-fluorouracil, 5-bromouracil, 5-hydroxycytosine, 5-($C_1$-$C_6$)-alkylcytosine, 5-methylcytosine, 5-($C_2$-$C_6$)-alkenylcytosine, 5-($C_2$-$C_6$)-alkynylcytosine, 5-chlorocytosine, 5-fluorocytosine, 5-bromocytosine, $N^2$-dimethylguanine, 7-deazaguanine, 8-azaguanine, 7-deaza-7-substituted guanine, 7-deaza-7-(C2-C6)alkynylguanine, 7-deaza-8-substituted guanine, 8-hydroxyguanine, 6-thioguanine, 8-oxoguanine, 2-aminopurine, 2-amino-6-chloropurine, 2,4-diaminopurine, 2,6-diaminopurine, 8-azapurine, substituted 7-deazapurine, 7-deaza-7-substituted purine, 7-deaza-8-substituted purine, hydrogen (abasic residue), m5C, m5U, m6A, s2U, W, or 2'-O-methyl-U. Many of these modified nucleobases and their corresponding ribonucleosides are available from commercial suppliers. See, e.g., WO 2011/005799 which is incorporated herein by reference.

A RNA used with the invention ideally includes only phosphodiester linkages between nucleosides, but in some embodiments it can contain phosphoramidate, phosphorothioate, and/or methylphosphonate linkages.

In some embodiments, the RNA molecule does not include modified nucleotides, e.g., does not include modified nucleobases, and all of the nucleotides in the RNA molecule are conventional standard ribonucleotides A, U, G and C, with the exception of an optional 5' cap that may include, for example, 7-methylguanosine. In other embodiments, the RNA may include a 5' cap comprising a 7'-methylguanosine, and the first 1, 2 or 3 5' ribonucleotides may be methylated at the 2' position of the ribose.

A. Self-replicating RNA

In some aspects, the cationic oil in water emulsion contains a self-replicating RNA molecule. In certain embodiments, the self-replicating RNA molecule is derived from or based on an alphavirus.

Self-replicating RNA molecules are well known in the art and can be produced by using replication elements derived from, e.g., alphaviruses, and substituting the structural viral proteins with a nucleotide sequence encoding a protein of interest. A self-replicating RNA molecule is typically a (+)-strand molecule which can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded antigen, or may be transcribed to provide further transcripts with the same sense as the delivered RNA which are translated to provide in situ expression of the antigen. The overall result of this sequence of transcriptions is a huge amplification in the number of the introduced replicon RNAs and so the encoded antigen becomes a major polypeptide product of the cells. Cells transfected with self-replicating RNA briefly produce antigen before undergoing apoptotic death. This death is a likely result of requisite double-stranded (ds) RNA intermediates, which also have been shown to super-activate Dendritic Cells. Thus, the enhanced immunogenicity of self-replicating RNA may be a result of the production of pro-inflammatory dsRNA, which mimics an RNA-virus infection of host cells.

Advantageously, the cell's machinery is used by self-replicating RNA molecules to generate an exponential increase of encoded gene products, such as proteins or antigens, which can accumulate in the cells or be secreted from the cells. Overexpression of proteins by self-replicating RNA molecules takes advantage of the immunostimulatory adjuvant effects, including stimulation of toll-like receptors (TLR) 3, 7 and 8 and non TLR pathways (e.g, RIG-1, MD-5) by the products of RNA replication and amplification, and translation which induces apoptosis of the transfected cell.

The self-replicating RNA generally contains at least one or more genes selected from the group consisting of viral replicases, viral proteases, viral helicases and other non-structural viral proteins, and also comprise 5'- and 3'-end cis-active replication sequences, and if desired, a heterologous sequences that encode a desired amino acid sequences (e.g., an antigen of interest). A subgenomic promoter that directs expression of the heterologous sequence can be included in the self-replicating RNA. If desired, the heterologous sequence (e.g., an antigen of interest) may be fused in frame to other coding regions in the self-replicating RNA and/or may be under the control of an internal ribosome entry site (IRES).

In certain embodiments, the self-replicating RNA molecule is not encapsulated in a virus-like particle. Self-replicating RNA molecules of the invention can be designed so that the self-replicating RNA molecule cannot induce production of infectious viral particles. This can be achieved, for example, by omitting one or more viral genes encoding structural proteins that are necessary for the production of viral particles in the self-replicating RNA. For example, when the self-replicating RNA molecule is based on an alpha virus, such as Sinebis virus (SIN), Semliki forest virus and Venezuelan equine encephalitis virus (VEE), one or more genes encoding viral structural proteins, such as capsid and/or envelope glycoproteins, can be omitted.

If desired, self-replicating RNA molecules of the invention can also be designed to induce production of infectious viral particles that are attenuated or virulent, or to produce viral particles that are capable of a single round of subsequent infection.

One suitable system for achieving self-replication in this manner is to use an alphavirus-based replicon. Alphaviruses comprise a set of genetically, structurally, and serologically related arthropod-borne viruses of the Togaviridae family. Twenty-six known viruses and virus subtypes have been classified within the alphavirus genus, including, Sindbis virus, Semliki Forest virus, Ross River virus, and Venezuelan equine encephalitis virus. As such, the self-replicating RNA of the invention may incorporate a RNA replicase derived from semliki forest virus (SFV), sindbis virus (SIN), Venezuelan equine encephalitis virus (VEE), Ross-River virus (RRV), eastern equine encephalitis virus, or other viruses belonging to the alphavirus family.

An alphavirus-based "replicon" expression vector can be used in the invention. Replicon vectors may be utilized in several formats, including DNA, RNA, and recombinant replicon particles. Such replicon vectors have been derived from alphaviruses that include, for example, Sindbis virus (Xiong et al. (1989) Science 243:1188-1191; Dubensky et al., (1996) J. Virol. 70:508-519; Hariharan et al. (1998) J. Virol. 72:950-958; Polo et al. (1999) PNAS 96:4598-4603), Semliki Forest virus (Liljestrom (1991) Bio/Technology 9:1356-1361; Berglund et al. (1998) Nat. Biotech. 16:562-565), and Venezuelan equine encephalitis virus (Pushko et al. (1997) Virology 239:389-401). Alphavirus-derived replicons are generally quite similar in overall characteristics (e.g., structure, replication), individual alphavirus may exhibit some particular property (e.g., receptor binding, interferon sensitivity, and disease profile) that is unique. Therefore, chimeric alphavirus replicons made from divergent virus families may also be useful.

Alphavirus-based RNA replicons are typically (+)-stranded RNAs which lead to translation of a replicase (or replicase-transcriptase) after delivery to a cell. The replicase is translated as a polyprotein which auto-cleaves to provide a replication complex which creates genomic (−)-strand copies of the (+)-strand delivered RNA. These (−)-strand transcripts can themselves be transcribed to give further copies of the (+)-stranded parent RNA and also to give a subgenomic transcript which encodes the antigen. Translation of the subgenomic transcript thus leads to in situ expression of the antigen by the infected cell. Suitable alphavirus replicons can use a replicase from a Sindbis virus, a Semliki forest virus, an eastern equine encephalitis virus, a Venezuelan equine encephalitis virus, etc.

An RNA replicon preferably comprises an RNA genome from a picornavirus, togavirus, flavivirus, coronavirus, paramyxovirus, yellow fever virus, or alphavirus (e.g., Sindbis virus, Semliki Forest virus, Venezuelan equine encephalitis virus, or Ross River virus), which has been modified by the replacement of one or more structural protein genes with a selected heterologous nucleic acid sequence encoding a product of interest.

A preferred replicon encodes (i) a RNA-dependent RNA polymerase which can transcribe RNA from the replicon and (ii) an antigen. The polymerase can be an alphavirus replicase e.g. comprising one or more of alphavirus proteins nsP1, nsP2, nsP3 and nsP4. Whereas natural alphavirus genomes encode structural virion proteins in addition to the non-structural replicase polyprotein, it is preferred that the replicon does not encode alphavirus structural proteins. Thus a preferred replicon can lead to the production of genomic RNA copies of itself in a cell, but not to the production of RNA-containing virions. The inability to produce these virions means that, unlike a wild-type alphavirus, the preferred replicon cannot perpetuate itself in infectious form. The alphavirus structural proteins which are necessary for perpetuation in wild-type viruses are absent from the preferred replicon and their place is taken by gene(s) encoding the antigen of interest, such that the subgenomic transcript encodes the antigen rather than the structural alphavirus virion proteins.

A replicon useful with the invention may have two open reading frames. The first (5') open reading frame encodes a replicase; the second (3') open reading frame encodes an antigen. In some embodiments the RNA may have additional (e.g. downstream) open reading frames e.g. to encode additional antigens or to encode accessory polypeptides.

A preferred replicon has a 5' cap (e.g. a 7-methylguanosine), which often can enhance in vivo translation of the RNA. In some embodiments the 5' sequence of the replicon may need to be selected to ensure compatibility with the encoded replicase.

A replicon may have a 3' poly-A tail. It may also include a poly-A polymerase recognition sequence (e.g. AAUAAA) near its 3' end.

Replicons can have various lengths but they are typically 5000-25000 nucleotides long e.g. 8000-15000 nucleotides, or 9000-12000 nucleotides.

The replicon can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the replicon from a DNA template. Appropriate capping and poly-A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT-transcribed RNA can function efficiently as a substrate for its self-encoded replicase. Specific examples include Sindbis-virus-based plasmids (pSIN) such as pSINCP, described, for example, in U.S. Pat. Nos. 5,814,482 and 6,015,686, as well as in International Publication Nos. WO 97/38087, WO 99/18226 and WO 02/26209. The construction of such replicons, in general, is described in U.S. Pat. Nos. 5,814,482 and 6,015,686.

In other aspects, the self-replicating RNA molecule is derived from or based on a virus other than an alphavirus, preferably, a positive-stranded RNA virus, and more preferably a picornavirus, flavivirus, rubivirus, pestivirus, hepacivirus, calicivirus, or coronavirus. Suitable wild-type alphavirus sequences are well-known and are available from sequence depositories, such as the American Type Culture Collection, Rockville, Md. Representative examples of suitable alphaviruses include Aura (ATCC VR-368), Bebaru virus (ATCC VR-600, ATCC VR-1240), Cabassou (ATCC VR-922), Chikungunya virus (ATCC VR-64, ATCC VR-1241), Eastern equine encephalomyelitis virus (ATCC VR-65, ATCC VR-1242), Fort Morgan (ATCC VR-924), Getah virus (ATCC VR-369, ATCC VR-1243), Kyzylagach (ATCC VR-927), Mayaro (ATCC VR-66), Mayaro virus (ATCC VR-1277), Middleburg (ATCC VR-370), Mucambo virus (ATCC VR-580, ATCC VR-1244), Ndumu (ATCC VR-371), Pixuna virus (ATCC VR-372, ATCC VR-1245), Ross River virus (ATCC VR-373, ATCC VR-1246), Semliki Forest (ATCC VR-67, ATCC VR-1247), Sindbis virus (ATCC VR-68, ATCC VR-1248), Tonate (ATCC VR-925), Triniti (ATCC VR-469), Una (ATCC VR-374), Venezuelan equine encephalomyelitis (ATCC VR-69, ATCC VR-923, ATCC VR-1250 ATCC VR-1249, ATCC VR-532), Western equine encephalomyelitis (ATCC VR-70, ATCC VR-1251, ATCC VR-622, ATCC VR-1252), Whataroa (ATCC VR-926), and Y-62-33 (ATCC VR-375).

The self-replicating RNA molecules of the invention are larger than other types of RNA (e.g. mRNA) that have been prepared using modified nucleotides. Typically, the self-replicating RNA molecules of the invention contain at least about 4 kb. For example, the self-replicating RNA can contain at least about 5 kb, at least about 6 kb, at least about 7 kb, at least about 8 kb, at least about 9 kb, at least about 10 kb, at least about 11 kb, at least about 12 kb or more than 12 kb. In certain examples, the self-replicating RNA is about 4 kb to about 12 kb, about 5 kb to about 12 kb, about 6 kb to about 12 kb, about 7 kb to about 12 kb, about 8 kb to about 12 kb, about 9 kb to about 12 kb, about 10 kb to about 12 kb, about 11 kb to about 12 kb, about 5 kb to about 11 kb, about 5 kb to about 10 kb, about 5 kb to about 9 kb, about 5 kb to about 8 kb, about 5 kb to about 7 kb, about 5 kb to about 6 kb, about 6 kb to about 12 kb, about 6 kb to about 11 kb, about 6 kb to about 10 kb, about 6 kb to about 9 kb, about 6 kb to about 8 kb, about 6 kb to about 7 kb, about 7 kb to about 11 kb, about 7 kb to about 10 kb, about 7 kb to about 9 kb, about 7 kb to about 8 kb, about 8 kb to about 11 kb, about 8 kb to about 10 kb, about 8 kb to about 9 kb, about 9 kb to about 11 kb, about 9 kb to about 10 kb, or about 10 kb to about 11 kb.

The self-replicating RNA molecules of the invention may comprise one or more types of modified nucleotides (e.g., pseudouridine, N6-methyladenosine, 5-methylcytidine, 5-methyluridine).

The self-replicating RNA molecule may encode a single heterologous polypeptide antigen or, optionally, two or more heterologous polypeptide antigens linked together in a way that each of the sequences retains its identity (e.g., linked in series) when expressed as an amino acid sequence. The heterologous polypeptides generated from the self-replicating RNA may then be produced as a fusion polypeptide or engineered in such a manner to result in separate polypeptide or peptide sequences.

The self-replicating RNA of the invention may encode one or more polypeptide antigens that contain a range of epitopes. Preferably epitopes capable of eliciting either a helper T-cell response or a cytotoxic T-cell response or both.

The self-replicating RNA molecules described herein may be engineered to express multiple nucleotide sequences, from two or more open reading frames, thereby allowing co-expression of proteins, such as two or more antigens together with cytokines or other immunomodulators, which can enhance the generation of an immune response. Such a self-replicating RNA molecule might be particularly useful, for example, in the production of various gene products (e.g., proteins) at the same time, for example, as a bivalent or multivalent vaccine.

The self-replicating RNA molecules of the invention can be prepared using any suitable method. Several suitable methods are known in the art for producing RNA molecules that contain modified nucleotides. For example, a self-replicating RNA molecule that contains modified nucleotides can be prepared by transcribing (e.g., in vitro transcription) a DNA that encodes the self-replicating RNA molecule using a suitable DNA-dependent RNA polymerase, such as T7 phage RNA polymerase, SP6 phage RNA polymerase, T3 phage RNA polymerase, and the like, or mutants of these polymerases which allow efficient incorporation of modified nucleotides into RNA molecules. The transcription reaction will contain nucleotides and modified nucleotides, and other components that support the activity of the selected polymerase, such as a suitable buffer, and suitable salts. The incorporation of nucleotide analogs into a self-replicating RNA may be engineered, for example, to alter the stability of such RNA molecules, to increase resistance against RNases, to establish replication after introduction into appropriate host cells ("infectivity" of the RNA), and/or to induce or reduce innate and adaptive immune responses.

Suitable synthetic methods can be used alone, or in combination with one or more other methods (e.g., recombinant DNA or RNA technology), to produce a self-replicating RNA molecule of the invention. Suitable methods for de novo synthesis are well-known in the art and can be adapted for particular applications. Exemplary methods include, for example, chemical synthesis using suitable protecting groups such as CEM (Masuda et al., (2007) *Nucleic Acids Symposium Series* 51:3-4), the β-cyanoethyl phosphoramidite method (Beaucage S L et al. (1981) *Tetrahedron Lett* 22:1859); nucleoside H-phosphonate method (Garegg P et al. (1986) *Tetrahedron Lett* 27:4051-4; Froehler B C et al. (1986) *Nucl Acid Res* 14:5399-407; Garegg P et al. (1986) *Tetrahedron Lett* 27:4055-8; Gaffney B L et al. (1988) *Tetrahedron Lett* 29:2619-22). These chemistries can be performed or adapted for use with automated nucleic acid synthesizers that are commercially available. Additional suitable synthetic methods are disclosed in Uhlmann et al. (1990) *Chem Rev* 90:544-84, and Goodchild J (1990) *Bioconjugate Chem* 1: 165. Nucleic acid synthesis can also be performed using suitable recombinant methods that are well-known and conventional in the art, including cloning, processing, and/or expression of polynucleotides and gene products encoded by such polynucleotides. DNA shuffling by random fragmentation and PCR reassembly of gene fragments and synthetic polynucleotides are examples of known techniques that can be used to design and engineer polynucleotide sequences. Site-directed mutagenesis can be used to alter nucleic acids and the encoded proteins, for example, to insert new restriction sites, alter glycosylation patterns, change codon preference, produce splice variants, introduce mutations and the like. Suitable methods for transcription, translation and expression of nucleic acid sequences are known and conventional in the art. (See generally, Current Protocols in Molecular Biology, Vol. 2, Ed. Ausubel, et al., Greene Publish. Assoc. & Wiley Interscience, Ch. 13, 1988; Glover, DNA Cloning, Vol. II, IRL Press, Wash., D.C., Ch. 3, 1986; Bitter, et al., in Methods in Enzymology 153:516-544 (1987); The Molecular Biology of the Yeast *Saccharomyces*, Eds. Strathern et al., Cold Spring Harbor Press, Vols. I and II, 1982; and Sambrook et al., Molecular Cloning: A Laboratory Manual, Cold Spring Harbor Press, 1989.)

The presence and/or quantity of one or more modified nucleotides in a self-replicating RNA molecule can be determined using any suitable method. For example, a self-replicating RNA can be digested to monophosphates (e.g., using nuclease P1) and dephosphorylated (e.g., using a suitable phosphatase such as CIAP), and the resulting nucleosides analyzed by reversed phase HPLC (e.g., usings a YMC Pack ODS-AQ column (5 micron, 4.6×250 mm) and elute using a gradient, 30% B (0-5 min) to 100% B (5-13 min) and at 100% B (13-40) min, flow Rate (0.7 ml/min), UV detection (wavelength: 260 nm), column temperature (30° C.). Buffer A (20 mM acetic acid—ammonium acetate pH 3.5), buffer B (20 mM acetic acid—ammonium acetate pH 3.5/methanol [90/10])).

Optionally, the self-replicating RNA molecules of the invention may include one or more modified nucleotides so that the self-replicating RNA molecule will have less immunomodulatory activity upon introduction or entry into a host cell (e.g., a human cell) in comparison to the corresponding self-replicating RNA molecule that does not contain modified nucleotides.

If desired, the self-replicating RNA molecules can be screened or analyzed to confirm their therapeutic and prophylactic properties using various in vitro or in vivo testing methods that are known to those of skill in the art. For example, vaccines comprising self-replicating RNA molecule can be tested for their effect on induction of proliferation or effector function of the particular lymphocyte type of interest, e.g., B cells, T cells, T cell lines, and T cell clones. For example, spleen cells from immunized mice can be isolated and the capacity of cytotoxic T lymphocytes to lyse autologous target cells that contain a self replicating RNA molecule that encodes a polypeptide antigen. In addition, T helper cell differentiation can be analyzed by measuring proliferation or production of TH1 (IL-2 and IFN-γ) and/or TH2 (IL-4 and IL-5) cytokines by ELISA or directly in CD4+ T cells by cytoplasmic cytokine staining and flow cytometry.

Self-replicating RNA molecules that encode a polypeptide antigen can also be tested for ability to induce humoral immune responses, as evidenced, for example, by induction of B cell production of antibodies specific for an antigen of interest. These assays can be conducted using, for example, peripheral B lymphocytes from immunized individuals. Such assay methods are known to those of skill in the art. Other assays that can be used to characterize the self-replicating RNA molecules of the invention can involve detecting expression of the encoded antigen by the target cells. For example, FACS can be used to detect antigen expression on the cell surface or intracellularly. Another advantage of FACS selection is that one can sort for different levels of expression; sometimes-lower expression may be desired. Other suitable method for identifying cells which express a particular antigen involve panning using monoclonal antibodies on a plate or capture using magnetic beads coated with monoclonal antibodies.

B. Antigens

In certain embodiments, the nucleic acid molecule described herein is a nucleic acid molecule (e.g., an RNA molecule) that encodes an antigen. Suitable antigens include, but are not limited to, a bacterial antigen, a viral antigen, a fungal antigen, a protazoan antigen, a plant antigen, a cancer antigen, or a combination thereof.

Suitable antigens include proteins and peptides from a pathogen such as a virus, bacteria, fungus, protozoan, plant or from a tumor. Viral antigens and immunogens that can be encoded by the self-replicating RNA molecule include, but are not limited to, proteins and peptides from a Orthomyxoviruses, such as Influenza A, B and C; Paramyxoviridae viruses, such as Pneumoviruses (RSV), Paramyxoviruses (PIV), Metapneumovirus and Morbilliviruses (e.g., measles); Pneumoviruses, such as Respiratory syncytial virus (RSV), Bovine respiratory syncytial virus, Pneumonia virus of mice, and Turkey rhinotracheitis virus; Paramyxoviruses, such as Parainfluenza virus types 1-4 (PIV), Mumps virus, Sendai viruses, Simian virus 5, Bovine parainfluenza virus, Nipahvirus, Henipavirus and Newcastle disease virus; Poxviridae, including a Orthopoxvirus such as Variola vera (including but not limited to, Variola major and Variola minor); Metapneumoviruses, such as human metapneumovirus (hMPV) and avian metapneumoviruses (aMPV); Morbilliviruses, such as Measles; Picornaviruses, such as Enteroviruses, Rhinoviruses, Heparnavirus, Parechovirus, Cardioviruses and Aphthoviruses; Enteroviruseses, such as Poliovirus types 1, 2 or 3, Coxsackie A virus types 1 to 22 and 24, Coxsackie B virus types 1 to 6, Echovirus (ECHO) virus types 1 to 9, 11 to 27 and 29 to 34 and Enterovirus 68 to 71, Bunyaviruses, including a Orthobunyavirus such as California encephalitis virus; a Phlebovirus, such as Rift Valley Fever virus; a Nairovirus, such as Crimean-Congo hemorrhagic fever virus; Heparnaviruses, such as, Hepatitis A virus (HAV); Togaviruses (Rubella), such as a Rubivirus, an Alphavirus, or an Arterivirus; Flaviviruses, such as Tickborne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus; Pestiviruses, such as Bovine viral diarrhea (BVDV), Classical swine fever (CSFV) or Border disease (BDV); Hepadnaviruses, such as Hepatitis B virus, Hepatitis C virus; Rhabdoviruses, such as a Lyssavirus (Rabies virus) and Vesiculovirus (VSV), Caliciviridae, such as Norwalk virus, and Norwalk-like Viruses, such as Hawaii Virus and Snow Mountain Virus; Coronaviruses, such as SARS, Human respiratory coronavirus, Avian infectious bronchitis (IBV), Mouse hepatitis virus (MHV), and Porcine transmissible gastroenteritis virus (TGEV); Retroviruses such as an Oncovirus, a Lentivirus or a Spumavirus; Reoviruses, as an Orthoreovirus, a Rotavirus, an Orbivirus, or a Coltivirus; Parvoviruses, such as Parvovirus B19; Delta hepatitis virus (HDV); Hepatitis E virus (HEV); Hepatitis G virus (HGV); Human Herpesviruses, such as, by way Herpes Simplex Viruses (HSV), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8); Papovaviruses, such as Papillomaviruses and Polyomaviruses, Adenoviruess and Arenaviruses.

In some embodiments, the antigen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

In some embodiments the antigen elicits an immune response against a parasite from the *Plasmodium* genus, such as *P. falciparum, P. vivax, P. malariae* or *P. ovale*. Thus the invention may be used for immunizing against malaria. In some embodiments the antigen elicits an immune response against a parasite from the Caligidae family, particularly those from the *Lepeophtheirus* and *Caligus* genera e.g. sea lice such as *Lepeophtheirus salmonis* or *Caligus rogercresseyi*.

Bacterial antigens and immunogens that can be encoded by the self-replicating RNA molecule include, but are not limited to, proteins and peptides from *Neisseria meningiti-* des, *Streptococcus pneumoniae, Streptococcus pyogenes, Moraxella catarrhalis, Bordetella pertussis, Burkholderia* sp. (e.g., *Burkholderia mallei, Burkholderia pseudomallei* and *Burkholderia cepacia*), *Staphylococcus aureus, Staphylococcus epidermis, Haemophilus influenzae, Clostridium tetani* (Tetanus), *Clostridium perfringens, Clostridium botulinums* (Botulism), *Cornynebacterium diphtheriae* (Diphtheria), *Pseudomonas aeruginosa, Legionella pneumophila, Coxiella burnetii, Brucella* sp. (e.g., *B. abortus, B. canis, B. melitensis, B. neotomae, B. ovis, B. suis* and *B. pinnipediae*), *Francisella* sp. (e.g., *F. novicida, F. philomiragia* and *F. tularensis*), *Streptococcus agalactiae, Neiserria gonorrhoeae, Chlamydia trachomatis, Treponema pallidum* (Syphilis), *Haemophilus ducreyi, Enterococcus faecalis, Enterococcus faecium, Helicobacter* pylori, *Staphylococcus saprophyticus, Yersinia enterocolitica, E. coli* (such as enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC; such as uropathogenic *E. coli* (UPEC) and meningitis/sepsis-associated *E. coli* (MNEC)), and/or enterohemorrhagic *E. coli* (EHEC), *Bacillus anthracis* (anthrax), *Yersinia pestis* (plague), *Mycobacterium tuberculosis, Rickettsia, Listeria monocytogenes, Chlamydia pneumoniae, Vibrio cholerae, Salmonella typhi* (typhoid fever), *Borrelia burgdorfer, Porphyromonas gingivalis, Klebsiella, Mycoplasma pneumoniae*, etc.

Fungal antigens and immunogens that can be encoded by the self-replicating RNA molecule include, but are not limited to, proteins and peptides from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. *album*, var. *discoides*, var. *ochraceum, Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

Protazoan antigens and immunogens that can be encoded by the self-replicating RNA molecule include, but are not limited to, proteins and peptides from *Entamoeba histolytica, Giardia lambli, Cryptosporidium parvum, Cyclospora cayatanensis* and *Toxoplasma*.

Plant antigens and immunogens that can be encoded by the self-replicating RNA molecule include, but are not limited to, proteins and peptides from *Ricinus communis*.

Suitable antigens include proteins and peptides from a virus such as, for example, human immunodeficiency virus (HIV), hepatitis A virus (HAV), hepatitis B virus (HBV), hepatitis C virus (HCV), herpes simplex virus (HSV), cytomegalovirus (CMV), influenza virus (flu), respiratory syncytial virus (RSV), parvovorus, norovirus, human papilloma virus (HPV), rhinovirus, yellow fever virus, rabies virus, Dengue fever virus, measles virus, mumps virus, rubella virus, varicella zoster virus, enterovirus (e.g., enterovirus 71), ebola virus, and bovine diarrhea virus. Preferably, the antigenic substance is selected from the group consisting of HSV glycoprotein gD, HIV glycoprotein gp120, HIV glycoprotein gp 40, HIV p55 gag, and polypeptides from the pol and tat regions. In other preferred embodiments of the invention, the antigen is a protein or peptide derived from a bacterium such as, for example, *Helicobacter pylori, Haemophilus influenza, Vibrio cholerae* (cholera), *C. diphtheriae* (diphtheria), *C. tetani* (tetanus), *Neisseria meningitidis, B. pertussis, Mycobacterium tuberculosis*, and the like.

HIV antigens that can be encoded by the self-replicating RNA molecules of the invention are described in U.S. application Ser. No. 490,858, filed Mar. 9, 1990, and published European application number 181150 (May 14, 1986), as well as U.S. application Ser. Nos. 60/168,471; 09/475,515; 09/475,504; and Ser. No. 09/610,313, the disclosures of which are incorporated herein by reference in their entirety.

Cytomegalovirus antigens that can be encoded by the self-replicating RNA molecules of the invention are described in U.S. Pat. No. 4,689,225, U.S. application Ser. No. 367,363, filed Jun. 16, 1989 and PCT Publication WO 89/07143, the disclosures of which are incorporated herein by reference in their entirety.

Hepatitis C antigens that can be encoded by the self-replicating RNA molecules of the invention are described in PCT/US88/04125, published European application number 318216 (May 31, 1989), published Japanese application number 1-500565 filed Nov. 18, 1988, Canadian application 583,561, and EPO 388,232, disclosures of which are incorporated herein by reference in their entirety. A different set of HCV antigens is described in European patent application 90/302866.0, filed Mar. 16, 1990, and U.S. application Ser. No. 456,637, filed Dec. 21, 1989, and PCT/US90/01348, the disclosures of which are incorporated herein by reference in their entirety.

In some embodiments, the antigen is derived from an allergen, such as pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (*Betula*), alder (*Alnus*), hazel (*Corylus*), hornbeam (*Carpinus*) and olive (*Olea*), cedar (*Cryptomeria* and *Juniperus*), plane tree (*Platanus*), the order of Poales including grasses of the genera *Lolium, Phleum, Poa, Cynodon, Dac-*

*tylis, Holcus, Phalaris, Secale*, and Sorghum, the orders of Asterales and Urticales including herbs of the genera *Ambrosia, Artemisia*, and *Parietaria*. Other important inhalation allergens are those from house dust mites of the genus *Dermatophagoides* and Euroglyphus, storage mite e.g. Lepidoglyphys, Glycyphagus and Tyrophagus, those from cockroaches, midges and fleas e.g. Blatella, *Periplaneta*, Chironomus and Ctenocepphalides, and those from mammals such as cat, dog and horse, venom allergens including such originating from stinging or biting insects such as those from the taxonomic order of Hymenoptera including bees (Apidae), wasps (Vespidea), and ants (Formicoidae).

In certain embodiments, a tumor immunogen or antigen, or cancer immunogen or antigen, can be encoded by the self-replicating RNA molecule. In certain embodiments, the tumor immunogens and antigens are peptide-containing tumor antigens, such as a polypeptide tumor antigen or glycoprotein tumor antigens.

Tumor immunogens and antigens appropriate for the use herein encompass a wide variety of molecules, such as (a) polypeptide-containing tumor antigens, including polypeptides (which can range, for example, from 8-20 amino acids in length, although lengths outside this range are also common), lipopolypeptides and glycoproteins.

In certain embodiments, tumor immunogens are, for example, (a) full length molecules associated with cancer cells, (b) homologs and modified forms of the same, including molecules with deleted, added and/or substituted portions, and (c) fragments of the same. Tumor immunogens include, for example, class I-restricted antigens recognized by CD8+ lymphocytes or class II-restricted antigens recognized by CD4+ lymphocytes.

In certain embodiments, tumor immunogens include, but are not limited to, (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSH-P1, PSM-P1, PSM-P2, associated with e.g., prostate cancer, (f) immunoglobulin idiotypes (associated with myeloma and B cell lymphomas, for example).

In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

C. Aqueous Solution for the Nucleic Acid Molecule

The nucleic acid molecule (such as RNA) is generally provided in the form of an aqueous solution, or a form that can be readily dissolved in an aqueous solution (e.g., lyophilized). The aqueous solution can be in water, or an aqueous solution that comprises a salt (e.g., NaCl), a buffer (e.g., a citrate buffer), a nonionic tonicifying agent (e.g., a saccharide), a polymer, a surfactant, or a combination thereof. If the formulation is intended for in vivo administration, it is preferable that the aqueous solution is a physiologically acceptable buffer that maintains a pH that is compatible with normal physiological conditions. Also, in certain instances, it may be desirable to maintain the pH at a particular level in order to insure the stability of certain components of the formulation.

For example, it may be desirable to prepare an aqueous solution that is isotonic and/or isosmotic. Hypertonic and hypotonic solutions sometimes could cause complications and undesirable effects when injected, such as post-administration swelling or rapid absorption of the composition because of differential ion concentrations between the composition and physiological fluids. To control tonicity, the emulsion may comprise a physiological salt, such as a sodium salt. Sodium chloride (NaCl), for example, may be used at about 0.9% (w/v) (physiological saline). Other salts that may be present include potassium chloride, potassium dihydrogen phosphate, disodium phosphate dehydrate, magnesium chloride, calcium chloride, etc. In an exemplary embodiment, the aqueous solution comprises 10 mM NaCl and other salts or non-ionic tonicifying agents. As described herein, non-ionic tonicifying agents can also be used to control tonicity. In an embodiment, hypertonic and hypotonic solutions are mixed (e.g., hypertonic RNA an hypotonic emulsion; hypotonic RNA and hypertonic emulsion) such that once mixed they form an isotonic solution.

The aqueous solution may be buffered. Any physiologically acceptable buffer may be used herein, such as citrate buffers, phosphate buffers, acetate buffers, succinate buffer, tris buffers, bicarbonate buffers, carbonate buffers, or the like. The pH of the aqueous solution will preferably be between 6.0-8.0, preferably about 6.2 to about 6.8. In some cases, certain amount of salt may be included in the buffer.

In other cases, salt in the buffer might interfere with complexation of nucleic acid molecules to the emulsion particle, therefore is avoided.

The aqueous solution may also comprise additional components such as molecules that change the osmolarity of the aqueous solution or molecules that stabilizes the nucleic acid molecule after complexation. For example, the osmolality can be adjusted using a non-ionic tonicifying agent, which are generally carbohydrates but can also be polymers. (See, e.g., Voet and Voet (1990) Biochemistry (John Wiley & Sons, New York.) Examples of suitable non-ionic tonicifying agents include sugars (e.g., trehalose, sucrose, dextrose, fructose, reduced palatinose, etc.), sugar alcohols (such as mannitol, sorbitol, xylitol, erythritol, lactitol, maltitol, glycerol, etc.), and combinations thereof. If desired, a nonionic polymer (e.g., a poly(alkyl glycol) such as polyethylene glycol, polypropylene glycol, or polybutlyene glycol) or nonionic surfactant can be used. These types of agents, in particular sugar and sugar alcohols, are also cryoprotectants that can procted RNA, and other nucleic acid molecules, when lyophilized. In exemplary embodiments, the buffer comprises from about 560 nM to 600 mM of trehalose, sucrose, sorbitol, or dextrose.

In some cases, it may be preferable to prepare an aqueous solution comprising the nucleic acid molecule as a hypertonic solution, and to prepare the cationic emulsion using unadulterated water or a hypotonic buffer. When the emulsion and the nucleic acid molecule are combined, the mixture becomes isotonic. For example, an aqueous solution comprising RNA can be a 2× hypertonic solution, and the cationic emulsion can be prepared using 10 mM Citrate buffer. When the RNA solution and the emulsion are mixed at 1:1 (v/v) ratio, the composition becomes isotonic. Based on desired relative amounts of the emulsion to the aqueous solution that comprises the nucleic acid molecule (e.g., 1:1 (v/v) mix, 2:1 (v/v) mix, 1:2 (v/v) mix, etc.), one can readily determine the tonicity of the aqueous solution that is required in order to achieve an isotonic mixture.

Similarly, compositions that have physiological osmolality may be desirable for in vivo administration. Physiological osmolality is from about 255 mOsm/kg water to about 315 mOsm/kg water. Sometimes, it may be preferable to prepare an aqueous solution comprising the nucleic acid molecule as a hyperosmolar solution, and to prepare the cationic emulsion using unadulterated water or a hypoosmolar buffer. When the emulsion and the nucleic acid molecule are combined, physiological osmolality is achieved. Of course, this can also be achieved using a hypoosmolar nucleic acid solution and a hyperosmolar buffer. Based on desired relative amounts of the emulsion to the aqueous solution that comprises the nucleic acid molecule (e.g., 1:1 (v/v) mix, 2:1 (v/v) mix, 1:2 (v/v) mix, etc.), one can readily determine the osmolality of the aqueous solution that is required in order to achieve an iso-osmolar mixture.

In certain embodiments, the aqueous solution comprising the nucleic acid molecule may further comprise a polymer or a surfactant, or a combination thereof. In an exemplary embodiment, the oil-in-water emulsion contains a poloxamer. In particular, the inventors have observed that adding Pluronic® F127 to the RNA aqueous solution prior to complexation to cationic emulsion particles led to greater stability and increased RNase resistance of the RNA molecule. Addition of pluronic F127 to RNA aqueous solution was also found to decrease the particle size of the RNA/CNE complex. Poloxamer polymers may also facilitate appropriate decomplexation/release of the RNA molecule, prevent aggregation of the emulsion particles, and have immune modulatory effect. Other polymers that may be used include, e.g., Pluronic® F68 or PEG300.

Alternatively or in addition, the aqueous solution comprising the nucleic acid molecule may comprise from about 0.05% to about 20% (w/v) polymer. For example, the cationic oil-in-water emulsion may comprise a polymer (e.g., a poloxamer such as Pluronic® F127, Pluronic® F68, or PEG300) at from about 0.05% to about 10% (w/v), such as 0.05%, 0.5%, 1%, or 5%.

The buffer system may comprise any combination of two or more molecules described above (salt, buffer, saccharide, polymer, etc). In an preferred embodiment, the buffer comprises 560 mM sucrose, 20 mM NaCl, and 2 mM Citrate, which can be mixed with a cationic oil in water emulsion described herein to produce a final aqueous phase that comprises 280 mM sucrose, 10 mM NaCl and 1 mM citrate. In other embodiments, the buffer comprises about 2-20 mM Citrate, which can be mixed with a cationic oil in water emulsion described herein to produce a final aqueous phase that comprises about 1-10 mM Citrate.

5. Methods of Preparation

In another aspect, the invention provides a method of preparing a composition that comprises a nucleic acid molecule complexed with a particle of a cationic oil-in-water emulsion at an N/P ratio of at least 4:1 and with average particle diameter from about 80 nm to about 180 nm, comprising: preparing a cationic oil-in-water emulsion wherein the emulsion comprises: (1) from about 0.2% to about 20% (v/v) oil, (2) from about 0.01% to about 2.5% (v/v) surfactant, and (3) a cationic lipid; and adding the nucleic acid molecule to the cationic oil-in-water emulsion so that the nucleic acid molecule complexes with the particle of the emulsion.

One exemplary approach to generate the cationic oil-in-water emulsion is by a process comprising: (1) combining the oil and the cationic lipid to form the oil phase of the emulsion; (2) providing an aqueous solution to form the aqueous phase of the emulsion; and (3) dispersing the oil phase in the aqueous phase, for example, by homogenization. Homogenization may be achieved in any suitable way, for example, using a commercial homogenizer (e.g., IKA T25 homogenizer, available at VWR International (West Chester, Pa.).

The cationic lipid may be dissolved in a suitable solvent, such as chloroform ($CHCl_3$), dichloromethane (DCM), ethanol, acetone, Tetrahydrofuran (THF), 2,2,2 trifluoroethanol, acetonitrile, ethyl acetate, hexane, Dimethylformamide (DMF), Dimethyl sulfoxide (DMSO), etc., and added directly to the oil component of the emulsion. Alternatively, the cationic lipid may be added to a suitable solvent to form a liposome suspension; then the liposome suspension may be added to the oil component of the emulsion. The cationic lipid may also be dissolved directly in the oil.

It may be desirable to heat the oil to a temperature between about 30° C. to about 65° C. to facilitate the dissolving of the lipid.

Desired amount of the cationic lipid (e.g., DOTAP) can be measured and either dissolved in a solvent, in water, or directly in oil to reach a desired final concentration as described and exemplified herein.

Solvents such as chloroform ($CHCl_3$) or dichloromethane (DCM) may be removed from the oil phase, e.g., by evaporation, prior to combining the aqueous phase and the oil phase or prior to homogenization. Alternatively, in instances where lipid solubility can be an issue, a primary emulsion can be made with the solvent (e.g. DCM) still in the oil phase. In such cases, the solvent can be removed (e.g., allowed to evaporate) from the primary emulsion prior to a secondary homogenization.

If the emulsion comprises one or more surfactants, the surfactant(s) may be included in the oil phase or the aqueous phase according to the conventional practice in the art. For example, SPAN®85 can be dissolved in the oil phase (e.g., squalene), and Tween® 80 may be dissolved in the aqueous phase (e.g., in a citrate buffer).

In another aspect, the invention provides a method of preparing a composition that comprises a nucleic acid molecule (such as RNA) complexed with a particle of a cationic oil-in-water emulsion, comprising: (i) providing a cationic oil-in-water emulsion as described herein; (ii) providing a aqueous solution comprising the nucleic acid molecule (such as RNA); and (iii) combining the oil-in-water emulsion of (i) and the aqueous solution of (iii), so that the nucleic acid molecule complexes with the particle of the emulsion. For example, a cationic oil-in-water emulsion may be combined with an aqueous solution comprising a nucleic acid molecule (e.g., an aqueous RNA solution) in any desired relative amounts, e.g., about 1:1 (v/v), about 1.5:1 (v/v), about 2:1 (v/v), about 2.5:1 (v/v), about 3:1 (v/v), about 3.5:1 (v/v), about 4:1 (v/v), about 5:1 (v/v), about 10:1 (v/v), about 1:1.5 (v/v), about 1:2 (v/v), about 1:2.5 (v/v), about 1:3 (v/v), about 1:3.5 (v/v), about 1:4 (v/v), about 1:1.5 (v/v), or about 1:1.10 (v/v), etc.

The concentration of each component of the post-complex composition (e.g., RNA-emulsion complex) can be readily determined according to relative amounts of the pre-complex oil-in-water emulsion and the aqueous solution comprising the nucleic acid molecule (e.g., an aqueous RNA solution) that are used. For example, when a cationic oil-in-water emulsion is combined with an aqueous solution comprising a nucleic acid molecule (e.g., an aqueous RNA solution) at 1:1 (v:v) ratio, the concentrations of the oil and cationic lipid become ½ of that of the pre-complex emulsion. Therefore, if an emulsion comprising 4.3% (w/v) squalene, 1.4 mg/mL DOTAP, 0.5% v/v SPAN®85 and 0.5% v/v Tween® 80 (referred herein as "CNE17") is combined with an aqueous RNA solution that comprises 560 mM sucrose, 20 mM NaCl, 2 mM Citrate, and 1% (w/v) Pluronic F127 at 1:1 (v:v), the post-complex composition comprises 2.15% (w/v) squalene, 0.7 mg/mL DOTAP, 0.25% v/v SPAN®85, 0.25% v/v Tween® 80, 280 mM sucrose, 10 mM NaCl, 1 mM Citrate, and 0.5% (w/v) Pluronic F127.

Additional optional steps to promote particle formation, to improve the complexation between the nucleic acid molecules and the cationic particles, to increase the stability of the nucleic acid molecule (e.g., to prevent degradation of an RNA molecule), to facilitate appropriate decomplexation/release of the nucleic acid molecules (such as an RNA molecule), or to prevent aggregation of the emulsion particles may be included. For example, a polymer (e.g., Pluronic® F127) or a surfactant may be added to the aqueous solution that comprises the nucleic acid molecule (such as RNA). In one exemplary embodiment, Pluronic® F127 is added to the RNA molecule prior to complexation to the emulsion particle.

The size of the emulsion particles can be varied by changing the ratio of surfactant to oil (increasing the ratio decreases droplet size), operating pressure (increasing operating pressure reduces droplet size), temperature (increasing temperature decreases droplet size), and other process parameters. Actual particle size will also vary with the particular surfactant, oil, and cationic lipid used, and with the particular operating conditions selected. Emulsion particle size can be verified by use of sizing instruments, such as the commercial Sub-Micron Particle Analyzer (Model N4MD) manufactured by the Coulter Corporation, and the parameters can be varied using the guidelines set forth above until the average diameter of the particles is 80 nm to 180 nm.

Optional processes for preparing the cationic oil-in-water emulsion (pre-complexation emulsion), or the nucleic acid molecule-emulsion complex, include, e.g., sterilization, particle size selection (e.g., removing large particles), filling, packaging, and labeling, etc.

For example, if the pre-complexation emulsion, or the nucleic acid molecule-emulsion complex, is formulated for in vivo administration, it may be sterilized, e.g., by filtering through a sterilizing grade filter (e.g., through a 0.22 micron filter). Other sterilization techniques include a thermal process, or a radiation sterilization process, or using pulsed light to produce a sterile composition.

The cationic oil-in-water emulsion described herein can be used to manufacture vaccines. Sterile and/or clinical grade cationic oil-in-water emulsions can be prepared using similar methods as described for MF59. See, e.g., Ott et al., Methods in Molecular Medicine, 2000, Volume 42, 211-228, in VACCINE ADJUVANTS (O'Hagan ed.), Humana Press. For example, similar to the manufacturing process of MF59, the oil phase and the aqueous phase of the emulsion can be combined and processed in an inline homogenizer to yield a coarse emulsion. The coarse emulsion can then be fed into a microfluidizer, where it can be further processed to obtain a stable submicron emulsion. The coarse emulsion can be passed through the interaction chamber of the microfluidizer repeatedly until the desired particle size is obtained. The bulk emulsion can then be filtered (e.g., though a 0.22-μm filter under nitrogen) to remove large particles, yielding emulsion bulk that can be filled into suitable containers (e.g., glass bottles). For vaccine antigens that have demonstrated long-term stability in the presence of oil-in-water emulsion for self storage, the antigen and emulsion may be combined and sterile-filtered (e.g., though a 0.22-μm filter membrane). The combined single vial vaccine can be filled into single-dose containers. For vaccine antigens where long-term stability has not been demonstrated, the emulsion can be supplied as a separate vial. In such cases, the emulsion bulk can be filtered-sterilized (e.g., though a 0.22-μm filter membrane), filled, and packaged in final single-dose vials.

Quality control may be optionally performed on a small sample of the emulsion bulk or admixed vaccine, and the bulk or admixed vaccine will be packaged into doses only if the sample passes the quality control test.

6. Pharmaceutical Compositions and Administration

In another aspect, the invention provides a pharmaceutical composition comprising a nucleic acid molecule complexed with a particle of a cationic oil-in-water emulsion, as described herein, and may further comprise one or more pharmaceutically acceptable carriers, diluents, or excipients. In preferred embodiments, the pharmaceutical composition is an immunogenic composition, which can be used as a vaccine.

The compositions described herein may be used to deliver a nucleic acid molecule to cells. For example, nucleic acid molecules (e.g., DNA or RNA) can be delivered to cells for a variety of purposes, such as to induce production of a desired gene product (e.g., protein), to regulate expression of a gene, for gene therapy and the like. The compositions described herein may also be used to deliver a nucleic acid molecule (e.g., DNA or RNA) to cells for therapeutic purposes, such as to treat a disease such as cancers or proliferative disorders, metabolic diseases, cardiovascular diseases, infections, allergies, to induce an immune response and the like. For example, nucleic acid molecules may be delivered to cells to inhibit the expression of a target gene. Such nucleic acid molecules include, e.g., antisense oligonucleotides, double-stranded RNAs, such as small interfering RNAs and the like. Double-stranded RNA molecules, such as small interfering RNAs, can trigger RNA interference, which specifically silences the corresponding target gene (gene knock down). Antisense oligonucleotides are single strands of DNA or RNA that are complementary to a chosen sequence. Generally, antisense RNA can prevent protein translation of certain messenger RNA strands by binding to them. Antisense DNA can be used to target a specific, complementary (coding or non-coding) RNA. Therefore, the cationic emulsions described herein are useful for delivering antisense oligonucleotides or double-stranded RNAs for treatment of, for example, cancer by inhibiting production of an oncology target.

The pharmaceutical compositions provided herein may be administered singly or in combination with one or more additional therapeutic agents. The methods of administration include, but are not limited to, oral administration, rectal administration, parenteral administration, subcutaneous administration, intravenous administration, intravitreal administration, intramuscular administration, inhalation, intranasal administration, topical administration, ophthalmic administration, and otic administration.

A therapeutically effective amount of the compositions described herein will vary depending on, among others, the disease indicated, the severity of the disease, the age and relative health of the subject, the potency of the compound administered, the mode of administration and the treatment desired.

In other embodiments, the pharmaceutical compositions described herein can be administered in combination with one or more additional therapeutic agents. The additional therapeutic agents may include, but are not limited to antibiotics, antibacterial agents, antiemetic agents, antifungal agents, anti-inflammatory agents, antiviral agents, immunomodulatory agents, cytokines, antidepressants, hormones, alkylating agents, antimetabolites, antitumour antibiotics, antimitotic agents, topoisomerase inhibitors, cytostatic agents, anti-invasion agents, antiangiogenic agents, inhibitors of growth factor function inhibitors of viral replication, viral enzyme inhibitors, anticancer agents, α-interferons, β-interferons, ribavirin, hormones, other toll-like receptor modulators, immunoglobulins (Igs), and antibodies modulating Ig function (such as anti-IgE (omalizumab)).

In certain embodiments, the pharmaceutical compositions provided herein are used in the treatment of infectious diseases including, but not limited to, disease caused by the pathogens disclosed herein, including viral diseases such as genital warts, common warts, plantar warts, rabies, respiratory syncytial virus (RSV), hepatitis B, hepatitis C, Dengue virus, yellow fever, herpes simplex virus (by way of example only, HSV-I, HSV-II, CMV, or VZV), molluscum contagiosum, vaccinia, variola, lentivirus, human immunodeficiency virus (HIV), human papilloma virus (HPV), hepatitis virus (hepatitis C virus, hepatitis B virus, hepatitis A virus), cytomegalovirus (CMV), varicella zoster virus (VZV), rhinovirus, enterovirus (e.g. EV71), adenovirus, coronavirus (e.g., SARS), influenza, para-influenza, mumps virus, measles virus, rubella virus, papovavirus, hepadnavirus, flavivirus, retrovirus, arenavirus (by way of example only, LCM, Junin virus, Machupo virus, Guanarito virus and Lassa Fever) and filovirus (by way of example only, ebola virus or marburg virus).

In certain embodiments, the pharmaceutical compositions provided herein are used in the treatment of bacterial, fungal, and protozoal infections including, but not limited to, malaria, tuberculosis and *mycobacterium avium*, leprosy; *pneumocystis* carnii, cryptosporidiosis, histoplasmosis, toxoplasmosis, trypanosome infection, leishmaniasis, infections caused by bacteria of the genus *Escherichia, Enterobacter, Salmonella, Staphylococcus, Klebsiella, Proteus, Pseudomonas, Streptococcus*, and *Chlamydia*, and fungal infections such as candidiasis, aspergillosis, histoplasmosis, and cryptococcal meningitis.

In certain embodiments, the pharmaceutical compositions provided herein are used in the treatment of respiratory diseases and/or disorders, dermatological disorders, ocular diseases and/or disorders, genitourinary diseases and/or disorders including, allograft rejection, auto-immune and allergic, cancer, or damaged or ageing skin such as scarring and wrinkles.

In another aspect, the invention provides a method for generating or potentiating an immune response in a subject in need thereof, such as a mammal, comprising administering an effective amount of a composition as disclosed herein. The immune response is preferably protective and preferably involves antibodies and/or cell-mediated immunity. The method may be used to induce a primary immune response and/or to boost an immune response.

In certain embodiments, the compositions disclosed herein may be used as a medicament, e.g., for use in raising or enhancing an immune response in a subject in need thereof, such as a mammal.

In certain embodiments, the compositions disclosed herein may be used in the manufacture of a medicament for generating or potentiating an immune response in a subject in need thereof, such as a mammal.

The invention also provides a delivery device pre-filled with a composition or a vaccine disclosed herein.

The mammal is preferably a human, but may be, e.g., a cow, a pig, a chicken, a cat or a dog, as the pathogens covered herein may be problematic across a wide range of species. Where the vaccine is for prophylactic use, the human is preferably a child (e.g., a toddler or infant), a teenager, or an adult; where the vaccine is for therapeutic use, the human is preferably a teenager or an adult. A vaccine intended for children may also be administered to adults, e.g., to assess safety, dosage, immunogenicity, etc.

One way of checking efficacy of therapeutic treatment involves monitoring pathogen infection after administration of the compositions or vaccines disclosed herein. One way of checking efficacy of prophylactic treatment involves monitoring immune responses, systemically (such as monitoring the level of IgG1 and IgG2a production) and/or mucosally (such as monitoring the level of IgA production), against the antigen. Typically, antigen-specific serum antibody responses are determined post-immunization but pre-challenge whereas antigen-specific mucosal antibody responses are determined post-immunization and post-challenge.

Another way of assessing the immunogenicity of the compositions or vaccines disclosed herein where the nucleic acid molecule (e.g., the RNA) encodes a protein antigen is to express the protein antigen recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within protein antigens.

The efficacy of the compositions can also be determined in vivo by challenging appropriate animal models of the pathogen of interest infection.

Dosage can be by a single dose schedule or a multiple dose schedule. Multiple doses may be used in a primary immunization schedule and/or in a booster immunization schedule. In a multiple dose schedule the various doses may be given by the same or different routes, e.g., a parenteral prime and mucosal boost, a mucosal prime and parenteral boost, etc. Multiple doses will typically be administered at least 1 week apart (e.g., about 2 weeks, about 3 weeks, about 4 weeks, about 6 weeks, about 8 weeks, about 10 weeks, about 12 weeks, about 16 weeks, etc.).

The compositions disclosed herein that include one or more antigens or are used in conjunction with one or more antigens may be used to treat both children and adults. Thus a human subject may be less than 1 year old, 1-5 years old, 5-15 years old, 15-55 years old, or at least 55 years old. Preferred subjects for receiving the compositions are the elderly (e.g., >50 years old, >60 years old, and preferably >65 years), the young (e.g., <5 years old), hospitalized patients, healthcare workers, armed service and military personnel, pregnant women, the chronically ill, or immunodeficient patients. The compositions are not suitable solely for these groups, however, and may be used more generally in a population.

The compositions disclosed herein that include one or more antigens or are used in conjunction with one or more antigens may be administered to patients at substantially the same time as (e.g., during the same medical consultation or visit to a healthcare professional or vaccination centre) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A C W135 Y vaccine), a respiratory syncytial virus vaccine, etc.

In certain embodiments, the compositions provided herein include or optionally include one or more immunoregulatory agents such as adjuvants. Exemplary adjuvants include, but are not limited to, a TH1 adjuvant and/or a TH2 adjuvant, further discussed below. In certain embodiments, the adjuvants used in the immunogenic compositions provide herein include, but are not limited to:

1. Mineral-Containing Compositions;
2. Oil Emulsions;
3. Saponin Formulations;
4. Virosomes and Virus-Like Particles;
5. Bacterial or Microbial Derivatives;
6. Bioadhesives and Mucoadhesives;
7. Liposomes;
8. Polyoxyethylene Ether and Polyoxyethylene Ester Formulations;
9. Polyphosphazene (PCPP);
10. Muramyl Peptides;
11. Imidazoquinolone Compounds;
12. Thiosemicarbazone Compounds;
13. Tryptanthrin Compounds;
14. Human Immunomodulators;
15. Lipopeptides;
16. Benzonaphthyridines;
17. Microparticles
18. Immunostimulatory polynucleotide (such as RNA or DNA; e.g., CpG-containing oligonucleotides)

EXEMPLIFICATION

The invention now being generally described, it will be more readily understood by reference to the following examples, which are included merely for purposes of illustration of certain aspects and embodiments of the present invention, and are not intended to limit the invention.

Example 1: Cationic Oil-in-Water Emulsions

Squalene, sorbitan trioleate (Span 85), polyoxy-ethylene sorbitan monololeate (Tween 80) were obtained from Sigma (St. Louis, Mo., USA). 1,2-Dioleoyl-3-trimethylammonium-propane (DOTAP) was purchased from Lipoid (Ludwigshafen Germany).

The components of the emulsions used in these studies are shown in Table 1.

TABLE 1

| CNE | Cationic Lipid (+) | mg/ml + Lipid | Surfactant | Squalene | Buffer/water |
|---|---|---|---|---|---|
| CNE17 | DOTAP (in DCM) | 1.40 | 0.5% SPAN 85 0.5% Tween 80 | 4.3% | 10 mM citrate buffer pH 6.5 |
| CMF32 | DOTAP | 3.2 | 0.5% SPAN 85 0.5% Tween 80 | 4.3% | 10 mM citrate buffer pH 6.5 |
| CMF34 | DOTAP | 4.4 | 0.5% SPAN 85 0.5% Tween 80 | 4.3% | 10 mM citrate buffer pH 6.5 |
| CMF35 | DOTAP | 5.0 | 0.5% SPAN 85 0.5% Tween 80 | 4.3% | 10 mM citrate buffer pH 6.5 |

CNEs were prepared similar to charged MF59 as previously described (Ott et al., Journal of Controlled Release, volume 79, pages 1-5, 2002). CMF 32, 34 and 35 were prepared with one major modification of that process. DOTAP was dissolved in the squalene directly, and no organic solvent was used. It was discovered that inclusion of a solvent in emulsions that contained greater than 1.6 mg/ml DOTAP produced a foamy feedstock that could not be microfluidized to produce an emulsion. Heating squalene to 37° C. allowed DOTAP to be directly dissolved in squalene, and then the oil phase could be successfully dispersed in the aqueous phase (e.g., by homogenization) to produce an emulsion. DOTAP is soluble in squalene and higher concentrations of DOTAP in squalene than those listed in Table 1 may be achieved. However, it has been reported that high dose of DOTAP can have toxic effects. See, e.g., Lappalainen et al., Pharm. Res., vol. 11(8):1127-31 (1994).

Briefly, squalene was heated to 37° C., and DOTAP was dissolved directly in squalene in the presence of SPAN 85. The resulting oil phase was then combined with the aqueous phase (Tween 80 in citrate buffer) and immediately homogenized for 2 min using an IKA T25 homogenizer at 24K RPM to produce a homogeneous feedstock (primary emulsions). The primary emulsions were passed three to five times through a M-110S Microfluidizer or a M-110P Microfluidizer (Microfluidics, Newton, Mass.) with an ice bath cooling coil at a homogenization pressure of approximately 15K-20K PSI. The 20 ml batch samples were removed from the unit and stored at 4° C.

It should be noted that the concentrations of the components of the CNEs, as described in Table 1, are concentrations calculated according the initial amounts of these components that were used to prepare the emulsions. It is understood that during the process of producing emulsions, or during the filter sterilization process, small amounts of squalene, DOTAP, or other components may be lost, and the actual concentrations of these components in the final product (e.g., a packaged, sterilized emulsion that is ready for administration) might be slightly lower, sometimes by up to about 20%. Sometimes, the actual concentrations of the components in the final product might be slightly lower by up to about 25%, or up to about 35%. However, the conventional practice in the art is to describe the concentration of a particular component based on the initial amount that is used to prepare the emulsion, instead of the actual concentration in the final product.

RNA Synthesis

Plasmid DNA encoding an alphavirus replicon (self-replicating RNA) was used as a template for synthesis of RNA in vitro. Each replicon contains the genetic elements required for RNA replication but lacks sequences encoding gene products that are necessary for particle assembly. The structural genes of the alphavirus genome were replaced by sequences encoding a heterologous protein (whose expression is driven by the alphavirus subgenomic promoter). Upon delivery of the replicons to eukaryotic cells, the positive-stranded RNA is translated to produce four non-structural proteins, which together replicate the genomic RNA and transcribe abundant subgenomic mRNAs encoding the heterologous protein. Due to the lack of expression of the alphavirus structural proteins, replicons are incapable of generating infectious particles. A bacteriophage T7 promoter is located upstream of the alphavirus cDNA to facilitate the synthesis of the replicon RNA in vitro, and the hepatitis delta virus (HDV) ribozyme located immediately downstream of the poly(A)-tail generates the correct 3'-end through its self-cleaving activity.

Following linearization of the plasmid DNA downstream of the HDV ribozyme with a suitable restriction endonuclease, run-off transcripts were synthesized in vitro using T7 or SP6 bacteriophage derived DNA-dependent RNA polymerase. Transcriptions were performed for 2 hours at 37° C. in the presence of 7.5 mM (T7 RNA polymerase) or 5 mM (SP6 RNA polymerase) final concentration of each of the nucleoside triphosphates (ATP, CTP, GTP and UTP) following the instructions provided by the manufacturer (Ambion, Austin, Tex.). Following transcription, the template DNA was digested with TURBO DNase (Ambion, Austin, Tex.). The replicon RNA was precipitated with LiCl and reconstituted in nuclease-free water. Uncapped RNA was capped post-transcriptionally with Vaccinia Capping Enzyme (VCE) using the ScriptCap $m^7G$ Capping System (Epicentre Biotechnologies, Madison, Wis.) as outlined in the user manual. Post-transcriptionally capped RNA was precipitated with LiCl and reconstituted in nuclease-free water. Alternatively, replicons may be capped by supplementing the transcription reactions with 6 mM (for T7 RNA polymerase) or 4 mM (for SP6 RNA polymerase) $m^7G(5')ppp(5')G$, a non-reversible cap structure analog (New England Biolabs, Beverly, Mass.) and lowering the concentration of guanosine triphosphate to 1.5 mM (for T7 RNA polymerase) or 1 mM (for SP6 RNA polymerase). The transcripts may be then purified by TURBO DNase (Ambion, Austin, Tex.) digestion followed by LiCl precipitation and a wash in 75% ethanol.

The concentration of the RNA samples was determined by measuring the optical density at 260 nm. Integrity of the in vitro transcripts was confirmed by denaturing agarose gel electrophoresis for the presence of the full length construct.

RNA Complexation

The number of nitrogens in solution was calculated from the cationic lipid concentration, DOTAP for example has 1 nitrogen that can be protonated per molecule. The RNA concentration was used to calculate the amount of phosphate in solution using an estimate of 3 nmols of phosphate per microgram of RNA. By varying the amount of RNA:Lipid, the N/P ratio can be modified. RNA was complexed to the CNEs in a range of nitrogen/phosphate ratios (N/P). Calculation of the N/P ratio was done by calculating the number of moles of protonatable nitrogens in the emulsion per milliliter. To calculate the number of phosphates, a constant of 3 nmols of phosphate per microgram of RNA was used. After the values were determined, the appropriate ratio of the emulsion was added to the RNA. Using these values, the RNA was diluted to the appropriate concentration and added directly into an equal volume of emulsion while vortexing lightly. The solution was allowed to sit at room temperature for approximately 2 hours. Once complexed the resulting solution was diluted to the appropriate concentration and used within 1 hour.

Particle Size Assay

Particle size of the emulsion was measured using a Zetasizer Nano ZS (Malvern Instruments, Worcestershire, UK) according to the manufacturer's instructions. Particle sizes are reported as the Z-Average (ZAve) with the polydispersity index (pdi). All samples were diluted in water prior to measurements. Additionally, particle size of the emulsion was measured using Horiba LA-930 particle sizer (Horiba Scientific, USA). Samples were diluted in water prior to measurements. Zeta potential was measured using Zetasizer Nano ZS using diluted samples according to the manufacturer's instructions.

Secreted Alkaline Phosphatase (SEAP) Assay

To assess the kinetics and amount of antigen production, an RNA replicon encoding for SEAP was administered with and without formulation to mice intramuscularly. Groups of 3 or 5 female Balb/C mice aged 8-10 weeks and weighing about 20 g were immunized with CNEs complexed with replicon RNA encoding for SEAP. Naked RNA was formulated in RNase free 1×PBS. A 100 µl dose was administered to each mouse (50 µl per site) in the quadriceps muscle. Blood samples were taken 1, 3, and 6 days post injection. Serum was separated from the blood immediately after collection, and stored at −30° C. until use.

A chemiluminescent SEAP assay Phospha-Light System (Applied Biosystems, Bedford, Mass.) was used to analyze the serum. Mouse sera was diluted 1:4 in 1× Phospha-Light dilution buffer. Samples were placed in a water bath sealed with aluminum sealing foil and heat inactivated for 30 minutes at 65° C. After cooling on ice for 3 minutes, and equilibrating to room temperature, 50 uL of Phospha-Light assay buffer was added to the wells and the samples were left at room temperature for 5 minutes. Then, 50 uL of reaction buffer containing 1:20 CSPD® (chemiluminecent alkaline phosphate substrate) substrate was added, and the luminescence was measured after 20 minutes of incubation at room temperature. Luminescence was measured on a Berthold Centro LB 960 luminometer (Oak Ridge, Tenn.) with a 1 second integration per well. The activity of SEAP in each sample was measured in duplicate and the mean of these two measurements is shown.

Example 2: The Effect of Particle Size on Immunogenicity

This example shows that particle size affects the immunogenicity of the CNE/RNA formulations.

A. Protocols for particle size assay and in vivo SEAP assay are described in Example 1. Protocols for murine immunogenicity studies are described in Example 3. FIG. 1A shows the results (arithmetic mean) of the in vivo SEAP assay. FIG. 1B shows the total IgG titers of individual animals in the BALB/c mice at 2wp1 and 2wp2 time points.

RNA complexation with CNE17 increased the size of the emulsion particles from about 220 nm to about 300 nm. As shown in FIG. 1A and FIG. 1B, as particle size increased, the expression levels of SEAP were reduced, and the host immune responses were also decreased.

B. CMF34 prepared at different sizes was complexed with RNA encoding RSV-F at a 7:1 theoretical N/P ratio and injected into the quadriceps muscle of Balb/C mice bilaterally (0.05 ml/site). Emulsion particle sizes were modulated by increasing the processing pressure of the microfluidizer. The data (Table 2) shows the highest anti-RSV F titers were generated when the emulsion particle size was smaller (see 120 nm and 90 nm particles) at two weeks after the first immunization.

TABLE 2

| Formulation | RNA dose | N/P ratio | 2wp1 GMT | 2wp2 GMT |
|---|---|---|---|---|
| 1 ug vA375 batch 1 | 1 ug | 7:1 | 16 | 151 |
| 1 ug vA375 batch 1 + CMF34 (5k PSI processing - 200 nm size) | 1 ug | 7:1 | 162 | 1644 |
| 1 ug vA375 batch 1 + CMF34 (7k PSI processing - 150 nm size) | 1 ug | 7:1 | 183 | 2540 |
| 1 ug vA375 batch 1 + CMF34 (12k PSI processing - 120 nm size) | 1 ug | 7:1 | 465 | 3563 |
| 1 ug vA375 batch 1 + CMF34 (20k PSI processing - 90 nm size) | 1 ug | 7:1 | 548 | 2542 |

Example 3: Effects of Buffer Compositions on Immunogenicity and Particle Size

In this example, various emulsions based on CNE17 but with different buffer components were prepared. Table 3 shows the compositions of the buffer-modified emulsions.

TABLE 3

| Base Emulsion | Buffer/water |
|---|---|
| CNE17: 4.3% Squalene, 0.5% SPAN 85, 0.5% Tween 80, 1.4 mg/ml DOTAP | 0 mM citrate buffer (in RNase-free dH$_2$O, no DCM) |
| CNE17: 4.3% Squalene, 0.5% SPAN 85, 0.5% Tween 80, 1.4 mg/ml DOTAP | 1 mM citrate buffer (in RNase-free dH$_2$O, no DCM) |
| CNE17: 4.3% Squalene, 0.5% SPAN 85, 0.5% Tween 80, 1.4 mg/ml DOTAP | 5 mM citrate buffer (in RNase-free dH$_2$O, no DCM) |
| CNE17: 4.3% Squalene, 0.5% SPAN 85, 0.5% Tween 80, 1.4 mg/ml DOTAP | 10 mM citrate buffer pH 6.5 300 mM Trehalose |
| CNE17: 4.3% Squalene, 0.5% SPAN 85, 0.5% Tween 80, 1.4 mg/ml DOTAP | 10 mM citrate buffer pH 6.5 300 mM Sucrose |
| CNE17: 4.3% Squalene, 0.5% SPAN 85, 0.5% Tween 80, 1.4 mg/ml DOTAP | 10 mM citrate buffer pH 6.5 300 mM Sorbitol |
| CNE17: 4.3% Squalene, 0.5% SPAN 85, 0.5% Tween 80, 1.4 mg/ml DOTAP | 10 mM citrate buffer pH 6.5 300 mM Dextrose |

In vitro binding assay showed that reducing the concentration of citrate buffer caused RNA to bind more tightly.

Results from murine immunogenicity studies showed that adding sugars to CNE17 did not significantly impact the immunogenicity of the CNE17-formulated RNA (Table 4, groups 9-12)). Slight increases in IgG titers were observed with the addition of sorbitol and dextrose.

TABLE 4

| Group # | Emulsion Description | N:P ratio | 2wp1 | 2wp2 | 2wp2/2wp1 ratio |
|---|---|---|---|---|---|
| 1 | 1 ug vA317 | — | 77 | 1,710 | 22.2 |
| 2 | RV01(15) | — | 3,441 | 59,557 | 17.3 |
| 3 | CNE17 DOTAP | 10:1 | 1,474 | 6,512 | 4.4 |
| 4 | CNE13 DDA | 18:1 | 482 | 8,385 | 17.4 |
| 5 | CMF37 DOTMA | 10:1 | 474 | 6,556 | 13.8 |
| 6 | CNE16 DOEPC | 12:1 | 1,145 | 9,673 | 8.4 |
| 7 | CMF42 DSTAP | 10:1 | 22 | 148 | 6.7 |
| 8 | DDA Liposomes | 18:1 | 898 | 5,333 | 5.9 |
| 9 | CNE17 with 300 mM Trehalose | 10:1 | 1,807 | 6,445 | 3.6 |
| 10 | CNE17 with 300 mM Sucrose | 10:1 | 1,042 | 5,515 | 5.3 |
| 11 | CNE17 with 300 mM Sorbitol | 10:1 | 1,209 | 8,874 | 7.3 |
| 12 | CNE17 with 300 mM Dextrose | 10:1 | 1,247 | 7,956 | 6.4 |

Groups 1-8 had 5 animals/group, and groups 9-12 had 10 animals/group.

Table 5 summarizes the results of murine immunogenicity studies when CNE17-formulated RNAs were prepared using different buffer systems.

TABLE 5

| Group # | RNA | Emulsion | N:P ratio | 2wp1 | 2wp2 | 2wp2/2wp1 ratio |
|---|---|---|---|---|---|---|
| 1 | 1 μg RSV-F* | PBS | — | 100 | 2269 | 23 |
| 2 | RV01(15) | PBS | — | 8388 | 105949 | 13 |
| 3 | 1 μg RSV-F* | CNE17 with 280 mM Sucrose | 10:1 | 898 | 9384 | 10 |
| 4 | 1 μg RSV-F* | CNE17 with 280 mM sucrose, 10 mM NaCl, 1 mM Citrate, | 10:1 | 1032 | 3184 | 3.1 |
| 5 | | CNE17 with 280 mM sucrose, 10 mM NaCl, 1 mM Citrate, 0.5% (w/v) and Pluronic F127 | 10:1 | 79 | 895 | 11.3 |

*vA375 replicon,
**vA317 replicon. Replicons were Ambion transcribed in HEPES buffer, then (i) LiCl precipitated, (ii) capped in Tris buffer, and (iii) LiCl precipitated. All groups had 8 animals/group.

Different buffer compositions also affected particle size. As shown in FIG. 2A, addition of sugar (sucrose) decreased the particle size of the RNA/CNE complex; addition of low concentrations of NaCl (at 10 mM) also decreased the particle size of the RNA/CNE complex (FIG. 2A). Citrate buffer did not affect the particle size of the RNA/CNE complex (FIG. 2B).

The effects of polymers on particle size are shown in FIG. 2C. In particular, addition of 0.5% pleuronic F127 to RNA buffer reduced the particle size of the RNA/CNE complex to the pre-complexation size (CNE particles without RNA).

The total antibody titers and neutralizing antibody titers of CNE17 in preferred buffer systems, 280 mM sucrose, 10 mM NaCl, and 1 mM Citrate; or 280 mM sucrose, 10 mM NaCl, 1 mM Citrate, and 0.5% (w/v) Pluronic F127, are shown in Table 5 (groups 4 and 5).

Example 4: Effects of N/P Ratio on Immunogenicity

In this example, the RNA replicon vA375, which encodes an RSV F antigen, was formulated as liposome (RV01), complexed with CNE17 at N/P of 10:1, and with CMF32 or CMF34 at theoretical N/P of 12;1, 10:1, 8:1, 6:1, and 4:1. Theoretical N/P ratios reflect the N/P ratios calculated according to the initial amounts of DOTAP and RNA that were used to prepare the formulations. Actual N/P ratios were slightly lower than theoretical N/P ratios because small amounts of DOTAP were lost during preparation of the emulsions. The GMT data reflect the mean $\log_{10}$ titer of individual mice in each group (8 mice/group). All formulations were adjusted to 300 mOsm/kg with sucrose prior to immunization. There were no obvious tolerability issues observed (e.g., body weight, early serum cytokines) with either CMF32 or CMF34 formulations.

Actual N/P ratios were determined by quantifying DOTAP content in CNE or CMF batches using HPLC with a charged aerosol detector (Corona Ultra, Chelmsford, Mass.). The CNE and CMF samples were diluted in isopropanol and injected onto a XTera C18 4.6×150 mm 3.5 um column (Waters, Milford, Mass.). The area under the curve was taken from the DOTAP peak in the chromatogram and the concentration was interpolated off a DOTAP standard curve. Using the actual DOTAP concentration, an actual N/P ratio was be calculated.

The immunogenicity data in Table 6 show that good titers were obtained when the actual N/P ratio was at least 4:1.

TABLE 6

| Formulation | RNA (µg/dose) | Theoretical N/P ratio | Actual N/P ratio | 2wp1 GMT | 2wp2 GMT | 2wp2/2wp1 (boost) |
|---|---|---|---|---|---|---|
| Naked | 1 | — | — | 68 | 1019 | 15 |
| RV01 | 1 | — | — | 9883 | 68116 | 7 |
| CNE17 | 1 | 10:1 | — | 1496 | 6422 | 4 |
| CMF32 | 1 | 12:1 | 9.4:1 | 2617 | 14246 | 5 |
| | 1 | 10:1 (batch 1) | 6.0:1 | 1537 | 10575 | 7 |
| | 1 | 10:1 (batch 2) | 8.0:1 | 2047 | 16244 | 8 |
| | 1 | 8:1 | 6.3:1 | 2669 | 7656 | 3 |
| | 1 | 6:1 | 4.7:1 | 1713 | 4715 | 3 |
| | 1 | 4:1 | 3.1:1 | 872 | 3773 | 4 |
| CMF34 | 1 | 12:1 | 7.4:1 | 3141 | 10134 | 3 |
| | 1 | 10:1 (batch 1) | 6.1:1 | 1906 | 11081 | 6 |
| | 1 | 10:1 (batch 2) | 7.0:1 | 2388 | 9857 | 4 |
| | 1 | 8:1 | 5:1 | 1913 | 8180 | 4 |
| | 1 | 6:1 | 3.7:1 | 1764 | 6209 | 4 |
| | 1 | 4:1 | 2.5:1 | 1148 | 4936 | 4 |

Sequences

A317 (SEQ ID NO:1)

A375 (SEQ ID NO:2)

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Those skilled in the art will recognize, or be able to ascertain using no more than routine experimentation, many equivalents to the specific embodiments of the invention described herein. Such equivalents are intended to be encompassed by the following embodiments.

The invention claimed is:

1. A method for generating an immune response in a subject, comprising administering to the subject an effective amount of an immunogenic cationic oil-in-water emulsion comprising emulsion particles that contain an oil core and a cationic lipid, and a nucleic acid molecule that is complexed to the emulsion particles, wherein:
   a) the nucleic acid is RNA that encodes a polypeptide antigen,
   b) the average diameter of the emulsion particles is from about 80 nm to about 180 nm, and
   c) the N/P of the emulsion is at least 4:1;
with the proviso that the nucleic acid molecule does not encode secreted alkaline phosphatase, and the further proviso that the nucleic acid molecule is not the RNA encoded by the plasmid A317, the sequence of which is given by SEQ ID NO:1;
whereby the immune response is generated in the subject.

2. The method of claim 1, wherein the RNA is self-replicating RNA.

3. The method of claim 1, wherein the immunogenic cationic oil-in-water emulsion is buffered, and has a pH from about 6.0 to about 8.0.

4. The method of claim 3, wherein the immunogenic cationic oil-in-water emulsion comprises a buffer selected from the group consisting of a citrate buffer, a succinate buffer, an acetate buffer, and combinations thereof.

5. The method of claim 4, wherein the buffer is a citrate buffer and the pH is about 6.5.

6. The method of claim 1, further comprising an inorganic salt.

7. The method of claim 6, wherein the inorganic salt concentration is no greater than 30 mM.

8. The method of claim 1, further comprising a nonionic tonicifying agent.

9. The method of claim 8, wherein the nonionic tonicifying agent is a sugar, a sugar alcohol or combinations thereof.

10. The method of claim 9, wherein the nonionic tonicifying agent is selected from the group consisting of sucrose, trehalose, sorbitol, dextrose and combinations thereof.

11. The method of claim 1, further comprising a polymer in the aqueous phase.

12. The method of claim 11, wherein the polymer is a poloxamer.

13. The method of claim 11, wherein the polymer is Pluronic F127.

14. The method of claim 11, wherein the emulsion contains about 0.05% to about 20% (w/v) polymer.

15. The method of claim 1, wherein the average diameter of the emulsion particles is from about 80 nm to about 130 nm.

16. The method of claim 1, wherein the N/P of the emulsion is from 4:1 to about 20:1.

17. The method of claim 1, wherein the N/P of the emulsion is from 4:1 to about 15:1.

18. The method of claim 1, wherein the cationic oil-in-water emulsion is isotonic with human blood.

19. The method of claim 1, wherein the oil core comprises an oil that is selected from the group consisting of: Castor oil, Coconut oil, Corn oil, Cottonseed oil, Evening primrose oil, Fish oil, Jojoba oil, Lard oil, Linseed oil, Olive oil, Peanut oil, Safflower oil, Sesame oil, Soybean oil, Squalene, Squalane, Sunflower oil, Wheatgerm oil, and combinations thereof.

20. The method of claim 19, wherein the oil is Squalene.

21. The method of claim 1, wherein the cationic lipid is selected from the group consisting of: 1,2-dioleoyloxy-3-(trimethylammonio)propane (DOTAP), 3β-[N—(N',N'-Dimethylaminoethane)-carbamoyl]Cholesterol (DC Cholesterol), dimethyldioctadecylammonium (DDA), 1,2-Dimyristoyl-3-TrimethylAmmoniumPropane (DMTAP), dipalmitoyl($C_{16:0}$)trimethyl ammonium propane (DPTAP), distearoyltrimethylammonium propane (DSTAP), N-[1-(2,3-dioleyloxy)propyl]-N,N,N-trimethylammonium chloride (DOTMA), N,N-dioleoyl-N,N-dimethylammonium chloride (DODAC), 1,2-dioleoyl-sn-glycero-3-ethylphosphocholine (DOEPC), 1,2-dioleoyl-3-dimethylammonium-propane (DODAP), 1,2-dilinoleyloxy-3-dimethylaminopropane (DLinDMA), Lipids E0001-E0118, and combinations thereof.

22. The method of claim 21, wherein the cationic lipid is DOTAP.

23. The method of claim 1, wherein the cationic lipid comprises a quaternary amine.

24. The method of claim 1, wherein the particle further comprises a surfactant.

25. The method of claim 24, wherein the surfactant is a nonionic surfactant.

26. The method of claim 25, wherein the surfactant is Sorbitan Trioleate, polysorbate 80, or a combination thereof.

27. The method of claim 1, wherein the emulsion further comprises an antioxidant.

\* \* \* \* \*

SEQUENCE LISTING

<160> NUMBER OF SEQ ID NOS: 3

<210> SEQ ID NO 1
<211> LENGTH: 12463
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 1
ataggcggcg catgagagaa gcccagacca attacctacc caaaatggag aaagttcacg        60
ttgacatcga ggaagacagc ccattcctca gagctttgca gcggagcttc ccgcagtttg       120
aggtagaagc caagcaggtc actgataatg accatgctaa tgccagagcg ttttcgcatc       180
tggcttcaaa actgatcgaa acggaggtgg acccatccga cacgatcctt gacattggaa       240
gtgcgcccgc ccgcagaatg tattctaagc acaagtatca ttgtatctgt ccgatgagat       300

```
gtgcggaaga tccggacaga ttgtataagt atgcaactaa gctgaagaaa aactgtaagg    360
aaataactga taaggaattg gacaagaaaa tgaaggagct cgccgccgtc atgagcgacc    420
ctgacctgga aactgagact atgtgcctcc acgacgacga gtcgtgtcgc tacgaagggc    480
aagtcgctgt ttaccaggat gtatacgcgg ttgacggacc gacaagtctc tatcaccaag    540
ccaataaggg agttagagtc gcctactgga taggctttga caccacccct tttatgttta    600
agaacttggc tggagcatat ccatcatact ctaccaactg ggccgacgaa accgtgttaa    660
cggctcgtaa cataggccta tgcagctctg acgttatgga gcggtcacgt agagggatgt    720
ccattcttag aaagaagtat ttgaaaccat ccaacaatgt tctattctct gttggctcga    780
ccatctacca cgagaagagg gacttactga ggagctggca cctgccgtct gtatttcact    840
tacgtggcaa gcaaaattac acatgtcggt gtgagactat agttagttgc gacgggtacg    900
tcgttaaaag aatagctatc agtccaggcc tgtatgggaa gccttcaggc tatgctgcta    960
cgatgcaccg cgagggattc ttgtgctgca aagtgacaga cacattgaac ggggagaggg   1020 tctctttttcc cgtgtgcacg tatgtgccag ctacattgtg tgaccaaatg actggcatac   1080
tggcaacaga tgtcagtgcg gacgacgcgc aaaaactgct ggttgggctc aaccagcgta   1140
tagtcgtcaa cggtcgcacc cagagaaaca ccaataccat gaaaaattac cttttgcccg   1200
tagtggccca ggcatttgct aggtgggcaa aggaatataa ggaagatcaa gaagatgaaa   1260
ggccactagg actacgagat agacagttag tcatggggtg ttgttgggct tttagaaggc   1320
acaagataac atctatttat aagcgcccgg atacccaaac catcatcaaa gtgaacagcg   1380
atttccactc attcgtgctg cccaggatag gcagtaacac attggagatc gggctgagaa   1440
caagaatcag gaaaatgtta gaggagcaca aggagccgtc acctctcatt accgccgagg   1500
acgtacaaga agctaagtgc gcagccgatg aggctaagga ggtgcgtgaa gccgaggagt   1560
tgcgcgcagc tctaccacct ttggcagctg atgttgagga gcccactctg gaagccgatg   1620
tagacttgat gttacaagag gctggggccg gctcagtgga gacacctcgt ggcttgataa   1680
aggttaccag ctacgatggc gaggacaaga tcggctctta cgctgtgctt tctccgcagg   1740
ctgtactcaa gagtgaaaaa ttatcttgca tccaccctct cgctgaacaa gtcatagtga   1800
taacacactc tggccgaaaa gggcgttatg ccgtggaacc ataccatggt aaagtagtgg   1860
tgccagaggg acatgcaata cccgtccagg actttcaagc tctgagtgaa agtgccacca   1920
ttgtgtacaa cgaacgtgag ttcgtaaaca ggtacctgca ccatattgcc acacatggag   1980
gagcgctgaa cactgatgaa gaatattaca aaactgtcaa gcccagcgag cacgacggcg   2040
aatacctgta cgacatcgac aggaaacagt gcgtcaagaa agaactagtc actgggctag   2100
ggctcacagg cgagctggtg gatcctccct tccatgaatt cgcctacgag agtctgagaa   2160
cacgaccagc cgctccttac caagtaccaa ccatagggot gtatggcgtg ccaggatcag   2220
gcaagtctgg catcattaaa agcgcagtca ccaaaaaaga tctagtggtg agcgccaaga   2280
aagaaaactg tgcagaaatt ataagggacg tcaagaaaat gaagggctga cgtcaatg    2340 ccagaactgt ggactcagtg ctcttgaatg gatgcaaaca ccccgtagag accctgtata   2400
ttgacgaagc ttttgcttgt catgcaggta ctctcagagc gctcatagcc attataagac   2460
ctaaaaaggc agtgctctgc ggggatccca acagtgcgg ttttttttaac atgatgtgcc   2520 tgaaagtgca ttttaaccac gagatttgca cacaagtctt ccacaaaagc atctctcgcc   2580
gttgcactaa atctgtgact tcggtcgtct caaccttgtt ttacgacaaa aaaatgagaa   2640
```

```
cgacgaatcc gaaagagact aagattgtga ttgacactac cggcagtacc aaacctaagc    2700
aggacgatct cattctcact tgtttcagag ggtgggtgaa gcagttgcaa atagattaca    2760
aaggcaacga aataatgacg gcagctgcct ctcaagggct gacccgtaaa ggtgtgtatg    2820
ccgttcggta caaggtgaat gaaaatcctc tgtacgcacc cacctcagaa catgtgaacg    2880
tcctactgac ccgcacggag gaccgcatcg tgtggaaaac actagccggc gacccatgga    2940
taaaaacact gactgccaag taccctggga atttcactgc cacgatagag gagtggcaag    3000
cagagcatga tgccatcatg aggcacatct tggagagacc ggaccctacc gacgtcttcc    3060
agaataaggc aaacgtgtgt tgggccaagg ctttagtgcc ggtgctgaag accgctggca    3120
tagacatgac cactgaacaa tggaacactg tggattattt tgaaacggac aaagctcact    3180
cagcagagat agtattgaac caactatgcg tgaggttctt tggactcgat ctggactccg    3240
gtctattttc tgcacccact gttccgttat ccattaggaa taatcactgg gataactccc    3300
cgtcgcctaa catgtacggg ctgaataaag aagtggtccg tcagctctct cgcaggtacc    3360
cacaactgcc tcgggcagtt gccactggaa gagtctatga catgaacact ggtacactgc    3420
gcaattatga tccgcgcata aacctagtac ctgtaaacag aagactgcct catgctttag    3480
tcctccacca taatgaacac ccacagagtg acttttcttc attcgtcagc aaattgaagg    3540
gcagaactgt cctggtggtc ggggaaaagt tgtccgtccc aggcaaaatg gttgactggt    3600
tgtcagaccg gcctgaggct accttcagag ctcggctgga tttaggcatc ccaggtgatg    3660
tgcccaaata tgacataata tttgttaatg tgaggaccccc atataaatac catcactatc    3720
agcagtgtga agaccatgcc attaagctta gcatgttgac caagaaagct tgtctgcatc    3780
tgaatcccgg cggaacctgt gtcagcatag gttatggtta cgctgacagg gccagcgaaa    3840
gcatcattgg tgctatagcg cggcagttca agttttcccg ggtatgcaaa ccgaaatcct    3900
cacttgaaga gacggaagtt ctgtttgtat tcattgggta cgatcgcaag gcccgtacgc    3960
acaatcctta caagctttca tcaaccttga ccaacattta tacaggttcc agactccacg    4020
aagccggatg tgcaccctca tatcatgtgg tgcgagggga tattgccacg gccaccgaag    4080
gagtgattat aaatgctgct aacagcaaag gacaacctgg cggaggggtg tgcggagcgc    4140
tgtataagaa attcccggaa agcttcgatt tacagccgat cgaagtagga aaagcgcgac    4200
tggtcaaagg tgcagctaaa catatcattc atgccgtagg accaaacttc aacaaagttt    4260
cggaggttga aggtgacaaa cagttggcag aggcttatga gtccatcgct aagattgtca    4320
acgataacaa ttacaagtca gtagcgattc cactgttgtc caccggcatc ttttccggga    4380
acaaagatcg actaaccaa tcattgaacc atttgctgac agctttagac accactgatg    4440
cagatgtagc catatactgc agggacaaga aatgggaaat gactctcaag gaagcagtgg    4500
ctaggagaga agcagtggag gagatatgca tatccgacga ctcttcagtg acagaacctg    4560
atgcagagct ggtgagggtg catccgaaga gttctttggc tggaaggaag gctacagca    4620 caagcgatgg caaaactttc tcatatttgg aagggaccaa gtttcaccag gcggccaagg    4680
atatagcaga aattaatgcc atgtggcccg ttgcaacgga ggccaatgag caggtatgca    4740
tgtatatcct cggagaaagc atgagcagta ttaggtcgaa atgccccgtc gaagagtcgg    4800
aagcctccac accacctagc acgctgcctt gcttgtgcat ccatgccatg actccagaaa    4860
gagtacagcg cctaaaagcc tcacgtccag aacaaattac tgtgtgctca tcctttccat    4920
tgccgaagta tagaatcact ggtgtgcaga agatccaatg ctcccagcct atattgttct    4980
caccgaaagt gcctgcgtat attcatccaa ggaagtatct cgtggaaaca ccaccggtag    5040
```

```
acgagactcc ggagccatcg gcagagaacc aatccacaga ggggacacct gaacaaccac    5100
cacttataac cgaggatgag accaggacta gaacgcctga gccgatcatc atcgaagagg    5160
aagaagagga tagcataagt ttgctgtcag atggcccgac ccaccaggtg ctgcaagtcg    5220
aggcagacat tcacgggccg ccctctgtat ctagctcatc ctggtccatt cctcatgcat    5280
ccgactttga tgtggacagt ttatccatac ttgacaccct ggagggagct agcgtgacca    5340
gcggggcaac gtcagccgag actaactctt acttcgcaaa gagtatggag tttctggcgc    5400
gaccggtgcc tgcgcctcga acagtattca ggaaccctcc acatcccgct ccgcgcacaa    5460
gaacaccgtc acttgcaccc agcagggcct gctcgagaac cagcctagtt tccaccccgc    5520
caggcgtgaa tagggtgatc actagagagg agctcgaggc gcttaccccg tcacgcactc    5580
ctagcaggtc ggtctcgaga accagcctgg tctccaaccc gccaggcgta aatagggtga    5640
ttacaagaga ggagtttgag gcgttcgtag cacaacaaca atgacggttt gatgcgggtg    5700
catacatctt ttcctccgac accggtcaag ggcatttaca caaaaatca gtaaggcaaa    5760 cggtgctatc cgaagtggtg ttggagagga ccgaattgga gatttcgtat gccccgcgcc    5820
tcgaccaaga aaaagaagaa ttactacgca agaaattaca gttaaatccc acacctgcta    5880
acagaagcag ataccagtcc aggaaggtgg agaacatgaa agccataaca gctagacgta    5940
ttctgcaagg cctagggcat tatttgaagg cagaaggaaa agtggagtgc taccgaaccc    6000
tgcatcctgt tcctttgtat tcatctagtg tgaaccgtgc cttttcaagc cccaaggtcg    6060
cagtggaagc ctgtaacgcc atgttgaaag agaactttcc gactgtggct tcttactgta    6120
ttattccaga gtacgatgcc tatttggaca tggttgacgg agcttcatgc tgcttagaca    6180
ctgccagttt ttgccctgca aagctgcgca gctttccaaa gaaacactcc tatttggaac    6240
ccacaatacg atcggcagtg ccttcagcga tccagaacac gctccagaac gtcctggcag    6300
ctgccacaaa aagaaattgc aatgtcacgc aaatgagaga attgcccgta ttggattcgg    6360 cggccttaa tgtggaatgc ttcaagaaat atgcgtgtaa taatgaatat tgggaaacgt    6420
ttaaagaaaa ccccatcagg cttactgaag aaaacgtggt aaaattacatt accaaattaa    6480 aaggaccaaa agctgctgct ctttttgcga agacacataa tttgaatatg ttgcaggaca    6540
taccaatgga caggttttgta atggacttaa agagagacgt gaaagtgact ccaggaacaa    6600
aacatactga agaacggccc aaggtacagg tgatccaggc tgccgatccg ctagcaacag    6660
cgtatctgtg cggaatccac cgagagctgg ttaggagatt aaatgcggtc ctgcttccga    6720
acattcatac actgtttgat atgtcggctg aagactttga cgctattata gccgagcact    6780
tccagcctgg ggattgtgtt ctggaaactg acatcgcgtc gtttgataaa agtgaggacg    6840
acgccatggc tctgaccgcg ttaatgattc tggaagactt aggtgtggac gcagagctgt    6900
tgacgctgat tgaggcggct ttcggcgaaa tttcatcaat acatttgccc actaaaacta    6960
aatttaaatt cggagccatg atgaaatctg gaatgttcct cacactgttt gtgaacacag    7020
tcattaacat tgtaatcgca agcagagtgt tgagagaacg gctaaccgga tcaccatgtg    7080
cagcattcat tggagatgac aatatcgtga aaggagtcaa atcggacaaa ttaatggcag    7140
acaggtgcgc cacctggttg aatatggaag tcaagattat agatgctgtg gtgggcgaga    7200
aagcgcctta tttctgtgga gggtttattt tgtgtgactc cgtgaccggc acagcgtgcc    7260
gtgtggcaga ccccctaaaa aggctgttta agcttggcaa acctctggca gcagacgatg    7320
aacatgatga tgacaggaga agggcattgc atgaagagtc aacacgctgg aaccgagtgg    7380
```

-continued

```
gtattctttc agagctgtgc aaggcagtag aatcaaggta tgaaaccgta ggaacttcca      7440
tcatagttat ggccatgact actctagcta gcagtgttaa atcattcagc tacctgagag      7500
gggcccctat aactctctac ggctaacctg aatggactac gacatagtct agtcgacgcc      7560
accatggaac tgctgatcct gaaggccaac gccatcacca ccatcctgac cgccgtgacc      7620
ttctgcttcg ccagcggcca gaacatcacc gaggaattct accagagcac ctgcagcgcc      7680
gtgagcaagg gctacctgag cgccctgcgg accggctggt acaccagcgt gatcaccatc      7740
gagctgtcca acatcaaaga aaacaagtgc aacggcaccg acgccaaggt gaaactgatc      7800
aagcaggaac tggacaagta caagaacgcc gtgaccgagc tgcagctgct gatgcagagc      7860 accccccgcca ccaacaaccg ggccagaaga gagctgcccc ggttcatgaa ctacaccctg      7920
aacaacgcca agaaaaccaa cgtgaccctg agcaagaagc ggaagcggcg gttcctgggc      7980
ttcctgctgg gcgtgggcag cgccatcgcc agcgggtgg ccgtgtccaa ggtgctgcac      8040
ctggaaggcg aggtgaacaa gatcaagtcc gccctgctgt ccaccaacaa ggccgtggtg      8100
tccctgagca cggcgtgag cgtgctgacc agcaaggtg tggatctgaa gaactacatc      8160
gacaagcagc tgctgcccat cgtgaacaag cagagctgca gcatcagcaa catcgagacc      8220
gtgatcgagt ccagcagaa gaacaaccgg ctgctggaaa tcacccggga gttcagcgtg      8280
aacgccggcg tgaccacccc cgtgagcacc tacatgctga ccaacagcga gctgctgtcc      8340
ctgatcaatg acatgcccat caccaacgac cagaaaaagc tgatgagcaa caacgtgcag      8400
atcgtgcggc agcagagcta ctccatcatg agcatcatca agaagaggt gctggcctac      8460 gtggtgcagc tgcccctgta cggcgtgatc gacacccct gctggaagct gcacaccagc      8520
cccctgtgca ccaccaacac caaagagggc agcaacatct gcctgacccg gaccgaccgg      8580
ggctggtact gcgacaacgc cggcagcgtg agcttcttcc ccaagccga gacctgcaag      8640 gtgcagagca accgggtgtt ctgcgacacc atgaacagcc tgaccctgcc ctccgaggtg      8700
aacctgtgca acgtggacat cttcaacccc aagtacgact gcaagatcat gacctccaag      8760
accgacgtga gcagctccgt gatcacctcc ctgggcgcca tcgtgagctg ctacggcaag      8820
accaagtgca ccgccagcaa caagaaccgg ggcatcatca gaccttcag caacggctgc      8880 gactacgtga gcaacaaggg cgtggacacc gtgagcgtgg caacacact gtactacgtg      8940 aataagcagg aaggcaagag cctgtacgtg aagggcgagc ccatcatcaa cttctacgac      9000
cccctggtgt tccccagcga cgagttcgac gccagcatca gccaggtcaa cgagaagatc      9060
aaccagagcc tggccttcat ccggaagagc gacgagctgc tgcacaatgt gaatgccggc      9120
aagagcacca ccaatatcat gatcaccaca atcatcatcg tgatcattgt gatcctgctg      9180
tctctgattg ccgtgggcct gctgctgtac tgcaaggccc gcagcacccc tgtgaccctg      9240
tccaaggacc agctgtccgg catcaacaat atcgccttct ccaactgaag tctagacggc      9300
gcgcccaccc agcggccgca tacagcagca attggcaagc tgcttacata gaactcgcgg      9360
cgattggcat gccgccttaa aattttatt ttattttct tttcttttcc gaatcggatt      9420 ttgttttaa tatttcaaaa aaaaaaaaa aaaaaaaaa aaaaaaaaa agggtcggca      9480 tggcatctcc acctcctcgc ggtccgacct gggcatccga aggaggacgc acgtccactc      9540
ggatggctaa gggagagcca cgtttaaacc agctccaatt cgccctatag tgagtcgtat      9600
tacgcgcgct cactggccgt cgttttacaa cgtcgtgact gggaaaaccc tggcgttacc      9660
caacttaatc gccttgcagc acatccccct ttcgccagct ggcgtaatag cgaagaggcc      9720
cgcaccgatc gcccttccca acagttgcgc agcctgaatg gcgaatggga cgcgccctgt      9780
```

```
agcggcgcat taagcgcggc gggtgtggtg gttacgcgca gcgtgaccgc tacacttgcc   9840
agcgccctag cgcccgctcc tttcgctttc ttcccttcct ttctcgccac gttcgccggc   9900
tttccccgtc aagctctaaa tcggggctc cctttagggt tccgatttag tgctttacgg    9960
cacctcgacc ccaaaaaact tgattagggt gatggttcac gtagtgggcc atcgccctga  10020
tagacggttt ttcgcccttt gacgttggag tccacgttct ttaatagtgg actcttgttc  10080
caaactggaa caacactcaa ccctatctcg gtcattctt ttgatttata agggattttg   10140
ccgatttcgg cctattggtt aaaaaatgag ctgatttaac aaaaatttaa cgcgaatttt  10200
aacaaaatat taacgcttac aatttaggtg cacttttcg gggaaatgtg cgcggaaccc   10260
ctatttgttt attttctaa atacattcaa atatgtatcc gctcatgaga caataaccct   10320
gataaatgct tcaataatat tgaaaaagga gagtatgag tattcaacat ttccgtgtcg    10380
cccttattcc cttttttgcg gcattttgcc ttcctgtttt tgctcaccca gaaacgctgg  10440
tgaaagtaaa agatgctgaa gatcagttgg gtgcacgagt gggttacatc gaactggatc  10500
tcaacagcgg taagatcctt gagagttttc gccccgaaga acgttttcca atgatgagca  10560
cttttaaagt tctgctatgt ggcgcggtat tatcccgtat tgacgccggg caagagcaac  10620
tcggtcgccg catacactat tctcagaatg acttggttga gtactcacca gtcacagaaa  10680
agcatcttac ggatggcatg acagtaagag aattatgcag tgctgccata accatgagtg  10740
ataacactgc ggccaactta cttctgacaa cgatcggagg accgaaggag ctaaccgctt  10800
ttttgcacaa catgggggat catgtaactc gccttgatcg ttgggaaccg gagctgaatg  10860
aagccatacc aaacgacgag cgtgacacca cgatgcctgt agcaatggca acaacgttgc  10920
gcaaactatt aactggcgaa ctacttactc tagcttcccg gcaacaatta atagactgga  10980
tggaggcgga taaagttgca ggaccacttc tgcgctcggc ccttccggct ggctggttta  11040
ttgctgataa atctggagcc ggtgagcgtg ggtctcgcgg tatcattgca gcactggggc  11100
cagatggtaa gccctcccgt atcgtagtta tctacacgac ggggagtcag gcaactatgg  11160
atgaacgaaa tagacagatc gctgagatag gtgcctcact gattaagcat tggtaactgt  11220
cagaccaagt ttactcatat atactttaga ttgatttaaa acttcatttt taatttaaaa  11280
ggatctaggt gaagatcctt tttgataatc tcatgaccaa aatcccttaa cgtgagtttt  11340
cgttccactg agcgtcagac cccgtagaaa agatcaaagg atcttcttga tccttttt   11400
ttctgcgcgt aatctgctgc ttgcaaacaa aaaaaccacc gctaccagcg gtggtttgtt  11460
tgccggatca agagctacca actctttttc cgaaggtaac tggcttcagc agagcgcaga  11520
taccaaatac tgttcttcta gtgtagccgt agttaggcca ccacttcaag aactctgtag  11580
caccgcctac atacctcgct ctgctaatcc tgttaccagt ggctgctgcc agtggcgata  11640
agtcgtgtct taccgggttg gactcaagac gatagttacc ggataaggcg cagcggtcgg  11700
gctgaacggg gggttcgtgc acacagccca gcttggagcg aacgacctac accgaactga  11760
gatacctaca gcgtgagcta tgagaaagcg ccacgcttcc cgaagggaga aaggcggaca  11820
ggtatccggt aagcggcagg gtcggaacag gagagcgcac gagggagctt ccaggggaa   11880
acgcctggta tctttatagt cctgtcgggt ttcgccacct ctgacttgag cgtcgatttt  11940
tgtgatgctc gtcaggggg cggagcctat ggaaaaacgc cagcaacgcg gccttttac    12000
ggttcctggc cttttgctgg ccttttgctc acatgttctt tcctgcgtta tccctgatt   12060
ctgtggataa ccgtattacc gcctttgagt gagctgatac cgctcgccgc agccgaacga  12120
```

| | |
|---|---:|
| ccgagcgcag cgagtcagtg agcgaggaag cggaagagcg cccaatacgc aaaccgcctc | 12180 |
| tccccgcgcg ttggccgatt cattaatgca gctggcacga caggtttccc gactggaaag | 12240 |
| cgggcagtga gcgcaacgca attaatgtga gttagctcac tcattaggca ccccaggctt | 12300 |
| tacactttat gctcccggct cgtatgttgt gtggaattgt gagcggataa caatttcaca | 12360 |
| caggaaacag ctatgaccat gattacgcca agcgcgcaat taaccctcac taaagggaac | 12420 |
| aaaagctggg taccgggccc acgcgtaata cgactcacta tag | 12463 |

<210> SEQ ID NO 2
<211> LENGTH: 11702
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

| | |
|---|---:|
| gcagtcacca aaaagatct agtggtgagc gccaagaaag aaaactgtgc agaaattata | 60 |
| agggacgtca agaaatgaa agggctggac gtcaatgcca gaactgtgga ctcagtgctc | 120 |
| ttgaatggat gcaaacaccc cgtagagacc ctgtatattg acgaagcttt tgcttgtcat | 180 |
| gcaggtactc tcagagcgct catagccatt ataagaccta aaaaggcagt gctctgcggg | 240 |
| gatcccaaac agtgcggttt ttttaacatg atgtgcctga agtgcatttt aaccacgag | 300 |
| atttgcacac aagtcttcca caaaagcatc tctcgccgtt gcactaaatc tgtgacttcg | 360 |
| gtcgtctcaa ccttgtttta cgacaaaaaa atgagaacga cgaatccgaa agagactaag | 420 |
| attgtgattg acactaccgg cagtaccaaa cctaagcagg acgatctcat tctcacttgt | 480 |
| ttcagagggt gggtgaagca gttgcaaata gattacaaag gcaacgaaat aatgacggca | 540 |
| gctgcctctc aagggctgac ccgtaaaggt gtgtatgccg ttcggtacaa ggtgaatgaa | 600 |
| aatcctctgt acgcacccac ctcagaacat gtgaacgtcc tactgacccg cacgaggac | 660 |
| cgcatcgtgt ggaaaacact agccggcgac ccatggataa aaacactgac tgccaagtac | 720 |
| cctgggaatt tcactgccac gatagaggag tggcaagcag agcatgatgc catcatgagg | 780 |
| cacatcttgg agagaccgga ccctaccgac gtcttccaga taaggcaaa cgtgtgttgg | 840 |
| gccaaggctt tagtgccggt gctgaagacc gctggcatag acatgaccac tgaacaatgg | 900 |
| aacactgtgg attattttga acggacaaaa gctcactcag cagagatagt attgaaccaa | 960 |
| ctatgcgtga ggttctttgg actcgatctg gactccggtc tattttctgc acccactgtt | 1020 |
| ccgttatcca ttaggaataa tcactgggat aactccccgt cgcctaacat gtacgggctg | 1080 |
| aataaagaag tggtccgtca gctctctcgc aggtacccac aactgcctcg ggcagttgcc | 1140 |
| actggaagag tctatgacat gaacactggt acactgcgca attatgatcc gcgcataaac | 1200 |
| ctagtacctg taaacagaag actgcctcat gctttagtcc tccaccataa tgaacaccca | 1260 |
| cagagtgact tttcttcatt cgtcagcaaa ttgaagggca aactgtcct ggtggtcggg | 1320 |
| gaaaagttgt ccgtcccagg caaaatggtt gactggttgt cagaccggcc tgaggctacc | 1380 |
| ttcagagctc ggctggattt aggcatccca ggtgatgtgc ccaaatatga cataatattt | 1440 |
| gttaatgtga ggacccccata taaataccat cactatcagc agtgtgaaga ccatgccatt | 1500 |
| aagcttagca tgttgaccaa gaaagcttgt ctgcatctga atccggcgg aacctgtgtc | 1560 |
| agcataggtt atggttacgc tgacagggcc agcgaaagca tcattggtgc tatagcgcgg | 1620 |
| cagttcaagt tttcccgggt atgcaaaccg aaatcctcac ttgaagagac ggaagttctg | 1680 |

```
tttgtattca ttgggtacga tcgcaaggcc cgtacgcaca atccttacaa gctttcatca    1740
accttgacca acatttatac aggttccaga ctccacgaag ccggatgtgc accctcatat    1800
catgtggtgc gagggatat tgccacggcc accgaaggag tgattataaa tgctgctaac    1860
agcaaaggac aacctggcgg aggggtgtgc ggagcgctgt ataagaaatt cccggaaagc    1920
ttcgatttac agccgatcga agtaggaaaa gcgcgactgg tcaaaggtgc agctaaacat    1980
atcattcatg ccgtaggacc aaacttcaac aaagtttcgg aggttgaagg tgacaaacag    2040
ttggcagagg cttatgagtc catcgctaag attgtcaacg ataacaatta caagtcagta    2100
gcgattccac tgttgtccac cggcatcttt tccgggaaca aagatcgact aacccaatca    2160
ttgaaccatt tgctgacagc tttagacacc actgatgcag atgtagccat atactgcagg    2220
gacaagaaat gggaaatgac tctcaaggaa gcagtggcta ggagagaagc agtggaggag    2280
atatgcatat ccgacgactc ttcagtgaca gaacctgatg cagagctggt gagggtgcat    2340
ccgaagagtt ctttggctgg aaggaagggc tacagcacaa gcgatggcaa aactttctca    2400
tatttggaag ggaccaagtt tcaccaggcg gccaaggata tagcagaaat taatgccatg    2460
tggcccgttg caacggaggc caatgagcag gtatgcatgt atatcctcgg agaaagcatg    2520
agcagtatta ggtcgaaatg ccccgtcgaa gagtcggaag cctccacacc acctagcacg    2580
ctgccttgct tgtgcatcca tgccatgact ccagaaagag tacagcgcct aaaagcctca    2640
cgtccagaac aaattactgt gtgctcatcc tttccattgc cgaagtatag aatcactggt    2700
gtgcagaaga tccaatgctc ccagcctata ttgttctcac cgaaagtgcc tgcgtatatt    2760
catccaagga agtatctcgt ggaaacacca ccggtagacg agactccgga gccatcggca    2820
gagaaccaat ccacagaggg gacacctgaa caaccaccac ttataaccga ggatgagacc    2880
aggactagaa cgcctgagcc gatcatcatc gaagaggaag aagaggatag cataagtttg    2940
ctgtcagatg gcccgaccca ccaggtgctg caagtcgagg cagacattca cgggccgccc    3000
tctgtatcta gctcatcctg gtccattcct catgcatccg actttgatgt ggacagttta    3060
tccatacttg acaccctgga gggagctagc gtgaccagcg gggcaacgtc agccgagact    3120
aactcttact tcgcaaagag tatggagttt ctggcgcgac cggtgcctgc gcctcgaaca    3180
gtattcagga accctccaca tcccgctccg cgcacaagaa caccgtcact tgcacccagc    3240
agggcctgct cgagaaccag cctagtttcc accccgccag gcgtgaatag ggtgatcact    3300
agagaggagc tcgaggcgct taccccgtca cggcactccta gcaggtcggt ctcgagaacc    3360
agcctggtct ccaacccgcc aggcgtaaat agggtgatta caagagagga gtttgaggcg    3420
ttcgtagcac aacaacaatg acggtttgat gcgggtgcat acatctttc ctccgacacc    3480 ggtcaaggc atttcaaaca aaaatcagta aggcaaacgg tgctatccga agtggtgttg    3540
gagaggaccg aattggagat ttcgtatgcc ccgcgcctcg accaagaaaa agaagaatta    3600
ctacgcaaga aattacagtt aaatcccaca cctgctaaca gaagcagata ccagtccagg    3660
aaggtggaga acatgaaagc cataacagct agacgtattc tgcaaggcct agggcattat    3720
ttgaaggcag aaggaaaagt ggagtgctac cgaaccctgc atcctgttcc tttgtattca    3780
tctagtgtga accgtgcctt ttcaagcccc aaggtcgcag tggaagcctg taacgccatg    3840
ttgaaagaga actttccgac tgtggcttct tactgtatta ttccagagta cgatgcctat    3900
ttggacatgg ttgacggagc ttcatgctgc ttagacactg ccagttttg ccctgcaaag    3960 ctgcgcagct ttccaaagaa acactccta ttggaaccca aatacgatc ggcagtgcct    4020
```

-continued

```
tcagcgatcc agaacacgct ccagaacgtc ctggcagctg ccacaaaaag aaattgcaat    4080
gtcacgcaaa tgagagaatt gcccgtattg gattcggcgg cctttaatgt ggaatgcttc    4140
aagaaatatg cgtgtaataa tgaatattgg gaaacgttta agaaaaccc catcaggctt     4200 actgaagaaa acgtggtaaa ttacattacc aaattaaaag gaccaaaagc tgctgctctt    4260
tttgcgaaga cacataattt gaatatgttg caggacatac caatggacag gtttgtaatg    4320
gacttaaaga gagacgtgaa agtgactcca ggaacaaaac atactgaaga acggcccaag    4380
gtacaggtga tccaggctgc cgatccgcta gcaacagcgt atctgtgcgg aatccaccga    4440
gagctggtta ggagattaaa tgcggtcctg cttccgaaca ttcatacact gtttgatatg    4500
tcggctgaag actttgacgc tattatagcc gagcacttcc agcctgggga ttgtgttctg    4560
gaaactgaca tcgcgtcgtt tgataaaagt gaggacgacg ccatggctct gaccgcgtta    4620
atgattctgg aagacttagg tgtggacgca gagctgttga cgctgattga ggcggctttc    4680
ggcgaaattt catcaataca tttgcccact aaaactaaat ttaaattcgg agccatgatg    4740
aaatctggaa tgttcctcac actgtttgtg aacacagtca ttaacattgt aatcgcaagc    4800
agagtgttga gagaacggct aaccggatca ccatgtgcag cattcattgg agatgacaat    4860
atcgtgaaag gagtcaaatc ggacaaatta atggcagaca ggtgcgccac ctggttgaat    4920
atggaagtca agattataga tgctgtggtg ggcgagaaag cgccttattt ctgtggaggg    4980 tttatttttgt gtgactccgt gaccggcaca gcgtgccgtg tggcagaccc cctaaaaagg    5040
ctgtttaagc ttggcaaacc tctggcagca gacgatgaac atgatgatga caggagaagg    5100
gcattgcatg aagagtcaac acgctggaac cgagtgggta ttctttcaga gctgtgcaag    5160
gcagtagaat caaggtatga aaccgtagga acttccatca tagttatggc catgactact    5220
ctagctagca gtgttaaatc attcagctac ctgagagggg cccctataac tctctacggc    5280
taacctgaat ggactacgac atagtctagt cgacgccacc atggaactgc tgatcctgaa    5340
ggccaacgcc atcaccacca tcctgaccgc cgtgaccttc tgcttcgcca gcggccagaa    5400
catcaccgag gaattctacc agagcacctg cagcgccgtg agcaagggct acctgagcgc    5460
cctgcgaccc ggctggtaca ccagcgtgat caccatcgag ctgtccaaca tcaaagaaaa    5520
caagtgcaac ggcaccgacg ccaaggtgaa actgatcaag caggaactgg acaagtacaa    5580
gaacgccgtg accgagctgc agctgctgat gcagagcacc cccgccacca caacccgggc    5640
cagaagagag ctgcccccggt tcatgaacta cacccctgaac aacgccaaga aaccaacgt     5700 gacccctgagc aagaagcgga gcggcggag cgccatcgcc agcggggtgg ccgtgtccaa    5760
ggtgctgcac ctggaaggcg aggtgaacaa gatcaagtcc gccctgctgt ccaccaacaa    5820
ggccgtggtg tccctgagca acggcgtgag cgtgctgacc agcaaggtgc tggatctgaa    5880
gaactacatc gacaagcagc tgctgcccat cgtgaacaag cagagctgca gcatcagcaa    5940
catcgagacc gtgatcgagt tccagcagaa gaacaaccgg ctgctggaaa tcacccggga    6000
gttcagcgtg aacgccggcg tgaccacccc cgtgagcacc tacatgctga ccaacagcga    6060
gctgctgtcc ctgatcaatg acatgcccat caccaacgac cagaaaaagc tgatgagcaa    6120
caacgtgcag atcgtgcggc agcagagcta ctccatcatg agcatcatca aggaagaggt    6180
gctggcctac gtggtgcagc tgcccctgta cggcgtgatc gacacccccct gctggaagct    6240 gcacaccagc cccctgtgca ccaccaacac caaagagggc agcaacatct gcctgacccg    6300
gaccgaccgg ggctggtact gcgacaacgc cggcagcgtg agcttcttcc cccaagccga    6360
gacctgcaag gtgcagagca accgggtgtt ctgcgacacc atgaacagcc tgaccctgcc    6420
```

```
ctccgaggtg aacctgtgca acgtggacat cttcaacccc aagtacgact gcaagatcat   6480
gacctccaag accgacgtga gcagctccgt gatcacctcc ctgggcgcca tcgtgagctg   6540
ctacggcaag accaagtgca ccgccagcaa caagaaccgg ggcatcatca agaccttcag   6600
caacggctgc gactacgtga gcaacaaggg cgtggacacc gtgagcgtgg caacacact    6660 gtactacgtg aataagcagg aaggcaagag cctgtacgtg aagggcgagc ccatcatcaa   6720
cttctacgac cccctggtgt tccccagcga cgagttcgac gccagcatca gccaggtcaa   6780
cgagaagatc aaccagagcc tggccttcat ccggaagtcc gacgagctgc tgcacaatgt   6840
gaatgccggc aagagcacca ccaatatcat gatcaccaca atcatcatcg tgatcattgt   6900
gatcctgctg tctctgattg ccgtgggcct gctgctgtac tgcaaggccc gcagcacccc   6960
tgtgacccta tccaaggacc agctgtccgg catcaacaat atcgccttct ccaactgaag   7020
tctagacggc gcgcccaccc agcggccgca tacagcagca attggcaagc tgcttacata   7080
gaactcgcgg cgattggcat gccgccttaa aattttatt ttattttct tttcttttcc    7140 gaatcggatt ttgtttttaa tatttcaaaa aaaaaaaaaa aaaaaaaaaa aaaaaaaaa    7200 aaaaagaag agcgtttaaa cacgtgatat ctggcctcat gggccttcct ttcactgccc    7260
gctttccagt cgggaaacct gtcgtgccag ctgcattaac atggtcatag ctgtttcctt   7320
gcgtattggg cgctctccgc ttcctcgctc actgactcgc tgcgctcggt cgttcgggta   7380
aagcctgggg tgcctaatga gcaaaaggcc agcaaaaggc caggaaccgt aaaaaggccg   7440
cgttgctggc gttttttccat aggctccgcc ccctgacga gcatcacaaa aatcgacgct    7500
caagtcagag gtggcgaaac ccgacaggac tataaagata ccaggcgttt cccctggaa    7560 gctcctcgt gcgctctcct gttccgaccc tgccgcttac cggatacctg tccgcctttc    7620
tcccttcggg aagcgtggcg ctttctcata gctcacgctg taggtatctc agttcggtgt   7680
aggtcgttcg ctccaagctg ggctgtgtgc acgaaccccc cgttcagccc gaccgctgcg   7740
ccttatccgg taactatcgt cttgagtcca acccggtaag acacgactta tcgccactgg   7800
cagcagccac tggtaacagg attagcagag cgaggtatgt aggcggtgct acagagttct   7860
tgaagtggtg gcctaactac ggctacacta agaacagt atttggtatc tgcgctctgc     7920
tgaagccagt taccttcgga aaagagttg gtagctcttg atccggcaaa caaaccaccg    7980
ctggtagcgg tggtttttttt gtttgcaagc agcagattac gcgcagaaaa aaggatctc   8040 aagaagatcc tttgatcttt tctacggggt ctgacgctca gtggaacgaa actcacgtt    8100 aagggattt ggtcatgaat acacggtgcc tgactgcgtt agcaatttaa ctgtgataaa    8160
ctaccgcatt aaagcttatc gatgataagc tgtcaaacat gagaattctt agaaaactc    8220 atcgagcatc aaatgaaact gcaatttatt catatcagga ttatcaatac catattttg    8280 aaaaagccgt ttctgtaatg aaggagaaaa ctcaccgagg cagttccata ggatggcaag   8340
atcctggtat cggtctgcga ttccgactcg tccaacatca atacaaccta ttaatttccc   8400
ctcgtcaaaa ataaggttat caagtgagaa atcaccatga gtgacgactg aatccggtga   8460
gaatggcaaa agcttatgca tttctttcca gacttgttca acaggccagc cattacgctc   8520
gtcatcaaaa tcactcgcat caaccaaacc gttattcatt cgtgattgcg cctgagcgag   8580
acgaaatacg cgatcgctgt taaaaggaca attacaaaca ggaatcgaat gcaaccggcg   8640
caggaacact gccagcgcat caacaatatt ttcacctgaa tcaggatatt cttctaatac   8700
ctggaatgct gttttcccgg ggatcgcagt ggtgagtaac catgcatcat caggagtacg   8760
```

```
gataaaatgc ttgatggtcg gaagaggcat aaattccgtc agccagttta gtctgaccat    8820
ctcatctgta acatcattgg caacgctacc tttgccatgt ttcagaaaca actctggcgc    8880
atcgggcttc ccatacaatc gatagattgt cgcacctgat tgcccgacat tatcgcgagc    8940
ccatttatac ccatataaat cagcatccat gttggaattt aatcgcggcc tcgagcaaga    9000
cgtttcccgt tgaatatggc tcataacacc ccttgtatta ctgtttatgt aagcagacag    9060
ttttattgtt catgagcgga tacatatttg aatgtattta gaaaataaaa caaatagggg    9120
ttccgcgcac atttccccga aaagtgccac ctaaattgta agcgttaata ttttgttaaa    9180
attcgcgtta aattttttgtt aaatcagctc attttttaac caataggccg aaatcggcaa    9240
aatcccttat aaatcaaaag aatagaccga gatagggttg agtggccgct acagggcgct    9300
cccattcgcc attcaggctg cgcaactgtt gggaagggcg tttcggtgcg ggcctcttcg    9360
ctattacgcc agctggcgaa aggggggatgt gctgcaaggc gattaagttg ggtaacgcca    9420
gggttttccc agtcacacgc gtaatacgac tcactataga taggcggcgc atgagagaag    9480
cccagaccaa ttacctaccc aaaatggaga agttcacgt tgacatcgag gaagacagcc    9540
cattcctcag agctttgcag cggagcttcc cgcagtttga ggtagaagcc aagcaggtca    9600
ctgataatga ccatgctaat gccagagcgt tttcgcatct ggcttcaaaa ctgatcgaaa    9660
cggaggtgga cccatccgac acgatccttg acattggaag tgcgcccgcc cgcagaatgt    9720
attctaagca caagtatcat tgtatctgtc cgatgagatg tgcggaagat ccggacagat    9780
tgtataagta tgcaactaag ctgaagaaaa actgtaagga aataactgat aaggaattgg    9840
acaagaaaat gaaggagctc gccgccgtca tgagcgaccc tgacctggaa actgagacta    9900
tgtgcctcca cgacgacgag tcgtgtcgct acgaagggca agtcgctgtt taccaggatg    9960
tatacgcggt tgacgaccg acaagtctct atcaccaagc caataaggga gttagagtcg    10020
cctactggat aggctttgac accaccccctt ttatgtttaa gaacttggct ggagcatatc    10080
catcatactc taccaactgg gccgacgaaa ccgtgttaac ggctcgtaac ataggcctat    10140
gcagctctga cgttatggag cggtcacgta gagggatgtc cattcttaga aagaagtatt    10200
tgaaaccatc caacaatgtt ctattctctg ttggctcgac catctaccac gagaagaggg    10260
acttactgag gagctggcac ctgccgtctg tatttcactt acgtggcaag caaaattaca    10320
catgtcggtg tgagactata gttagttgcg acgggtacgt cgttaaaaga atagctatca    10380
gtccaggcct gtatgggaag ccttcaggct atgctgctac gatgcaccgc gagggattct    10440
tgtgctgcaa agtgacagac acattgaacg gggagagggt ctcttttccc gtgtgcacgt    10500
atgtgccagc tacattgtgt gaccaaatga ctggcatact ggcaacagat gtcagtgcgg    10560
acgacgcgca aaaactgctg gttgggctca accagcgtat agtcgtcaac ggtcgcaccc    10620
agagaaacac caataccatg aaaaattacc ttttgcccgt agtggcccag gcatttgcta    10680
ggtgggcaaa ggaatataag gaagatcaag aagatgaaag gccactagga ctacgagata    10740
gacagttagt catgggtgt tgttgggctt ttagaaggca caagataaca tctatttata    10800
agcgcccgga tacccaaacc atcatcaaag tgaacagcga tttccactca ttcgtgctgc    10860
ccaggatagg cagtaacaca ttggagatcg ggctgagaac aagaatcagg aaaatgttag    10920
aggagcacaa ggagccgtca cctctcatta ccgccgagga cgtacaagaa gctaagtgcg    10980
cagccgatga ggctaaggag gtgcgtgaag ccgaggagtt gcgcgcagct ctaccacctt    11040
tggcagctga tgttgaggag cccactctgg aagccgatgt agacttgatg ttacaagagg    11100 ctgggccgg ctcagtggag acacctcgtg gcttgataaa ggttaccagc tacgatggcg    11160
```

```
aggacaagat cggctcttac gctgtgcttt ctccgcaggc tgtactcaag agtgaaaaat   11220
tatcttgcat ccaccctctc gctgaacaag tcatagtgat aacacactct ggccgaaaag   11280
ggcgttatgc cgtggaacca taccatggta aagtagtggt gccagaggga catgcaatac   11340
ccgtccagga ctttcaagct ctgagtgaaa gtgccaccat tgtgtacaac gaacgtgagt   11400
tcgtaaacag gtacctgcac catattgcca cacatggagg agcgctgaac actgatgaag   11460
aatattacaa aactgtcaag cccagcgagc acgacggcga atacctgtac gacatcgaca   11520
ggaaacagtg cgtcaagaaa gaactagtca ctgggctagg gctcacaggc gagctggtgg   11580
atcctcgctt ccatgaattc gcctacgaga gtctgagaac acgaccagcc gctccttacc   11640
aagtaccaac catagggtg tatggcgtgc caggatcagg caagtctggc atcattaaaa   11700
gc                                                                 11702

<210> SEQ ID NO 3
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
aaaaaaaaaa aaaaaaaaaa aaaaaaaaaa                                      30
```